United States Patent
Bower et al.

(10) Patent No.: US 11,083,887 B2
(45) Date of Patent: Aug. 10, 2021

(54) TECHNIQUES FOR SENSING INCORRECT LEAD CONNECTION TO AN IMPLANTABLE STIMULATOR DEVICE

(71) Applicant: Boston Scientific Neuromodulation Corporation, Valencia, CA (US)

(72) Inventors: Kelsey Bower, Cleveland Heights, OH (US); G. Karl Steinke, Valencia, CA (US); Hemant Bokil, Santa Monica, CA (US); Ara Sarian, Burbank, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 228 days.

(21) Appl. No.: 16/128,131

(22) Filed: Sep. 11, 2018

(65) Prior Publication Data

US 2019/0076645 A1    Mar. 14, 2019

Related U.S. Application Data

(60) Provisional application No. 62/568,111, filed on Oct. 4, 2017, provisional application No. 62/557,640, filed on Sep. 12, 2017.

(51) Int. Cl.
*A61N 1/05* (2006.01)
*A61N 1/36* (2006.01)
(Continued)

(52) U.S. Cl.
CPC .............. *A61N 1/0551* (2013.01); *A61N 1/05* (2013.01); *A61N 1/0534* (2013.01); *A61N 1/36* (2013.01);
(Continued)

(58) Field of Classification Search
CPC ...... A61N 1/0551; A61N 1/05; A61N 1/0534; A61N 1/36; A61N 1/36071;
(Continued)

(56) References Cited

U.S. PATENT DOCUMENTS

| 4,964,407 A | 10/1990 | Baker, Jr. et al. |
| 6,181,969 B1 | 1/2001 | Gord |

(Continued)

OTHER PUBLICATIONS

International Search Report and Written Opinion regarding corresponding PCT Application No. PCT/US2018/050503, dated Dec. 4, 2018.

(Continued)

*Primary Examiner* — William J Levicky
*Assistant Examiner* — Minh Duc G Pham
(74) *Attorney, Agent, or Firm* — Lewis & Reese, PLLC

(57) ABSTRACT

Incorrect connection or mapping of leads' proximal terminals to the ports of an Implantable Stimulator Device (ISD), such as an implantable pulse generator or an external trial stimulator, is a concern, and this disclosure is directed to use of measurement and identification algorithms to either determine that leads are properly connected to their assigned ISD ports, or to determine which leads are connected to the ports even if the leads are not preassigned to the ports. Particular focus is given in the disclosed technique to assessing leads that comprise larger number of electrodes than are supported at each port, and thus have more than one proximal terminal that connect to more than one port of the ISD.

20 Claims, 33 Drawing Sheets

(51) Int. Cl.
*A61N 1/375* (2006.01)
*A61N 1/372* (2006.01)
*A61N 1/08* (2006.01)
*A61B 5/00* (2006.01)
*A61N 1/39* (2006.01)
*A61N 1/362* (2006.01)

(52) U.S. Cl.
CPC ..... *A61N 1/36071* (2013.01); *A61N 1/36135* (2013.01); *A61N 1/3752* (2013.01); *A61N 1/37211* (2013.01); *A61B 5/407* (2013.01); *A61N 1/362* (2013.01); *A61N 1/36062* (2017.08); *A61N 1/36067* (2013.01); *A61N 1/36082* (2013.01); *A61N 1/36125* (2013.01); *A61N 1/36171* (2013.01); *A61N 1/37241* (2013.01); *A61N 1/37247* (2013.01); *A61N 1/3956* (2013.01); *A61N 2001/083* (2013.01)

(58) Field of Classification Search
CPC ............ A61N 1/36135; A61N 1/37211; A61N 1/3752; A61N 1/36062; A61N 1/36067; A61N 1/36082; A61N 1/36125; A61N 1/36171; A61N 1/362; A61N 1/37241; A61N 1/37247; A61N 1/3956
USPC ........................................................ 607/117
See application file for complete search history.

(56) References Cited

U.S. PATENT DOCUMENTS

| | | |
|---|---|---|
| 6,516,227 B1 | 2/2003 | Meadows et al. |
| 7,831,307 B1 | 11/2010 | Moffitt |
| 8,463,402 B2 | 6/2013 | Zhu et al. |
| 8,606,362 B2 | 12/2013 | He et al. |
| 8,620,436 B2 | 12/2013 | Parramon et al. |
| 8,649,873 B2 | 2/2014 | Moffitt et al. |
| 8,731,679 B2 | 5/2014 | Ternes et al. |
| 8,761,897 B2 | 6/2014 | Kaula et al. |
| 8,768,453 B2 | 7/2014 | Parramon et al. |
| 9,061,140 B2 | 6/2015 | Shi et al. |
| 9,089,704 B2 | 7/2015 | Kelly |
| 9,446,243 B2 | 9/2016 | Marnfeldt et al. |
| 9,724,508 B2 | 8/2017 | Lamont et al. |
| 2010/0137943 A1 | 6/2010 | Zhu |
| 2011/0112609 A1* | 5/2011 | Peterson ................ G16H 20/40 607/59 |
| 2011/0270065 A1* | 11/2011 | Ternes ............... A61N 1/36114 600/373 |
| 2012/0191153 A1 | 7/2012 | Swerdlow et al. |
| 2012/0290034 A1 | 11/2012 | Rochat et al. |
| 2013/0184794 A1 | 7/2013 | Feldman et al. |
| 2015/0119958 A1 | 4/2015 | Li et al. |
| 2015/0231402 A1 | 8/2015 | Aghassian |
| 2015/0360038 A1 | 12/2015 | Zottola et al. |
| 2016/0184591 A1 | 6/2016 | Feldman et al. |
| 2017/0113049 A1 | 4/2017 | Kothandaraman et al. |
| 2017/0281958 A1 | 10/2017 | Serrano Carmona et al. |

OTHER PUBLICATIONS

U.S. Appl. No. 62/557,640, Steinke et al., filed Sep. 12, 2017.
U.S. Appl. No. 62/568,111, Shah et al., filed Oct. 4, 2017.

* cited by examiner

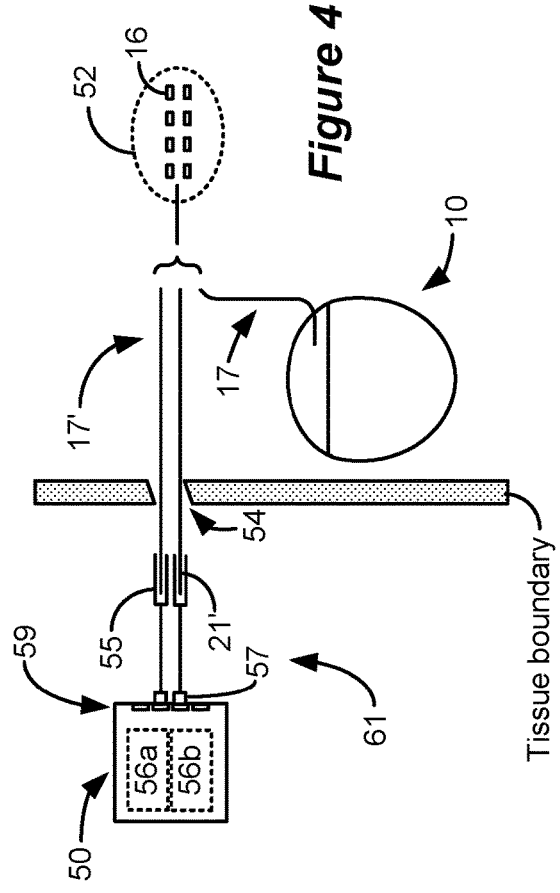
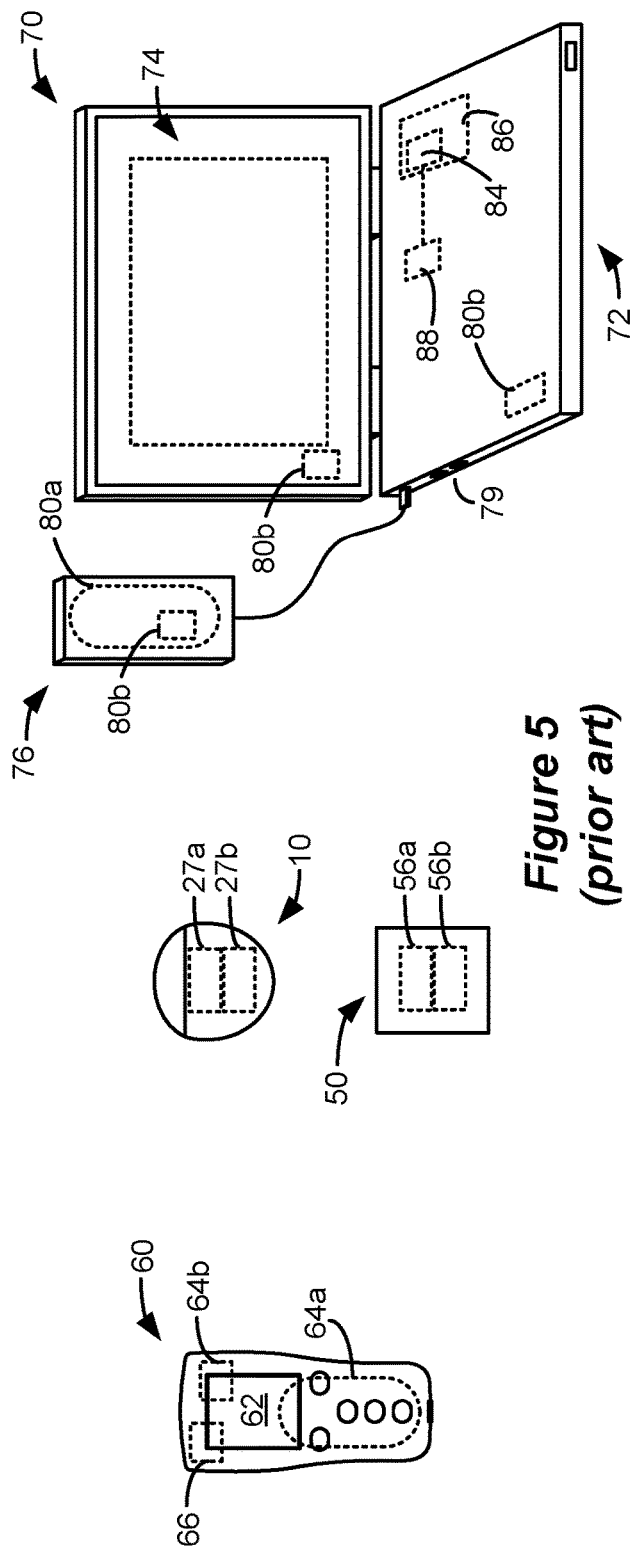
Figure 4 (prior art)
Figure 5 (prior art)

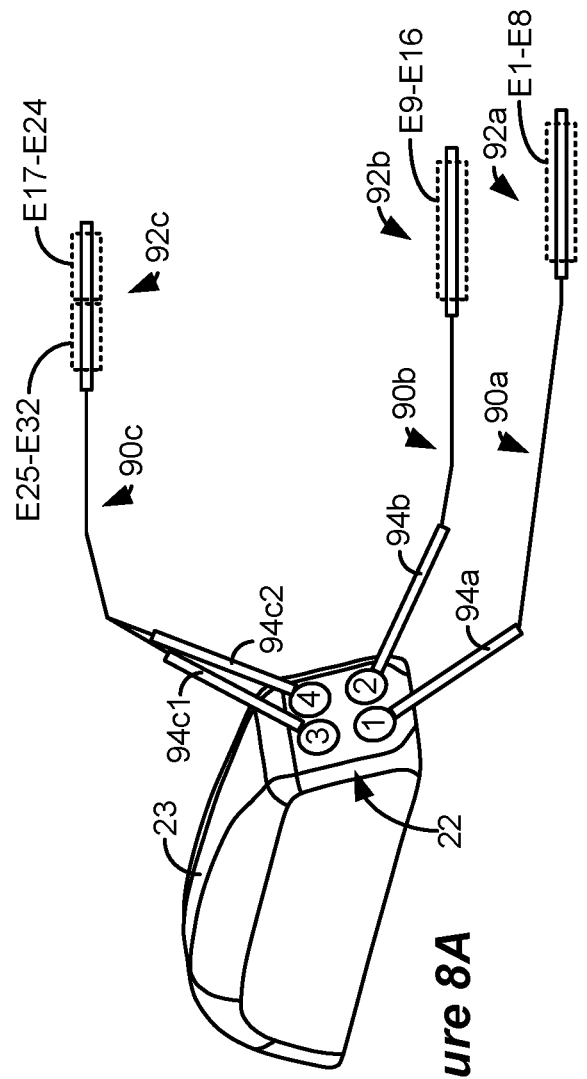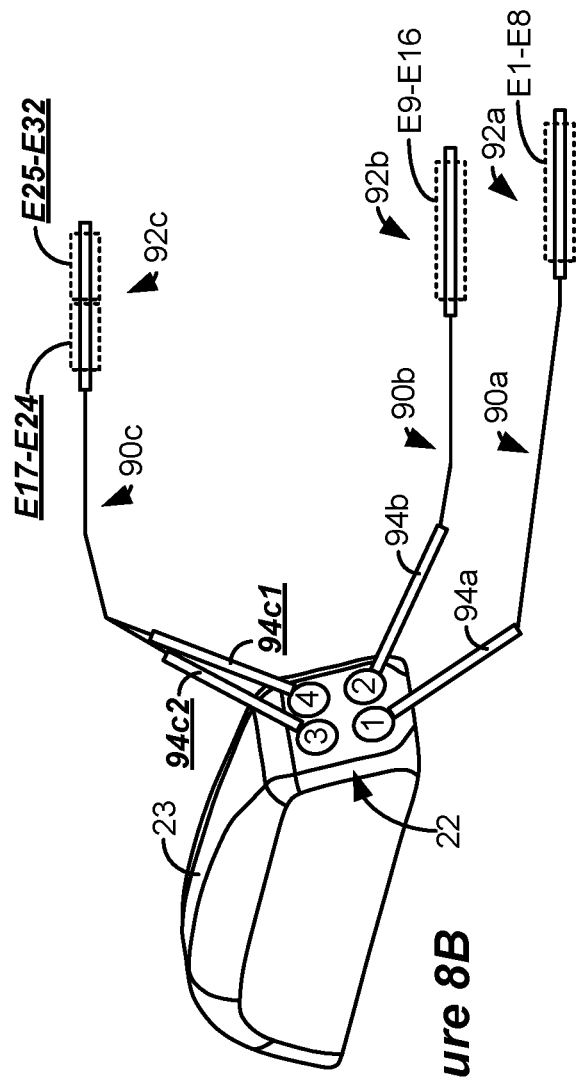
Figure 8A
Figure 8B

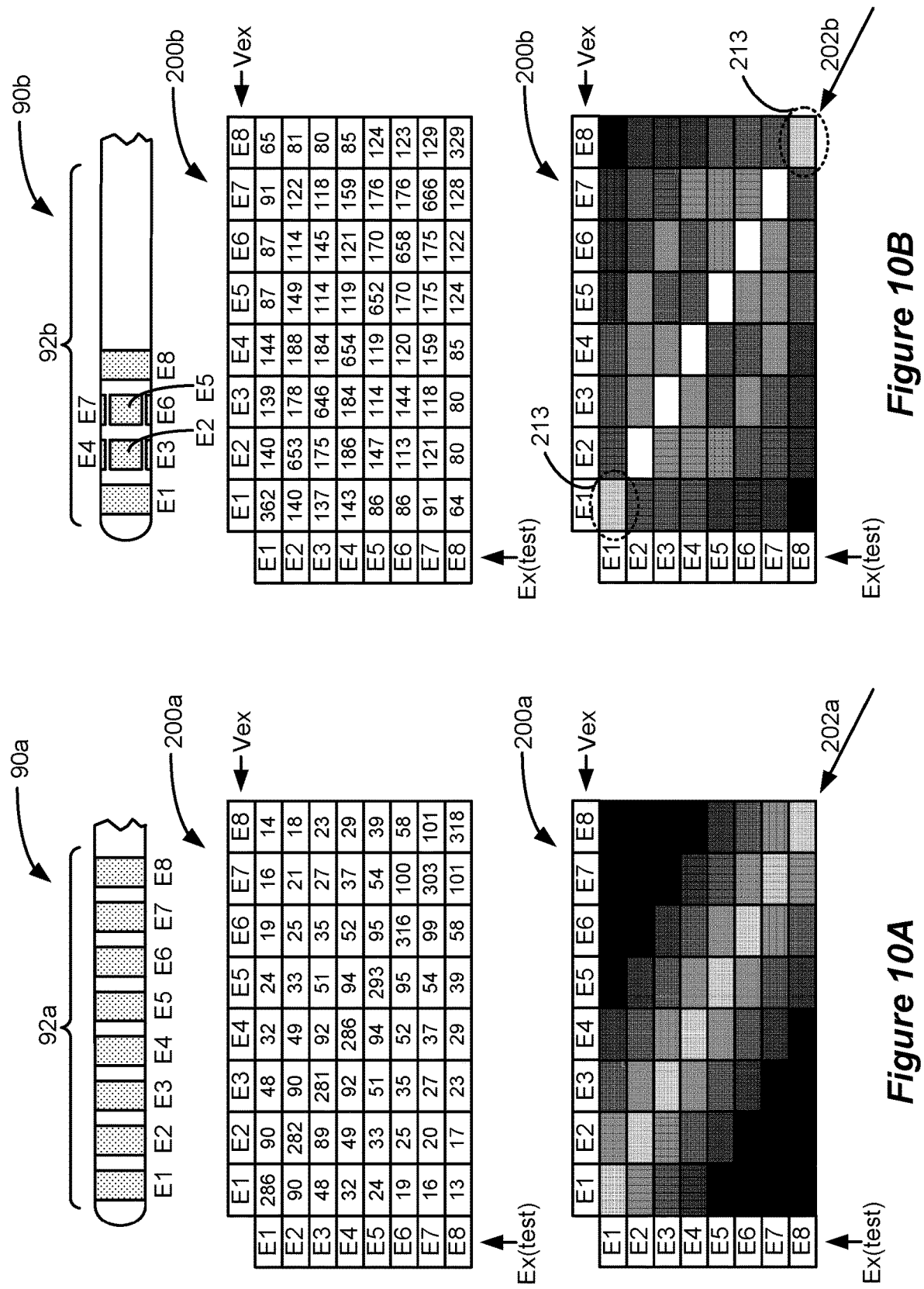

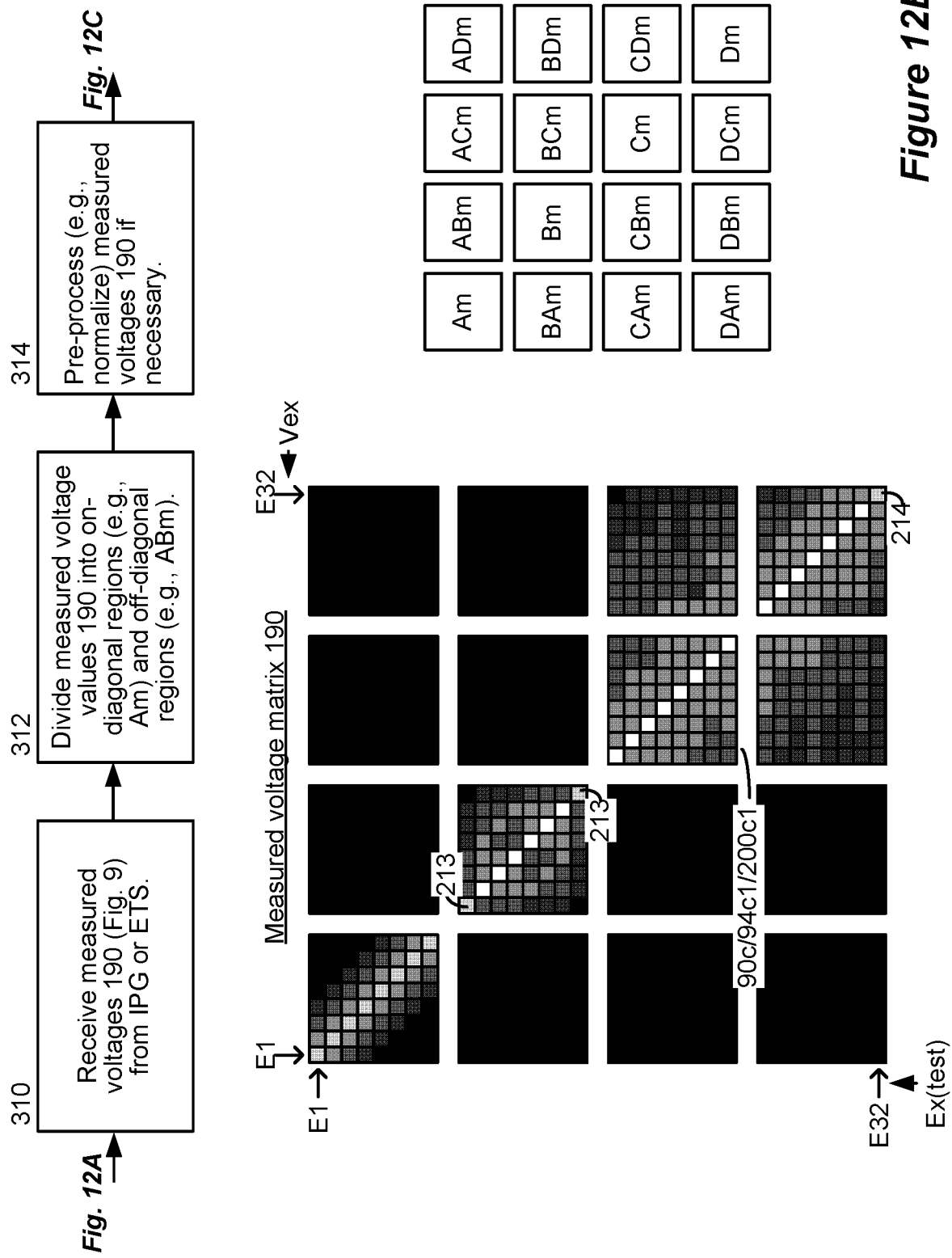

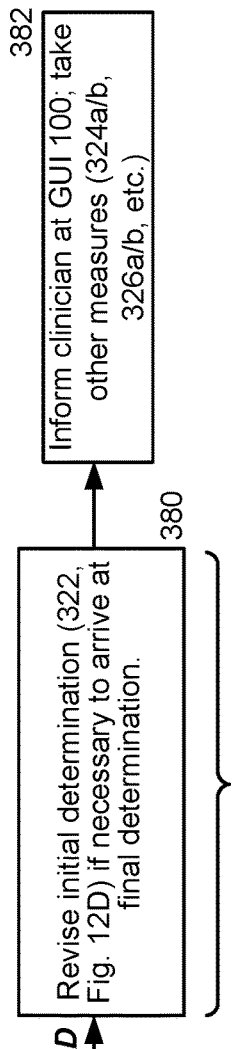

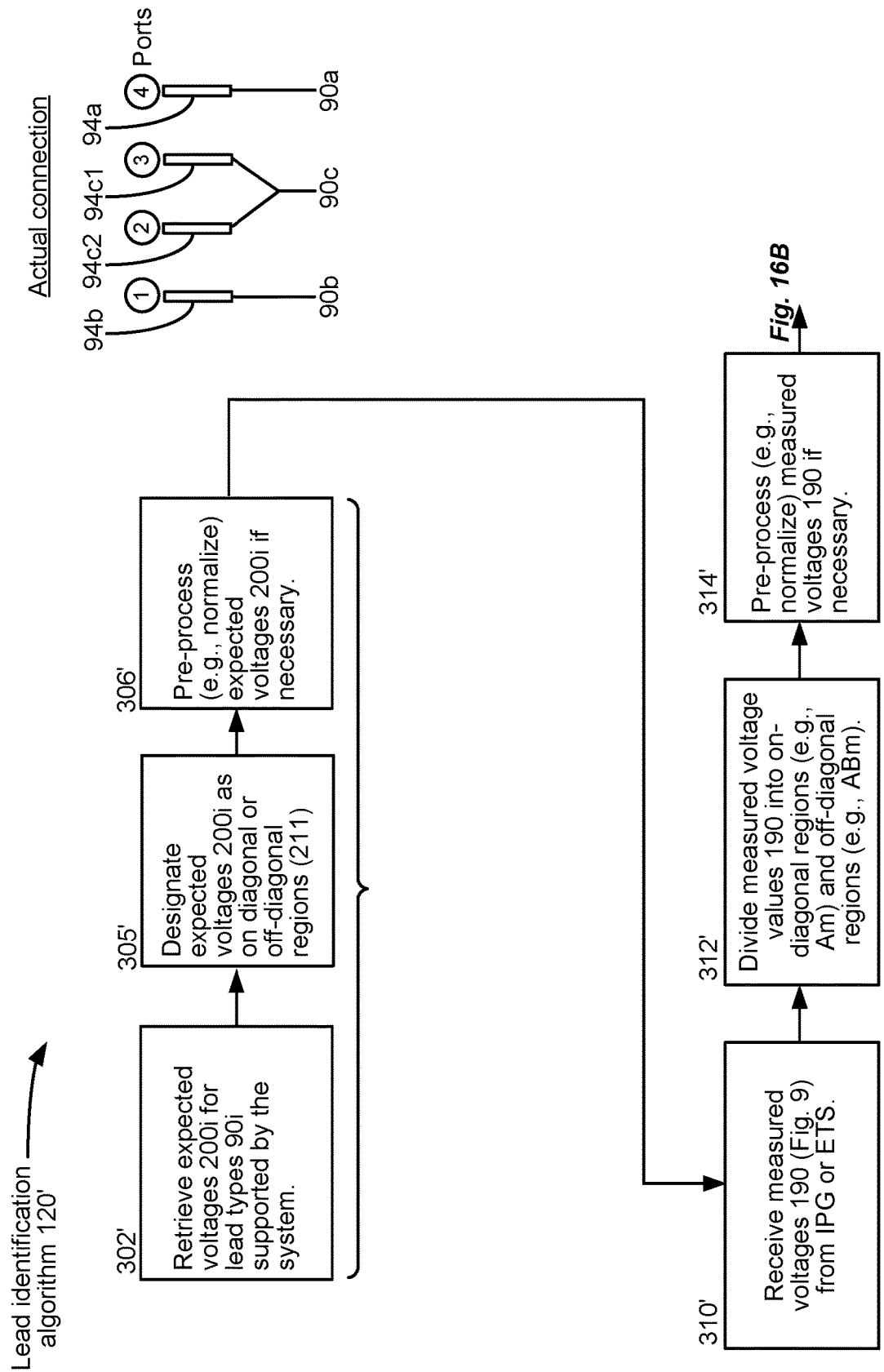

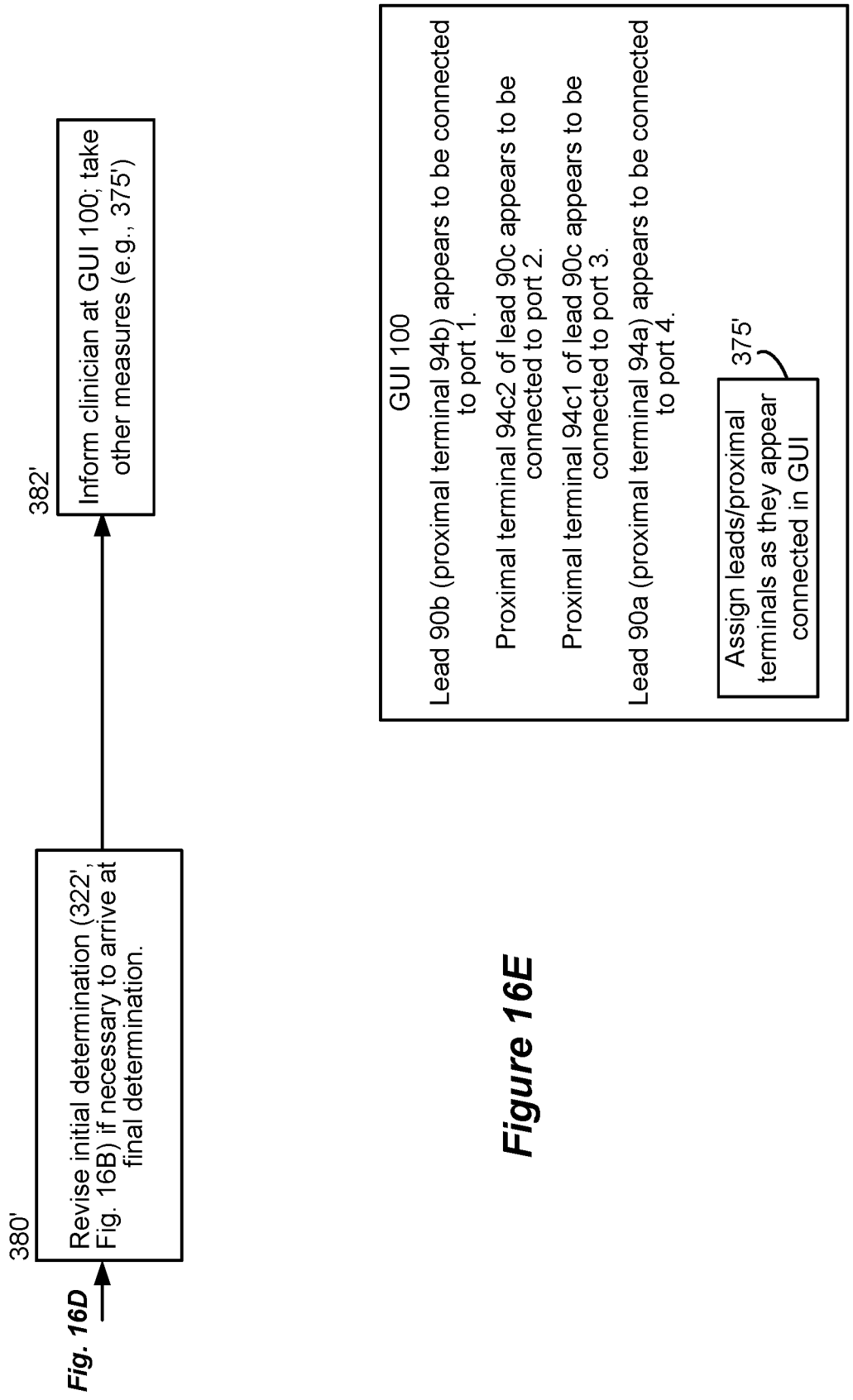

TECHNIQUES FOR SENSING INCORRECT LEAD CONNECTION TO AN IMPLANTABLE STIMULATOR DEVICE

CROSS-REFERENCE TO RELATED APPLICATIONS

This non-provisional application claims priority to U.S. Provisional Patent Application Serial Nos. 62/557,640, filed Sep. 12, 2017, and 62/568,111 filed Oct. 4, 2017, which are incorporated herein by reference in their entireties.

FIELD OF THE INVENTION

This application relates to implantable stimulator devices (ISD), and more specifically to devices and methods for determining which types of leads are connected to the ISD.

INTRODUCTION

Implantable stimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) or Spinal Cord Stimulation (SCS) system, such as that disclosed in U.S. Pat. No. 6,516,227 and U.S. Patent Application Publication 2016/0184591. However, the present invention may find applicability with any implantable neurostimulator device system.

A DBS or SCS system typically includes an Implantable Pulse Generator (IPG) 10 shown in FIG. 1A. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped electrodes 16 carried on a flexible body 18. In another example, a paddle lead (not shown) can provide electrodes 16 positioned in a two-dimensional array on one of its generally flat surfaces.

In yet another example shown in FIG. 1B, a percutaneous lead 33 can include one or more split-ring electrodes. In this example, eight electrodes 16 (E1-E8) are shown. Electrode E8 at the distal end of the lead and electrode E1 at a proximal end of the lead comprise ring electrodes spanning 360 degrees around a central axis of the lead 33. Electrodes E2, E3, and E4 comprise split-ring electrodes, each of which are located at the same longitudinal position along the central axis 31, but with each spanning less than 360 degrees around the axis. For example, each of electrodes E2, E3, and E4 may span 90 degrees around the axis 31, with each being separated from the others by gaps of 30 degrees. Electrodes E5, E6, and E7 also comprise split-ring electrodes, but are located at a different longitudinal position along the central axis 31 than are split-ring electrodes E1, E2, and E3. As shown, the split-ring electrodes E1-E3 and E5-E7 may be located at longitudinal positions along the axis 31 between ring-shaped electrodes E1 and E8.

Lead wires 20 within the leads are coupled to the electrodes 16 and to proximal contacts 21a of a proximal terminal 21 insertable into lead connectors 22 or "ports" fixed in a header 23 on the IPG 10, which header can comprise an epoxy for example. Once the proximal terminal 21 is inserted in a port, its proximal contacts 21a connect to device contacts 24 within the ports 22, which are in turn coupled by feedthrough pins 25 through a case feedthrough 26 to stimulation circuitry 28 within the case 12, which stimulation circuitry 28 is described below.

In the IPG 10 illustrated in FIG. 1A, there are thirty-two electrodes (E1-E32), split between four percutaneous leads 15, and thus the header 23 may include a 2×2 array of eight-electrode ports 22. However, the type and number of leads, and the number of electrodes, in an IPG is application specific and therefore can vary. The conductive case 12 can also comprise an electrode (Ec).

In a SCS application, as is useful to alleviate chronic back pain for example, the electrode lead(s) are typically implanted in the spinal column proximate to the dura in a patient's spinal cord, preferably spanning left and right of the patient's spinal column. The proximal terminals 21 are tunneled through the patient's tissue to a distant location such as the buttocks where the IPG case 12 is implanted, at which point they are coupled to the ports 22. In a DBS application, as is useful in the treatment of tremor in Parkinson's disease for example, the IPG 10 is typically implanted under the patient's clavicle (collarbone). Percutaneous leads 15 are tunneled through the neck and the scalp where the electrodes 16 are implanted through holes drilled in the skull and positioned for example in the subthalamic nucleus (STN) and the pedunculopontine nucleus (PPN) in each brain hemisphere. In other IPG examples designed for implantation directly at a site requiring stimulation, the IPG can be lead-less, having electrodes 16 instead appearing on the body of the IPG 10. The IPG lead(s) can be integrated with and permanently connected to the IPG 10 in other solutions.

IPG 10 can include one or more antennas 27a or 27b allowing it to communicate bi-directionally with a number of external devices discussed subsequently. Antenna 27a as shown comprises a conductive coil, and can communicate using near-field magnetic induction. Antenna 27b comprises an RF antenna, such as a patch, slot, or wire, and operable as a monopole or dipole. RF antenna 27b preferably communicates using far-field electromagnetic waves, and may operate in accordance with any number of known RF communication standards, such as Bluetooth, Zigbee, WiFi, MICS, and the like. Either of antennas 27a or 27b can appear in the header 23, in the case 12, or even outside of the IPG 10.

Stimulation in IPG 10 is typically provided by pulses, as shown in the example of FIG. 2. Stimulation parameters typically include amplitude (current I, although a voltage amplitude V can also be used); frequency (f); pulse width (PW) of the pulses or of its individual phases such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient. The stimulation pulses as shown are biphasic, with each pulse comprising a first phase 30a followed thereafter by a second phase 30b of opposite polarity. Biphasic pulses are useful to actively recover any charge that might be stored on capacitive elements in the electrode current paths, such as on the DC-blocking capacitors 38 (FIG. 3).

In the example of FIG. 2, electrode E1 has been selected as a cathode (during its first phase 30a), and thus provides pulses which sink a negative current of amplitude −I from the tissue. Electrode E2 has been selected as an anode (again during first phase 30a), and thus provides pulses which source a corresponding positive current of amplitude +I from the tissue. The polarity of the currents at these electrodes can be changed: for example, E2 can be selected as a cathode, and E1 can be selected as an anode, such as occurs during the second pulse phase 30b.

IPG 10 as mentioned includes stimulation circuitry 28 to form prescribed stimulation at a patient's tissue. FIG. 3 shows an example of stimulation circuitry 28, which includes one or more current sources 40, and one or more current sinks $42_k$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39, although the NDACs and PDACs can also be shared between the electrodes using switch matrices in other examples. Each electrode node ei 39 is connected to an electrode Ei 16 via a DC-blocking capacitor Ci 38, which as is well known is useful as a safety measure to prevent DC-current injection into the tissue, as can occur if there is a fault in the stimulation circuitry 28. PDACs $40_i$ and NDACs $42_i$ can also comprise voltage sources. Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), which may also contain other circuitry useful in the IPG 10, such as telemetry circuitry (for interfacing off chip with telemetry antennas 27a and/or 27b), etc.

Proper control of the PDACs $40_i$ and NDACs $42_i$ allows any of the electrodes 16 and the case electrode Ec 12 to act as anodes or cathodes to create a current through a patient's tissue, R, hopefully with good therapeutic effect. In the example shown, and consistent with the first pulse phase 30a of FIG. 2, electrode E1 has been selected as a cathode electrode to sink current from the tissue R and electrode E2 has been selected as an anode electrode to source current to the tissue R.

FIG. 4 shows an external trial stimulation environment that may precede implantation of an IPG 10 in a patient, particularly in an SCS application. During external trial stimulation, stimulation can be tried on a prospective implant patient without going so far as to implant the IPG 10. Instead, a trial electrode array 17' (e.g., one or more trial leads such as those described earlier) are implanted in the patient's tissue at a target location 52, such as within the spinal column as explained earlier. The proximal ends of the leads exit an incision 54 in the patient's tissue and are coupled to an External Trial Stimulator (ETS) 50. Generally, such coupling is affected by use of an intermediate extender cable 61, which include a receptacle 55 on its distal end and a plug 57 on its proximal end. The receptacle 55 of the extender cable 61 is built similarly to the port 22 included in the IPG 10 and receives the proximal terminals 21' of the trial leads. The plug 57 of each extender cable 61 couples to a port 59 of the ETS 50. The number of ports can vary, but in FIG. 4 four ports are shown.

The ETS 50 generally mimics operation of the IPG 10, and thus can provide stimulation to the patient's tissue as explained above. Although not shown, the ETS 50 would include stimulation circuitry similar or identical to the stimulation circuitry 28 in the IPG 10 (FIG. 3). The ETS 50 is generally worn externally by the patient for a short while (e.g., two weeks), which allows the patient and his clinician to experiment with different stimulation parameters to hopefully find a stimulation program that alleviates the patient's symptoms. If external trial stimulation proves successful, the trial leads are explanted, and a full IPG 10 and a permanent leads are implanted as described above; if unsuccessful, the trial leads are simply explanted.

Like the IPG 10, the ETS 50 can include one or more antennas to enable bi-directional communications with external devices such as those shown in FIG. 5. Such antennas can include a near-field magnetic-induction coil antenna 56a, and/or a far-field RF antenna 56b, as described earlier. ETS 50, being external to the patient, can also communicate with external devices by a cable. ETS 50 may also include a battery (not shown) for operational power.

FIG. 5 shows various external devices that can wirelessly communicate data with the IPG 10 or ETS 50, including a patient, hand-held external controller 60, and a clinician programmer 70. Both of devices 60 and 70 can be used to wirelessly transmit a stimulation program to the IPG 10 or ETS 50—that is, to program their stimulation circuitries to produce stimulation with a desired amplitude and timing described earlier. Both devices 60 and 70 may also be used to adjust one or more stimulation parameters of a stimulation program that the IPG 10 or ETS 50 is currently executing. Devices 60 and 70 may also wirelessly receive information from the IPG 10 or ETS 50, such as various status information, etc.

External controller 60 can be as described in U.S. Patent Application Publication 2015/0080982 for example, and may comprise a controller dedicated to work with the IPG 10 or ETS 50. External controller 60 may also comprise a general purpose mobile electronics device such as a mobile phone which has been programmed with a Medical Device Application (MDA) allowing it to work as a wireless controller for the IPG 10 or ETS 50, as described in U.S. Patent Application Publication 2015/0231402. The external controller 60 can have one or more antennas capable of communicating with a corresponding antenna the IPG 10 or ETS 50, such as a near-field magnetic-induction coil antenna 64a or a far-field RF antenna 64b.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

Like the external controller 60, the clinician programmer 70 can have one or more antennas capable of communicating with a corresponding antenna the IPG 10 or ETS 50. For example, wand 76 can likewise include a coil antenna 80a to establish near-field magnetic-induction communications at small distances. The wand 76, the computing device 72, or both, can likewise include an RF antenna 80*b* to establish communication at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer graphical user interface (GUI) provided on the display 74 of the computing device 72. As one skilled in the art understands, the GUI can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. For example, control circuitry 88 can comprise an i5 processor manufactured by Intel Corp, as described at https://www.intel.com/content/www/us/en/products/processors/core/i5-processors.html. Such control circuitry 88, in addition to executing the clinician programmer software 84 and rendering the GUI, can also enable communications via antennas 80*a* or 80*b* to communicate stimulation parameters chosen through the GUI to the patient's IPG 10 or ETS 50.

The user interface of the external controller 60 may provide similar functionality because the external controller 60 can include the same or similar hardware and software programming as the clinician programmer 70. For example, the external controller 60 includes control circuitry 66 similar to the control circuitry 88 in the clinician programmer 70, and may similarly be programmed with external controller software stored in device memory.

SUMMARY

A system is disclosed for identifying one or more leads connected to one or more ports of an implantable stimulator device (ISD), wherein the ISD comprises a plurality I of ports, each port comprising a plurality of J device contacts coupleable to electrodes corresponding to that port, wherein the ISD supports N=J*I electrodes. The system may comprise: an ISD to which one or more leads are connected, wherein each lead has a distal end comprising at least J electrodes and one or more proximal terminals, wherein the one or more proximal terminals for each lead comprises proximal contacts with each proximal contact connected to one of the at least J electrodes, wherein each of the one or more proximal terminals for each lead is connected to one of the ports of the ISD, wherein the ISD is configured to provide stimulation at each of the N electrodes, and measure a parameter at each of the N electrodes in response to the stimulation of each of the N electrodes. The system may further comprise an external device in communication with the ISD, wherein the external device is configured to receive the measured parameters, retrieve expected parameters for a plurality of leads types useable by the ISD, and compare in the external device at least some of the measured parameters to the expected parameters to determine whether each of the one or more connected leads comprises a lead with one proximal terminal or a lead with a plurality of proximal terminals.

The external device may be configured to compare the at least some of the measured parameters to the expected parameters by establishing at least one correlation coefficient between the at least some of the measured parameters and the expected parameters.

The ISD may be configured to stimulate each of the N electrodes using a constant current. The IPG may comprises a case electrode, and the ISD may be configured to provide the constant current between each of the N electrodes and the case electrode. The parameter measured at each of the N electrodes may comprise a voltage.

The external device may be further configured to: for each connected lead determined to have only one proximal terminal, determine that lead's type and the port of the ISD to which its proximal terminal is connected; and for each connected lead determined to have a plurality of proximal terminals, determine that lead's type and the ports of the ISD to which their plurality of proximal terminals are connected.

The external device may be further configured to divide the measured parameters into first regions and second regions. Each first region may correspond to one of the ports and comprise measured parameters when the J electrodes corresponding to that port are stimulated and measured. Each second region may comprise measured parameters when the J electrodes corresponding to a given port are stimulated and when the J electrodes corresponding to a different port are measured.

If one of the plurality of lead types useable by the ISD comprises a lead having J electrodes and one proximal terminal, the retrieved expected parameters for that lead type may comprise a third region of expected parameters. If one of the plurality of lead types useable by the ISD comprises a lead having at least J electrodes and more than one proximal terminal, the retrieved expected parameters for that lead type may comprise fourth regions of expected parameters and fifth regions of expected parameters. Each fourth region may comprise expected parameters when J electrodes corresponding to one of the proximal terminals are stimulated and measured. Each fifth region may comprise expected parameters when J electrodes corresponding to one of the proximal terminals are stimulated and when J electrodes corresponding to a different one of the proximal terminals are measured.

The external device may be configured to determine which of the second regions are significant second regions having significant values for its measured parameters. The external device may be configured to compare the significant second regions to the fifth regions to determine if a connected lead comprises a plurality of proximal terminals, and which ports of the ISD its plurality of proximal terminals are connected. The external device may be configured to compare at least some of the first regions and significant second regions to the fourth regions and the fifth regions to determine, for each lead determined to have a plurality of proximal terminals, that lead's type and the ports of the ISD to which its proximal terminals are connected. The external device may be configured to compare the first regions to the third regions to determine, for each lead determined to have only one proximal terminal, that lead's type and the port of the ISD to which its proximal terminal is connected.

The external device may be further configured to indicate each determined connected lead type and the port to which each proximal terminal of each connected lead type is connected. The external device may be further configured to allow a user to assign the connection of proximal terminals of one or more of the plurality of lead types to one or more of the plurality of ports of the ISD. The external device may be further configured to determine whether the determined lead types and the determined connection of those lead types' proximal terminals to particular ports of the ISD matches the assigned connections. The external device may be further configured to, if the determined lead types and the determined connection of those lead types' proximal terminals to particular ports don't match the assigned connections, notify the user of the mismatch. The external device may be further configured to, if there is a mismatch, provide an option to reassign the connections to match the determined lead types and determined connection of those lead types' proximal terminals to particular ports of the ISD.

A method is disclosed for identifying one or more leads connected to one or more ports of an implantable stimulator device (ISD), wherein the ISD comprises a plurality I of ports, each port comprising a plurality of J device contacts coupleable to electrodes corresponding to that port, wherein the ISD supports N=J*I electrodes. The method may comprise: (a) connecting one or more leads to the ISD, wherein each lead has a distal end comprising at least J electrodes and one or more proximal terminals, wherein the one or more proximal terminals for each lead comprises proximal contacts with each proximal contact connected to one of the at least J electrodes, wherein each of the one or more proximal terminals for each lead is connected to one of the ports of the ISD; (b) providing stimulation at each of the N electrodes; (c) measuring a parameter at each of the N electrodes in response to the stimulation of each of the N electrodes and receiving the measured parameters at an external device in communication with the ISD; (d) retrieving at the external device expected parameters for a plurality of leads types useable by the ISD; and (e) comparing in the external device at least some of the measured parameters to the expected parameters to determine whether each of the one or more connected leads comprises a lead with one proximal terminal or a lead with a plurality of proximal terminals.

The comparison in step (e) may comprise establishing at least one correlation coefficient between the at least some of the measured parameters and the expected parameters.

Step (b) may comprise stimulating each of the N electrodes using a constant current. The ISD may comprise a case electrode, and the constant current may be provided between each of the N electrodes and the case electrode. Step (c) may comprise measuring a voltage as the parameter at each of the N electrodes.

Step (e) may further comprise: for each connected lead determined to have only one proximal terminal, determine that lead's type and the port of the ISD to which its proximal terminal is connected; and for each connected lead determined to have a plurality of proximal terminals, determine that lead's type and the ports of the ISD to which their plurality of proximal terminals are connected.

Step (e) may further comprise dividing the measured parameters into first regions and second regions. Each first region may correspond to one of the ports and comprises measured parameters when the J electrodes corresponding to that port are stimulated and measured. Each second region may comprise measured parameters when the J electrodes corresponding to a given port are stimulated and when the J electrodes corresponding to a different port are measured.

If one of the plurality of lead types useable by the ISD comprises a lead having J electrodes and one proximal terminal, the retrieved expected parameters for that lead type may comprise a third region of expected parameters. If one of the plurality of lead types useable by the ISD comprises a lead having at least J electrodes and more than one proximal terminal, the retrieved expected parameters for that lead type may comprise fourth regions of expected parameters and fifth regions of expected parameters. Each fourth region may comprise expected parameters when J electrodes corresponding to one of the proximal terminals are stimulated and measured. Each fifth region may comprise expected parameters when J electrodes corresponding to one of the proximal terminals are stimulated and when J electrodes corresponding to a different one of the proximal terminals are measured.

The method may further comprise determining which of the second regions are significant second regions having significant values for its measured parameters. In step (e) the significant second regions may be compared to the fifth regions to determine if a connected lead comprises a plurality of proximal terminals, and which ports of the ISD its plurality of proximal terminals are connected. In step (e) the first regions and significant second regions may be compared to the fourth regions and the fifth regions to determine, for each lead determined to have a plurality of proximal terminals, that lead's type and the ports of the ISD to which its proximal terminals are connected. In step (e) the first regions may be compared to the third regions to determine, for each lead determined to have only one proximal terminal, that lead's type and the port of the ISD to which its proximal terminal is connected.

The method may further comprise after step (e): indicating on the external device each determined connected lead type and an indication of the port to which each proximal terminal of each connected lead type is connected.

The method may further comprise prior to step (a): assigning at the external device the connection of proximal terminals of one or more of the plurality of lead types to one or more of the plurality of ports of the ISD. The method may further comprise after step (e): (f) determining at the external device whether the determined lead types and the determined connection of those lead types' proximal terminals to particular ports of the ISD in step (e) matches the assigned connections. The method may further comprise: (g) if the determined lead types and the determined connection of those lead types' proximal terminals to particular ports don't match the assigned connections, notifying a user of the external device of the mismatch. If in step (g) there is a mismatch, the method may further comprise providing an option on the external device to reassign the connections to match the determined lead types and determined connection of those lead types' proximal terminals to particular ports of the ISD.

A non-transitory computer readable medium is disclosed which is executable on an external device configured to communicate with an implantable stimulator device (ISD), wherein the ISD comprises a plurality I of ports, each port comprising a plurality of J device contacts coupleable to electrodes corresponding to that port, wherein the ISD supports N=J*I electrodes, wherein the medium includes instructions that when executed on the external device cause the external device to: (a) instruct the ISD to provide stimulation at each of the N electrodes, wherein there are one or more leads connected to the ISD, wherein each lead has a distal end comprising at least J electrodes and one or more proximal terminals, wherein the one or more proximal terminals for each lead comprises proximal contacts with each proximal contact connected to one of the at least J electrodes, wherein each of the one or more proximal terminals for each lead is connected to one of the ports of the ISD; (b) receive measured parameters from the ISD, wherein the measured parameters comprise a parameter measured at each of the N electrodes in response to the stimulation of each of the N electrodes; (c) retrieve from the external device expected parameters for a plurality of leads types useable by the ISD; and (d) compare in the external device at least some of the measured parameters to the expected parameters to determine whether each of the one or more connected leads comprises a lead with one proximal terminal or a lead with a plurality of proximal terminals.

A system is disclosed for identifying one or more leads connected to one or more ports of an implantable stimulator device (ISD), wherein the ISD comprises a plurality I of ports, each port comprising a plurality of J device contacts coupleable to electrodes corresponding to that port. The system may comprise: an ISD to which one or more leads are connected, wherein each lead has a distal end comprising at least J electrodes and one or more proximal terminals, wherein the one or more proximal terminals for each lead comprises proximal contacts with each proximal contact connected to one of the at least J electrodes, wherein each of the one or more proximal terminals for each lead is connected to one of the ports of the ISD, wherein the ISD is configured to provide stimulation at each of the electrodes, and measure a parameter at some or all of the electrodes in response to the stimulation of each of the electrodes. The system may further comprise an external device in communication with the ISD, wherein the external device may be configured to divide the measured parameters into: first regions, wherein each first region comprises measurements when the stimulated electrodes and the measured electrodes correspond to electrodes corresponding to a particular one of the ports of the ETS or IPG, and second regions, wherein each second region comprises measurements when the stimulated electrodes correspond to electrodes corresponding to a particular one of the ports of the ETS or IPG and when the measured electrodes correspond to a different one of the ports of the ISD; receive expected parameters for a plurality of lead types useable by the ISD, wherein the expected parameters for lead types having only one proximal terminal comprise third regions, and wherein the expected parameters for lead types having a plurality of proximal terminal comprise fourth regions and fifth regions, wherein each fourth region comprises expected parameters when electrodes corresponding to one of the proximal terminals are stimulated and measured, and wherein each fifth region comprises expected parameters when electrodes corresponding to one of the proximal terminals are stimulated and when electrodes corresponding to a different one of the proximal terminals are measured, and compare at least some of the first regions with the third and fourth regions, and compare at least some of the second regions with the fifth regions, to determine which proximal terminals of which of the lead types are connected to the ports of the ISD.

The external device may be configured to establish at least one correlation coefficient between the at least some of the first regions and the third and fourth regions, and to establish at least at least one correlation coefficient between the at least some of the second regions and the fifth regions.

The ISD may configured to stimulate each of the electrodes using a constant current. The IPG may comprise a case electrode, and wherein the constant current is provided between each of the electrodes and the case electrode. The parameter measured at some or all of the electrodes may comprise a voltage.

The external device may be configured to determine which of the second regions are significant second regions having significant values for its measured parameters. The external device may be configured to, for each lead type having a plurality of proximal terminals, compare the significant second regions to the fifth regions, and compare the at least some of the first regions to the fourth regions, to determine the ports of the ISD to which their proximal terminals are connected. The external device may be configured to, for each lead type having only one proximal terminal, compare the at least some of the first regions to the third regions to determine the port of the ISD to which its proximal terminal is connected.

The external device may be configured to indicate each determined connected lead type and the port to which each proximal terminal of each connected lead type is connected. The external device may be configured to allow a user to assign the connection of proximal terminals of one or more of the plurality of lead types to one or more of the plurality of ports of the ISD. The external device may be configured to determine whether the determined lead types and the determined connection of those lead types' proximal terminals to particular ports of the ISD matches the assigned connections. The external device may be configured to, if the determined lead types and the determined connection of those lead types' proximal terminals to particular ports don't match the assigned connections, notify the user of the mismatch. The external device may be further configured to, if there is a mismatch, provide an option to reassign the connections to match the determined lead types and determined connection of those lead types' proximal terminals to particular ports of the ISD.

A method is disclosed for identifying one or more leads connected to one or more ports of an implantable stimulator device (ISD), wherein the ISD comprises a plurality I of ports, each port comprising a plurality of J device contacts coupleable to electrodes corresponding to that port. The method may comprise: (a) connecting one or more leads to the ISD, wherein each lead has a distal end comprising at least J electrodes and one or more proximal terminals, wherein the one or more proximal terminals for each lead comprises proximal contacts with each proximal contact connected to one of the at least J electrodes, wherein each of the one or more proximal terminals for each lead is connected to one of the ports of the ISD; (b) providing stimulation at each of the electrodes; (c) measuring a parameter at some or all of the electrodes in response to the stimulation of each of the electrodes and receiving the measured parameters at an external device in communication with the ISD; (d) dividing at the external device the measured parameters into: first regions, wherein each first region comprises measurements when the stimulated electrodes and the measured electrodes correspond to electrodes corresponding to a particular one of the ports of the ETS or IPG, and second regions, wherein each second region comprises measurements when the stimulated electrodes correspond to electrodes corresponding to a particular one of the ports of the ETS or IPG and when the measured electrodes correspond to a different one of the ports of the ISD; (e) retrieving at the external device expected parameters for a plurality of lead types useable by the ISD, wherein the expected parameters for lead types having only one proximal terminal comprise third regions, and wherein the expected parameters for lead types having a plurality of proximal terminal comprise fourth regions and fifth regions, wherein each fourth region comprises expected parameters when electrodes corresponding to one of the proximal terminals are stimulated and measured, and wherein each fifth region comprises expected parameters when electrodes corresponding to one of the proximal terminals are stimulated and when electrodes corresponding to a different one of the proximal terminals are measured, (f) comparing at the external device at least some of the first regions with the third and fourth regions, and comparing at least some of the second regions with the fifth regions, to determine which proximal terminals of which of the lead types are connected to the ports of the ISD.

The comparison in step (f) may comprise establishing at least one correlation coefficient between the first regions and the third and fourth regions, and establishing at least at least one correlation coefficient between the second regions and the fifth regions.

Step (b) may comprise stimulating each of the electrodes using a constant current. The IPG may comprise a case electrode, and the constant current may be provided between each of the electrodes and the case electrode. Step (c) may comprise measuring a voltage as the parameter at some or all of the electrodes.

Step (d) may further comprise determining which of the second regions are significant second regions having significant values for its measured parameters. In step (f), for each lead type having a plurality of proximal terminals, the significant second regions may be compared to the fifth regions, and the first regions may be compared to the fourth regions, to determine the ports of the ISD to which their proximal terminals are connected. In step (f), for each lead type having only one proximal terminal, the first regions may be compared to the third regions to determine the port of the ISD to which its proximal terminal is connected.

The method may further comprise after step (f): indicating on the external device each determined connected lead type and an indication of the port to which each proximal terminal of each connected lead type is connected.

The method may further comprise prior to step (a): assigning at the external device the connection of proximal terminals of one or more of the plurality of lead types to one or more of the plurality of ports of the ISD. The method may further comprise after step (f): (g) determining at the external device whether the determined lead types and the determined connection of those lead types' proximal terminals to particular ports of the ISD in step (f) matches the assigned connections. The method may further comprise: (h) if the determined lead types and the determined connection of those lead types' proximal terminals to particular ports don't match the assigned connections, notifying a user of the external device of the mismatch. If in step (h) there is a mismatch, the method may further comprise providing an option on the external device to reassign the connections to match the determined lead types and determined connection of those lead types' proximal terminals to particular ports of the ISD.

A non-transitory computer readable medium is disclosed that is executable on an external device configured to communicate with an implantable stimulator device (ISD), wherein the ISD comprises a plurality I of ports, each port comprising a plurality of J device contacts coupleable to electrodes corresponding to that port, wherein the medium includes instructions that when executed on the external device cause the external device to: (a) instruct the ISD to provide stimulation at each of the N electrodes, wherein there are one or more leads connected to the ISD, wherein each lead has a distal end comprising at least J electrodes and one or more proximal terminals, wherein the one or more proximal terminals for each lead comprises proximal contacts with each proximal contact connected to one of the at least J electrodes, wherein each of the one or more proximal terminals for each lead is connected to one of the ports of the ISD; (b) receive measured parameters from the ISD, wherein the measured parameters comprise a parameter measured at some or all of the of the electrodes in response to the stimulation of each of the electrodes; (c) retrieve from the external device expected parameters for a plurality of lead types useable by the ISD, wherein the expected parameters for lead types having only one proximal terminal comprise third regions, and wherein the expected parameters for lead types having a plurality of proximal terminal comprise fourth regions and fifth regions, wherein each fourth region comprises expected parameters when electrodes corresponding to one of the proximal terminals are stimulated and measured, and wherein each fifth region comprises expected parameters when electrodes corresponding to one of the proximal terminals are stimulated and when electrodes corresponding to a different one of the proximal terminals are measured, (c) compare at the external device at least some of the first regions with the third and fourth regions, and comparing at least some of the second regions with the fifth regions, to determine which proximal terminals of which of the lead types are connected to the ports of the ISD.

BRIEF DESCRIPTION OF THE DRAWINGS

FIG. 4 shows an ETS environment useable to provide stimulation before implantation of an IPG, in accordance with the prior art.

FIG. 5 shows various external devices capable of communicating with and programming stimulation in an IPG or ETS, in accordance with the prior art.

FIGS. 8A and 8B respectively show two different connections of proximal terminals of the leads, which are in the example consistent and not consistent with the manner in which the proximal terminal are assigned in the GUI.

FIGS. 10A-10D show expected voltages for various lead types usable with the lead identification algorithm.

FIGS. 12A-12F show operation of the lead identification algorithm using analysis of only the on-diagonal regions.

FIGS. 14A-14F show continuing operation of the lead identification algorithm using analysis of off-diagonal regions.

FIGS. 16A-16E show an alternative embodiment of the lead identification algorithm for detecting leads connected to an IPG or ETS in which the leads (or their proximal terminals) are not preassigned to particular ports of the IPG or ETS.

DETAILED DESCRIPTION

Figure 1A:
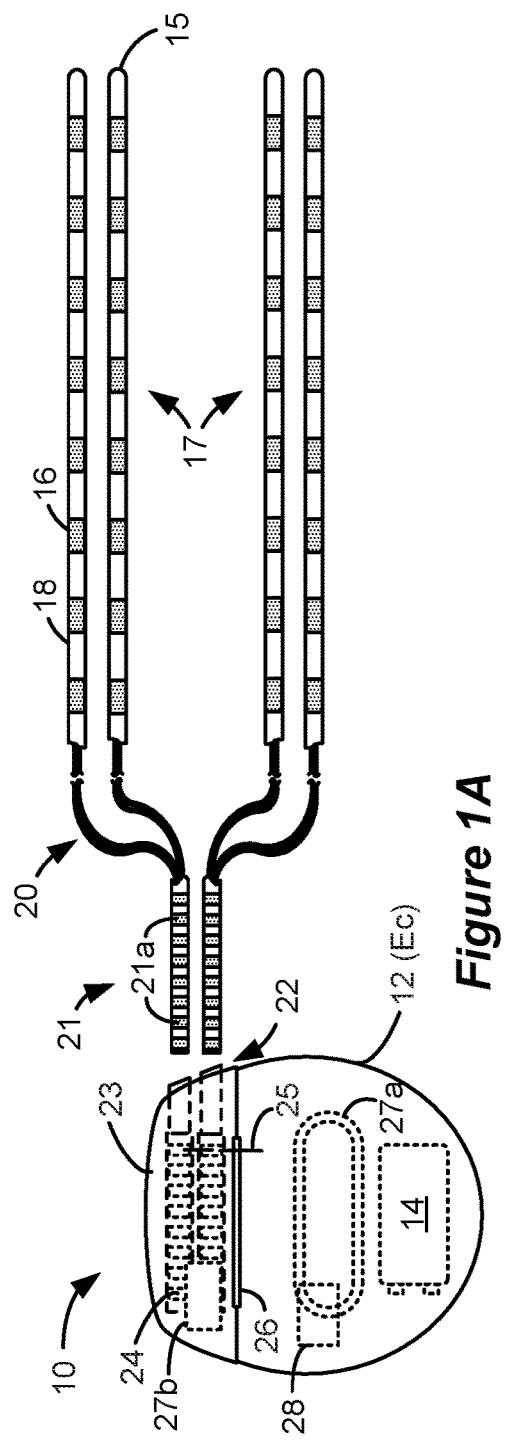
FIG. 1A shows an Implantable Pulse Generator (IPG), in accordance with the prior art.
Figure 1B:
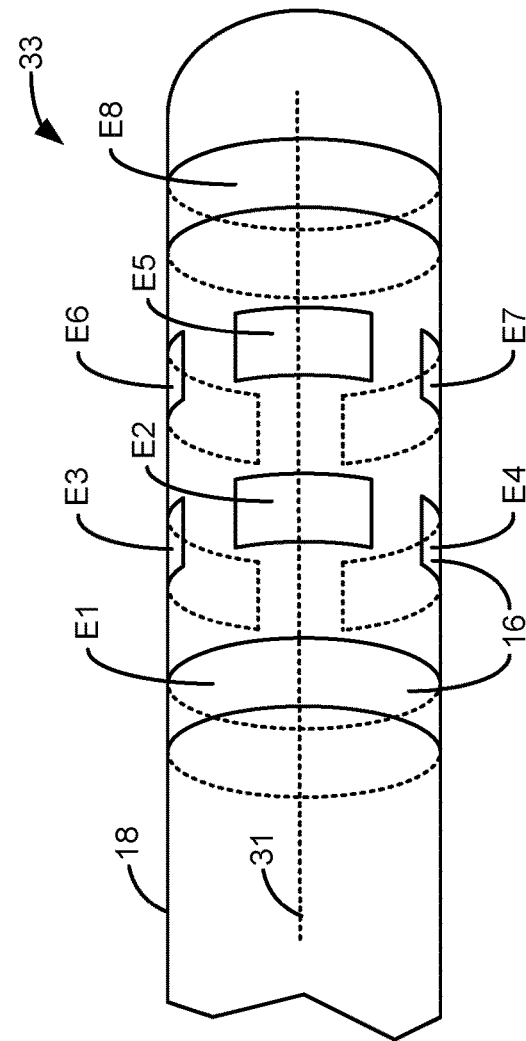
FIG. 1B shows a percutaneous lead having split-ring electrodes, in accordance with the prior art.
Figure 2:
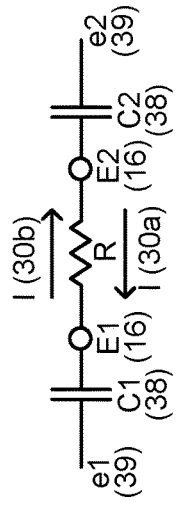
FIG. 2 shows an example of stimulation pulses (waveforms) producible by the IPG or by an External Trial Stimulator (ETS), in accordance with the prior art.
Figure 2:
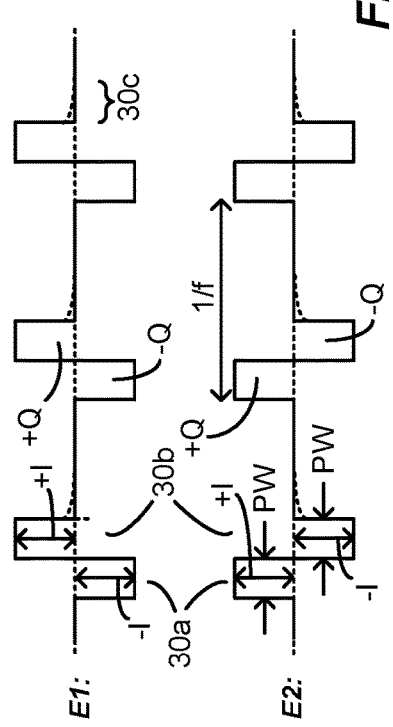
Figure 6:
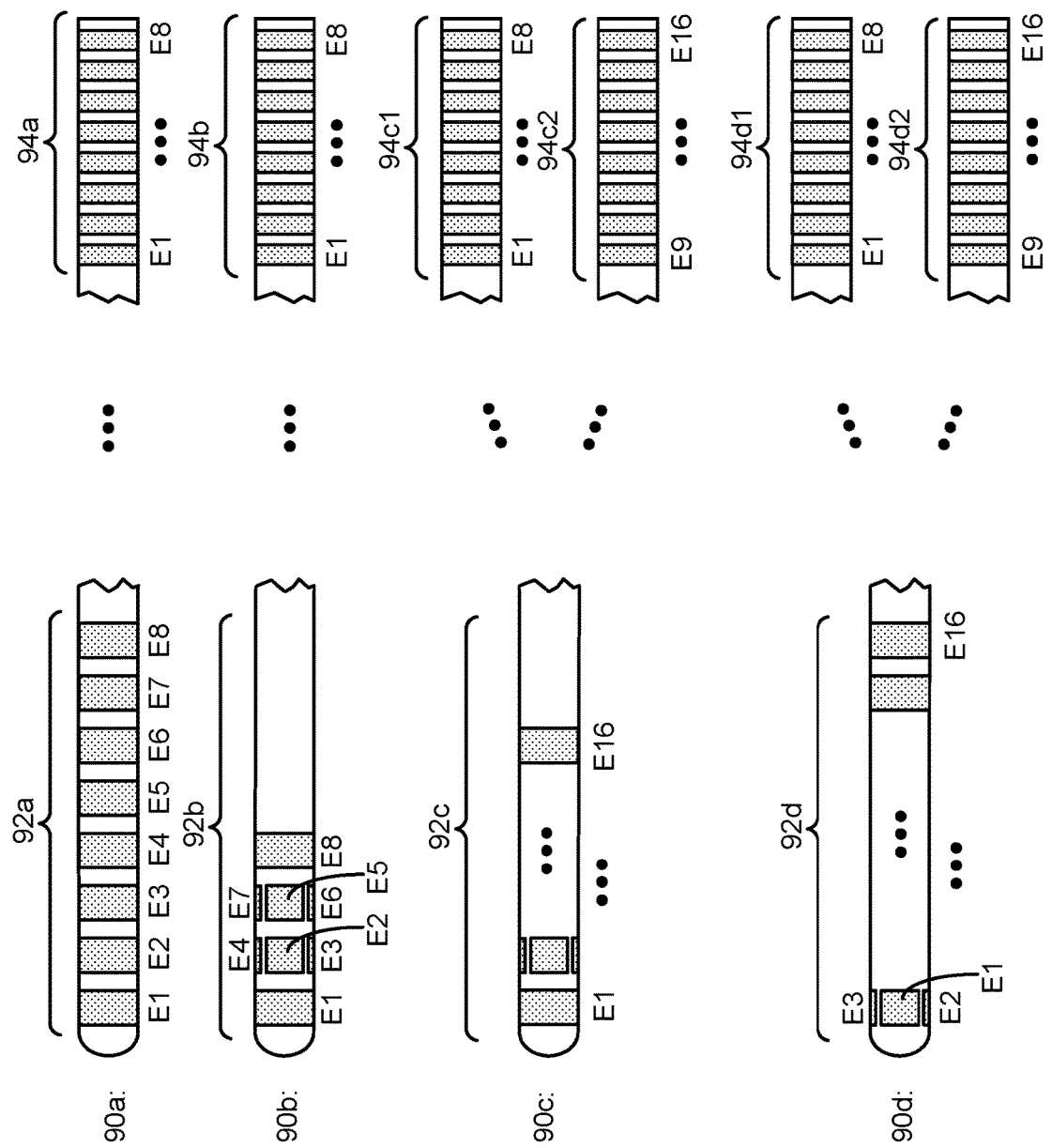
FIG. 6 shows various types of leads useable in the disclosed system and coupleable to ports of an IPG or ETS, including eight-electrode leads having a single eight-electrode proximal terminal, and sixteen-electrode leads having two eight-electrode proximal terminals.

FIG. 6 shows different types of leads or trial leads that can be used with an IPG or ETS (ISDs more generally). Lead 90a for example comprises a distal end 92a having eight ring-shaped electrodes E1-E8 placed at different longitudinal positions relative to a central axis (not shown in FIG. 6, but see FIG. 1B). Lead 90a includes an eight-electrode proximal terminal 94a—i.e., a proximal terminal having eight proximal contacts—which is insertable into any one of the eight-electrode ports 22 of an IPG (FIG. 1A).

Lead 90b is similar to the lead 33 described earlier (FIG. 1B), and has a mixture of ring-shaped electrodes (E1 and E8) and split-ring electrodes (E2/E3/E4 and E5/E6/E7) at its distal end 92b, with the split-ring electrodes at longitudinal positions between the ring-shaped electrodes. However, the longitudinal positions of the split-ring and ring-shaped electrodes can be freely varied along lead 90b. Like lead 90a, lead 90b includes an eight-electrode proximal terminal 94b which is insertable into any one of the eight-electrode ports 22.

Lead 90c comprises a distal end 92c having sixteen electrodes E1-E16, and again has a particular positioning of various types of electrodes, some of which may be ring-shaped, or split-ring, or which may have different areas. Because lead 90c has sixteen-electrodes, it terminates at two eight-electrode proximal terminals 94c1 and 94c2, each of which will fit into the eight-electrode ports 22 of the IPG or the eight-electrode receptacles 55 of the extender cables 61.

Lead 90d comprises a distal end 92d having sixteen electrodes E1-E16, and again has a particular positioning of various types of electrodes which is different from lead 90c. As with lead 90c, lead 90d terminates at two eight-electrode proximal terminals 94d1 and 94d2.

Any of leads 90a-90d could also comprise paddle leads having different numbers of electrodes and number of proximal terminals. Paddle leads are described further in U.S. Patent Application Publication 2017/0281958.

Further, when used in an ETS context, (trial) leads 90a-90d can be understood as inclusive of any extender cables 61 (FIG. 4). For example, an extender cable 61 when used as part of eight-electrode lead 90a will terminate in an eight-electrode plug 57 coupleable to a port 59 on the ETS, which plug comprises the proximal terminal 94a. For larger leads having sixteen electrodes such as leads 90c and 90d, the extender cable 61 may terminate in two eight-electrode proximal terminals (plugs 57) coupleable to two ports 59 on the ETS.

Note that leads 90a-90d are just examples of different types of leads that can be used with the IPG and ETS described herein, and other examples are possible.

Figure 7:
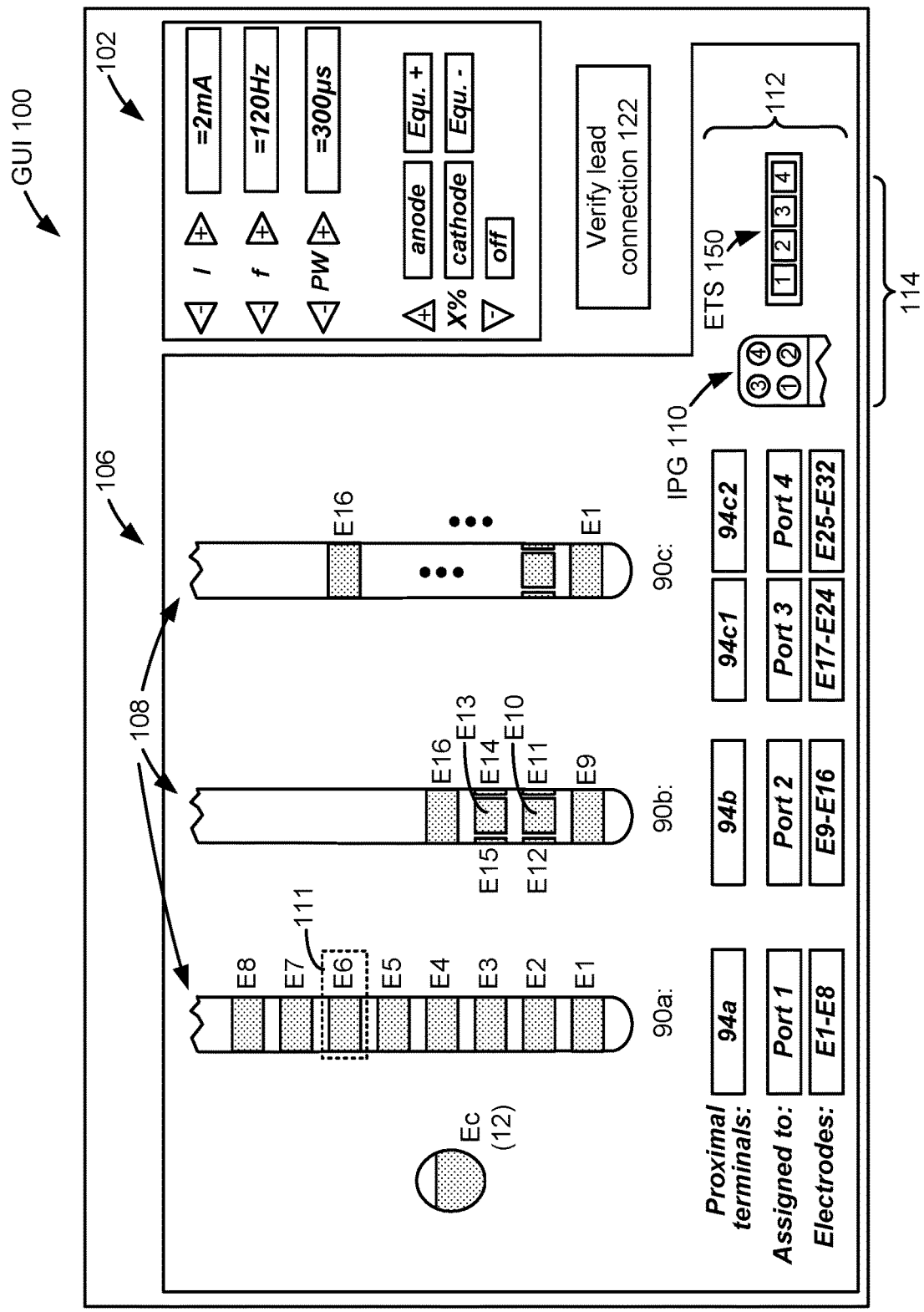
FIG. 7 shows a Graphical User Interface (GUI) for an external device such as a clinician programmer that can communicate with an IPG or ETS, and shows assignment of various leads (or proximal terminals) to various IPG or ETS ports.

FIG. 7 shows a Graphical User Interface (GUI) 100 that can be used to set stimulation programs or parameters that an IPG or ETS can execute, as described earlier. Additionally, GUI 100 may also be used to assign any of the leads 90a-90d to particular ones of the IPG's ports 22, or to assign any of the trial leads 90a-90d (inclusive of their extender cables 61 and proximal terminal plugs 57) to particular ones of the ETS's ports 59.

GUI 100 is operable in an external device capable of communicating with and IPG or ETS, and it is assumed in the description that follows that GUI 100 is operable in a clinician programmer 170 (FIG. 9), which may be used during surgical implantation of the IPG or the trial leads in an ETS, or after implantation when a therapeutically useful stimulation program is being chosen for a patient. However, GUI 100 could be rendered on a patient external programmer 160 (FIG. 9) or any other external device capable of communicating with IPG or ETS.

GUI 100 allows a clinician (or patient) to select the stimulation program that the IPG or ETS will provide. In this regard, the GUI 100 may include a stimulation parameter interface 102 where various aspects of the stimulation program can be selected or adjusted. For example, interface 102 allows a user to select the amplitude (e.g., a current I) for stimulation; the frequency (f) of stimulation pulses; and the pulse width (PW) of the stimulation pulses. Stimulation parameter interface 102 can however be significantly more complicated, and can allow many other stimulation parameters to be adjusted.

Stimulation parameter interface 102 may further allow a user to select the active electrodes—i.e., the electrodes that will receive the prescribed pulses. Selection of the active electrodes can occur in conjunction with a leads interface 106, which can include images 108 of the one or more leads or trial leads that have been or will be implanted in the patient. Although not shown, the leads interface 106 can include a selection to access a library of relevant images 108 of the types of leads that may be implanted in different patients and that are supported by the system. Although not shown, lead images 108 can also be shown in relative position to each other in the patient's tissue, and leads interface 106 may further illustrate the relative position of each of the leads to the patient's tissue (such as the location of the leads relative to various brain or spinal structures). In FIG. 7, only images 108 of the distal ends of the selected leads are depicted, but further lead structures described above could also be shown.

In the example shown in FIG. 7, the leads interface 106 can include a cursor 111 that the user can move (e.g., using a mouse connected to the clinician programmer 170) to select an illustrated electrode 16 (e.g., E1-E32, or the case electrode Ec). Once an electrode has been selected, the stimulation parameter interface 102 can be used to designate the selected electrode as an anode that will source current to the tissue, or as a cathode that will sink current from the tissue. Further, the stimulation parameter interface 102 allows the amount of the total anodic or cathodic current +I or −I that each selected electrode will receive to be specified in terms of a percentage, X. For example, electrodes E6 and E4 might be selected to each receive X=50% of the current I as an anodic current+I (0.5*+I); the corresponding cathodic current −I might then be unevenly split between electrodes E16 (0.25*−I) and E15 (0.75*−I). Thus, two or more electrodes can be chosen to act as anodes or cathodes at a given time, allowing the electric field in the tissue to be shaped.

GUI 100 can further include a lead assignment interface 112, which may comprise part of the leads interface 106. As shown, this interface 112 allows each of the leads, and in particular each of the proximal terminals of the leads, to be associated with particular ports, i.e., particular ports 22 of the IPG or particular ports 59 of the ETS. Interface 112 may also allow each port to be associated with particular electrodes supported by the IPG or ETS, although the electrodes assigned to each port can also be pre-set and not adjustable. In the example of FIG. 7, it is seen that lead type 90a is assigned to be used with port 1, which will provide the signals for electrodes E1-E8. Therefore, when properly connected, the proximal terminal 94a of lead 90a (which may comprise a plug 57 if an extender cable is used) will be connected to port 1 of the IPG or ETS, thus designating the eight electrodes of lead 90a as electrodes E1-E8. Note that lead assignment interface 112 may also include an image 114 of the IPG or ETS's ports with the port numbers labeled (1-4). Such image 114 in conjunction with the port assignment can be helpful to the clinician when connecting the leads to the various ports. Cursor 111 may also be used to select the various ports in image 114 as useful to assigning each to the leads chosen.

In FIG. 7, lead type 90b has been assigned to port 2. Therefore, when properly connected, the proximal terminal 94b of lead 90b will be connected to port 2 of the IPG or ETS, which will designate that lead's eight electrodes as E9-E16. Note that the selection of the proximal terminals 94a and 94b for leads 90a and 90b is simple because these leads have only one set of proximal terminals each.

Also shown and assigned in the leads interface 106 is lead type 90c. Assignment of this type of lead 90c (and lead type 90d) can be more complex, because as already noted this lead supports sixteen electrodes, and thus includes two proximal terminals 94c1 and 94c2 (i.e., two plugs 57 if an extender cables are used) which will be connected to two ports on the IPG or ETS. Therefore, the lead assignment interface 112 is used to assign each of the proximal terminals 94c1 and 94c2 to a particular port (3 and 4 respectively) and to particular electrodes (E17-E24 and E25-E32 respectively).

FIGS. 8A and 8B respectively show correct and incorrect connection of the leads 90a, 90b, and 90c assigned as specified in FIG. 7. It is assumed here that the leads are to be connected to ports 22 of an IPG rather than to ports 59 of an ETS, but the principle is the same. Notice in FIG. 8B that the proximal terminals 94c1 and 94c2 of lead 90c have been switched from their correct assignment, such that 94c1 is connected to port 4 and hence to electrodes E25-E32, and 94c2 is connected to port 3 and hence to electrodes E17-E24. This means that stimulation destined for electrodes E17-E24 will be sent instead to electrodes E25-E32 and vice versa. Or said differently, stimulation will not be provided at the correct location in the patient's tissue. Note that any two or more of proximal terminals 94a, 94b, 94c1 and 94c2 could be incorrectly corrected to the stimulator's ports, even though all such possible incorrect connections are not shown.

Incorrect connection of the proximal terminals to the ports of an IPG or ETS is therefore a concern, and this disclosure is directed to use of measurement and detection algorithms to either determine that leads are properly connected to their assigned IPG or ETS ports, or to determine which leads are connected to the ports even if the leads are not preassigned to the ports.

Particular focus is given in the disclosed technique to assessing and identifying leads that comprise larger number of electrodes (e.g., 16) than are supported at each port (e.g., 8), such as leads 90c and 90d. These lead types present unique challenges because their proximal terminals ultimately connect to more than one port of the IPG or ETS. In particular, such leads 90c and 90d may have electrodes (E1-E8; FIG. 6) coupled to proximal terminals 94c1 and 94d1 that are identical in shape, size, and orientation at their distal ends 92c and 92d, and therefore are difficult to distinguish, even if other electrodes (E9-E16) coupled to proximal terminals 94c2 and 94d2 of these leads 90c and 90d have different shapes, sizes, and orientations. Furthermore, the electrodes supported by each of these leads—for example, E1-E8 and E9-E16—may not differ significantly in shape, size, and orientation within such leads (e.g., 90c), making it difficult to distinguish which proximal terminals of such leads (e.g., 94c1 or 94c2) are connected to which of the IPGs or ETS's ports.

Figure 9:
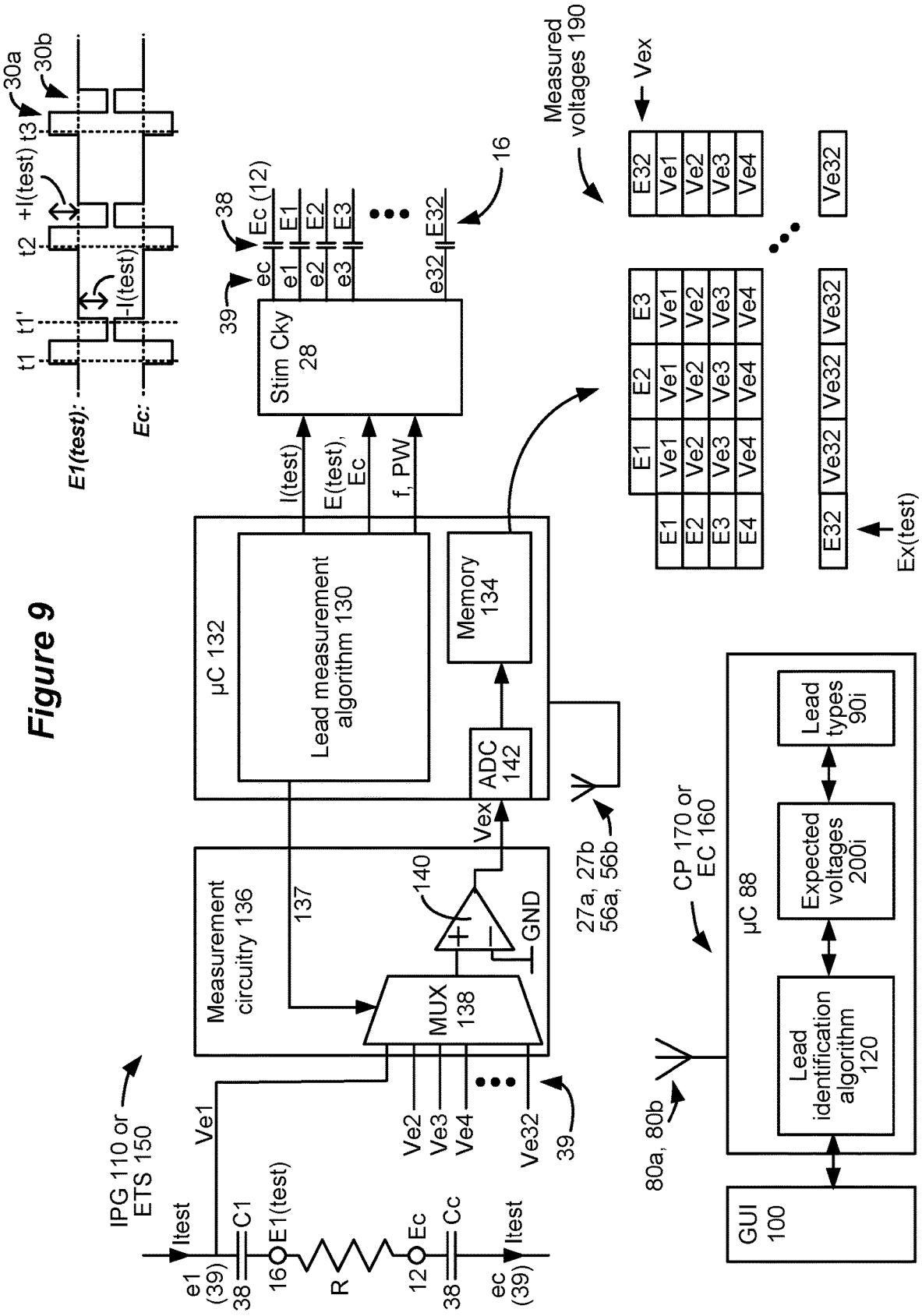
FIG. 9 shows a clinician programmer in communication with an IPG or ETS, a lead measurement algorithm operable in the IPG or ETS, and a lead identification algorithm operable in the clinician programmer for detecting leads connected to an IPG or ETS.

FIG. 9 shows an example of a system in which the disclosed technique can be implemented, and shows an implantable stimulator device such as an IPG 110 or ETS 150, and an external device such as a clinician programmer 170 or external controller 160 for communicating with the stimulator device. The IPG 110 and ETS 150 can generally be built and function as described earlier (10, 50), although a lead measurement algorithm 130 and related measurement circuitry 136 are included in addition to other functionality described below. Likewise, the clinician programmer 170 and external controller 160 can generally be built and function as described earlier (70, 60), although a lead identification algorithm 120 is used in addition to other functionality described below.

In accordance with one example, once the clinician has connected the proximal terminals 94i of the leads 90i to the ports of the IPG 110 or ETS 150, the clinician may verify that the lead connection is correct as specified in the lead assignment interface 112. This can occur by selection of an option 122 on the GUI 100 (FIG. 7) of the relevant external device, which for simplicity is assumed to be the clinician program 170 from this point forward. Selection of this option 122 starts the lead identification algorithm 120 in the clinician programmer 170. As will be described further below, the lead identification algorithm 120 operates using measurements taken in the IPG 110 or ETS 150. Lead identification algorithm 120 may comprise firmware operating within the control circuitry 88 of the clinician programmer 170 or other external device.

In one embodiment, when the verify lead connection option 122 is selected, the lead identification algorithm 120 sends an instruction to the IPG 110 or ETS 150 (e.g., via any of the various antennas described earlier) to retrieve a last measurement taken by the lead measurement algorithm 130 (which may operate on a schedule in the IPG or ETS), or to instruct the lead measurement algorithm 130 to start taking measurements. Otherwise, the lead identification algorithm 120 then waits for the measurement results to be transmitted from the IPG 110 or ETS 150 for further processing, as explained below.

Once the instruction is received at the IPG 110 or ETS 150, the lead measurement algorithm 130 in the IPG 110 or ETS 150 begins or if already measured is retrieved. Lead measurement algorithm 130 is preferably implemented as firmware (microcode) operating in the IPG 110 or ETS 150's control circuitry 132. Control circuitry 132 in one example can comprise a microcontroller, such as Part Number MSP430, manufactured by Texas Instruments, which is described in data sheets at http://www.ti.com/lsds/ti/microcontroller/16-bit_msp430/overview.page?DCMP=MCU_other& HQS=msp430. The control circuitry 132 more generally can comprise a microprocessor, Field Programmable Grid Array, Programmable Logic Device, Digital Signal Processor or like devices. Control circuitry 132 may include a central processing unit capable of executing instructions, with such instructions stored in volatile or non-volatile memory within or associated with the control circuitry. Control circuitry 132 may also include, operate in conjunction with, or be embedded within an Application Specific Integrated Circuit (ASIC), such as described in U.S. Patent Application Publications 2008/0319497, 2012/0095529, 2018/0071513, or 2018/0071520. The control circuitry 132 may comprise an integrated circuit with a monocrystalline substrate, or may comprise any number of such integrated circuits operating as a system. Control circuitry may also be included as part of a System-on-Chip (SoC) or a System-on-Module (SoM) which may incorporate memory devices and other digital interfaces. Stimulation circuitry 28 may comprise a portion of the control circuitry 132 as may measurement circuitry 136 discussed further below.

The lead measurement algorithm 130 can execute a test whereby a test current I(test) is provided to a selected electrode, E(test), which selected electrode preferably varies during the test as explained further below. I(test) is preferably formed as pulses, such as biphasic pulses as shown in FIG. 9, although monophasic pulses could be used as well. Preferably the case electrode 12 (Ec) acts as a return electrode for selected electrode E(test). I(test) may be provided to selected electrode E(test) as an anode electrode (e.g., during a first pulse phase 30a) to source +I(test) to the tissue, with the case electrode 12 (Ec) acting as a return cathode to sink −I(test) from the tissue. However, this isn't strictly necessary, and the selected electrode E(test) can also comprise a cathode with Ec acting as a return anode. Further, it is not strictly necessary that the case electrode Ec act as the return electrode, and instead a lead-based or other electrode could also be used. In FIG. 9 it is assumed that lead measurement algorithm 130 first selects electrode E1 (E1(test)) to receive I(test), then E2 (E2(test)), and so on until, preferably, all electrodes have been tested.

Figure 3:
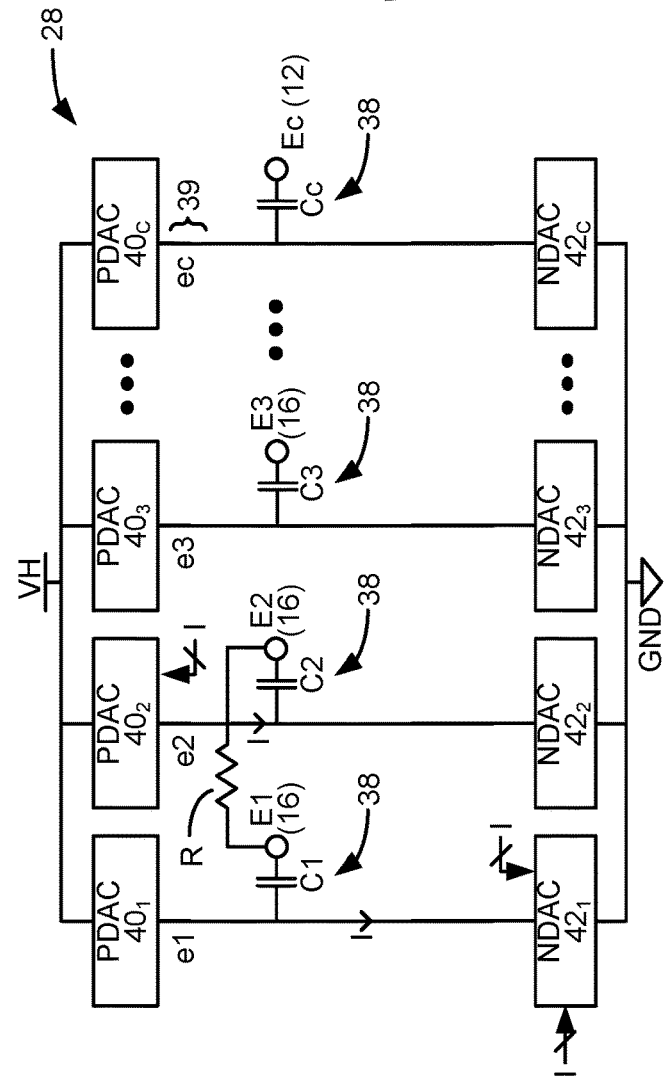
FIG. 3 shows an example of stimulation circuitry useable in the IPG or ETS, in accordance with the prior art.

As shown in FIG. 9, I(test), the selected electrodes E(test) and Ec, and the selected electrodes' polarities (anode or cathode) can be provided to the IPG or ETS's stimulation circuitry 28 as described earlier (FIG. 3), and with relevant timing information such as pulse frequency (f) and pulse width (PW). At various times during the provision of the test current I(test), measurement circuitry 136 under control of the lead measurement algorithm 130 will measure a voltage at each of the electrode nodes 39. In one example, measurement circuitry 136 can include a multiplexer 138 having inputs connected to the electrode nodes ei 39. One or more control signal 137 issued by the lead measurement algorithm 130 will select one of the electrode nodes iei at appropriate times, as discussed further below. This will pass the voltage at the selected electrode node, Vex, to the input of an amplifier 140. In the example shown, the other input of the amplifier 140 can be connected to a reference potential such as ground. The amplifier 140 will output Vex, and this value can be digitized via an Analog-to-Digital Converter (ADC) 142. The ADC 142 may comprise a separate component, or may comprise part of analog input circuitry of the control circuitry 132. The various measured voltages 190 are stored in a memory 134 associated with the lead measurement algorithm 130 and/or the control circuitry 132. As will be explained further below, the measured voltages 190 are useful in identifying the type of leads that are coupled to the ports of the IPG 110 or ETS 150.

The waveform in FIG. 9 illustrates the timing at which the measurement circuitry 136 can measure the various voltages Vex at the electrodes nodes 39. In FIG. 9, it is assumed that I(test) is initially passed through E1, E1(test) as the selected electrode. The amplitude of I(test) is preferably selected to be as low as possible, and preferably lower than might otherwise be needed to provide a therapeutic effect. Ideally, the amplitude of I(test) will be low enough to not be noticeable by the patient, and I(test) may be varied from patient to patient. Although not shown, it should be understood that GUI 100 (FIG. 7) can include options to specify the particulars of the test procedure, such as defining the amplitude or other stimulation parameters for I(test). Providing I(test) at selected electrode E1(test) will cause an electric field to be formed in the patient's tissue, and thus will cause voltages Ve1, Ve2, Ve3, etc. to form at the electrodes nodes 39.

At a first point in time (t1), or during a first of the test pulses, Ve1 at electrode E1 can be measured via appropriate control of control signals 137 for the multiplexer 138. It may be beneficial to sense the electrode node voltages at the beginning of the pulses as shown in the timing diagram of FIG. 9. This is because the DC-blocking capacitors C1 and Cc 38 associated with electrodes E1(test) and case electrode Ec will not have significantly charged at the beginning of the pulse, and hence Ve1 at that point in time will generally equal the voltage at electrode E1. The timing is of less concern when sensing voltages at electrodes that aren't actively being driven. For example, when E1(test) is selected, no current flows into electrodes E2, E3, etc. . . . . Therefore, DC-blocking capacitors C2, C3, etc. won't charge, and Ve2, Ve3, etc. will equal the voltage at the electrodes E2, E3, etc. throughout the entire pulse. Note that if a biphasic pulse is used for I(test), the absolute value of the voltage can also be measured during the second phase of the pulse (t1'), with the two voltages measured at t1 and t1' being averaged for example. It may be beneficial to sense the voltage (t1') at the end of the second phase, because the DC-blocking capacitors C1 and Cc 38 associated with electrodes E1 and Ec will have been significantly discharged back to zero, and thus Ve1 at that point in time will again generally equal the voltage at electrode E1.

At a second point in time (t2), or during a second test pulse, Ve2 at electrode E2 can be measured via appropriate control of control signal 137, and Ve3 at electrode E3 can be measured at time t3, and so on until the voltages Ve1 to Ve32 at all electrode nodes have been measured using E1(test) as the selected electrode.

Different electrodes don't need to be measured for each subsequent I(test) pulse. For example, a single voltage (e.g., Ve1) can be measured over several I(test) pulses and averaged by the lead measurement algorithm 130 to improve the accuracy of the measurement. Furthermore, if more than one amplifier 140 is provided, or if an amplifier is dedicated to each electrode, more than one Vex measurement can be made at the same time (and multiplexer 138 may not be necessary). Although it is preferred that the lead measurement algorithm 130 and associated measurement circuitry 136 measure single-ended electrode node voltages Vex, the technique can also be modified to measure differential voltages measured between two electrodes.

Eventually, a next electrode E2, i.e., E2(test), can be selected at the test electrode, and thus this electrode will now receive test current I(test). Electrode node voltages Ve1 to Ve32 are then measured while using this new test electrode. Then, electrode E3(test) is chosen, and so on, until all electrode node voltages Ve1-Ve32 are measured using each of the electrodes E1 to E32 as the test electrode. As a result, in this example, the measured voltages 190 comprise a 32×32 matrix of voltage values Vex, as shown towards the bottom of FIG. 9.

A lesser number of voltage values could be measured and stored in the measured voltage matrix 190. For example, it may not be necessary to select every single electrode Ex (i.e., all 32) as Ex(test) to receive I(test), and it may not be necessary to measure every single electrode node voltage Vex for each Ex(test) electrode that is selected. However, it is preferred to select and measure every electrode to improve the reliability of lead determination, as explained further below.

Once all electrode node voltages Vex have been measured and stored in memory 134, the lead measurement algorithm 130 can wirelessly telemeter the measured voltage matrix 190 to the external device (e.g., the clinician programmer 170) running the GUI 100, where they are processed by lead identification algorithm 120. As described further below, once the measured voltage matrix 190 is received at the lead identification algorithm 120, those voltages are compared to expected electrode voltages 200i, which are explained next.

FIGS. 10A-10D shows the expected electrode voltages 200a-200d when the lead measurement algorithm 130 measures the electrode voltages for the different lead types 90a-90d described earlier (FIG. 6). The expected voltages 200a-200d for each lead type can be simulated, or can result from empirical measurements taken in a controlled setting, or taken from bench, analytic, in-silico, pre-clinical, or clinical data. As shown in FIG. 9, the expected voltages 200i for each lead type are preferably stored in memory in the clinician programmer for use by the lead identification algorithm 120, as explained further below.

FIG. 10A shows expected electrodes voltages 200a for lead type 90a, having eight ring-shaped electrodes. Expected voltages 200a in this example are expressed in milliVolts, but the absolute magnitude of the expected voltages will depend on many factors, such as the assumed conductivity of the tissue, the surface areas (resistances) of the electrodes, the distance between the electrodes and the case electrode Ec, and the amplitude of I(test).

The first row shows the expected voltages when electrode E1 (E1(test)) receives test current I(test). This causes a voltage of Ve1=286 mV to be formed at E1, and forms an electric field in the tissue that couples a voltage to all other electrodes E2-E8, as described above. Electrode E2, which is close to E1, couples a voltage smaller than Ve1 (Ve2=90 mV). Electrode E3, which is farther from E1, couples a still smaller voltage (Ve3=48 mV). The smallest coupled voltage is at electrode E8, which is farthest away from E1 (Ve8=14 mV).

The second row shows the expected electrode voltages that result when electrode E2 (E2(test)) receives test current I(test). This causes a voltage of Ve2=282 mV to be formed at E2. Because the distance between the electrodes and case electrode Ec is much larger than the distances between individual electrodes, notice that Ve2 is generally equal to Ve1 (286 mV) when E1(test) receives I(test). Electrodes E1 and E3, which are close and equidistant to E2, couple to a voltage smaller than Ve2 (Ve1=Ve3=90 mV). Electrode E4, which is farther from E2, couples to a still smaller voltage (Ve4=49 mV). Notice that Ve4 (49 mV) when E2(test) receives I(test) is generally equal to Ve3 (48 mV) when E1(test) receives I(test), which makes sense because each of these electrodes are the same distance away from the electrode receiving I(test).

The 8×8 matrix of expected voltages 200a for lead type 90a is shown at the bottom in FIG. 10A depicted using a gray scale, which is helpful in visualizing the results (with lighter grey scales indicating higher voltages). As can be seen, the highest expected voltages occur when the electrodes that receive the I(test) current are the same as those being measured, thus resulting in the lighter-grey shading of the elements in the matrix along diagonal 202a.

FIG. 10B shows an 8×8 matrix of expected electrodes voltages 200b for lead type 90b. The different size and relative locations of the eight electrodes in lead type 90b provide different expected electrode voltages when compared to lead type 90a. For example, in the first row when ring-shaped electrode E1 (E1(test)) receives test current I(test), we see that Ve1 equals 362 mV. Split-ring electrodes E2/E3/E4 are all equidistant from E1, and therefore couple voltages smaller than Ve1 but relatively equal in magnitude (Ve2=140 mV, Ve3=139 mV, Ve4=144 mV). Split-ring electrodes E5/E6/E7 are also equidistant from E1 but farther away; these electrodes therefore couple even smaller voltages that relatively equal in magnitude (Ve5=87 mV, Ve6=87 mV, Ve4=91 mV).

The second row shows expected electrode voltages that result when electrode E2 (E2(test)) receives test current I(test). This causes a voltage of Ve2=653 mV to be formed at E2. Notice that this voltage is higher than Ve1 (362 mV) when E1 (E1(test)) receives test current I(test). This is because split-ring electrode E2 is smaller in area than ring-shaped electrode E1, and therefore has a higher resistance. As a result, a larger voltage must be formed at E2 to effect the same magnitude current for I(test). Diagonal 202b for lead type 92 thus shows that the highest expected voltages occur at the split-ring electrodes E2-E7 when they both receive I(test) and are measured. Measurements at ring-shaped electrodes E1 and E8 are lower when they receive I(test), as shown by matrix elements 213.

Figure 10C:
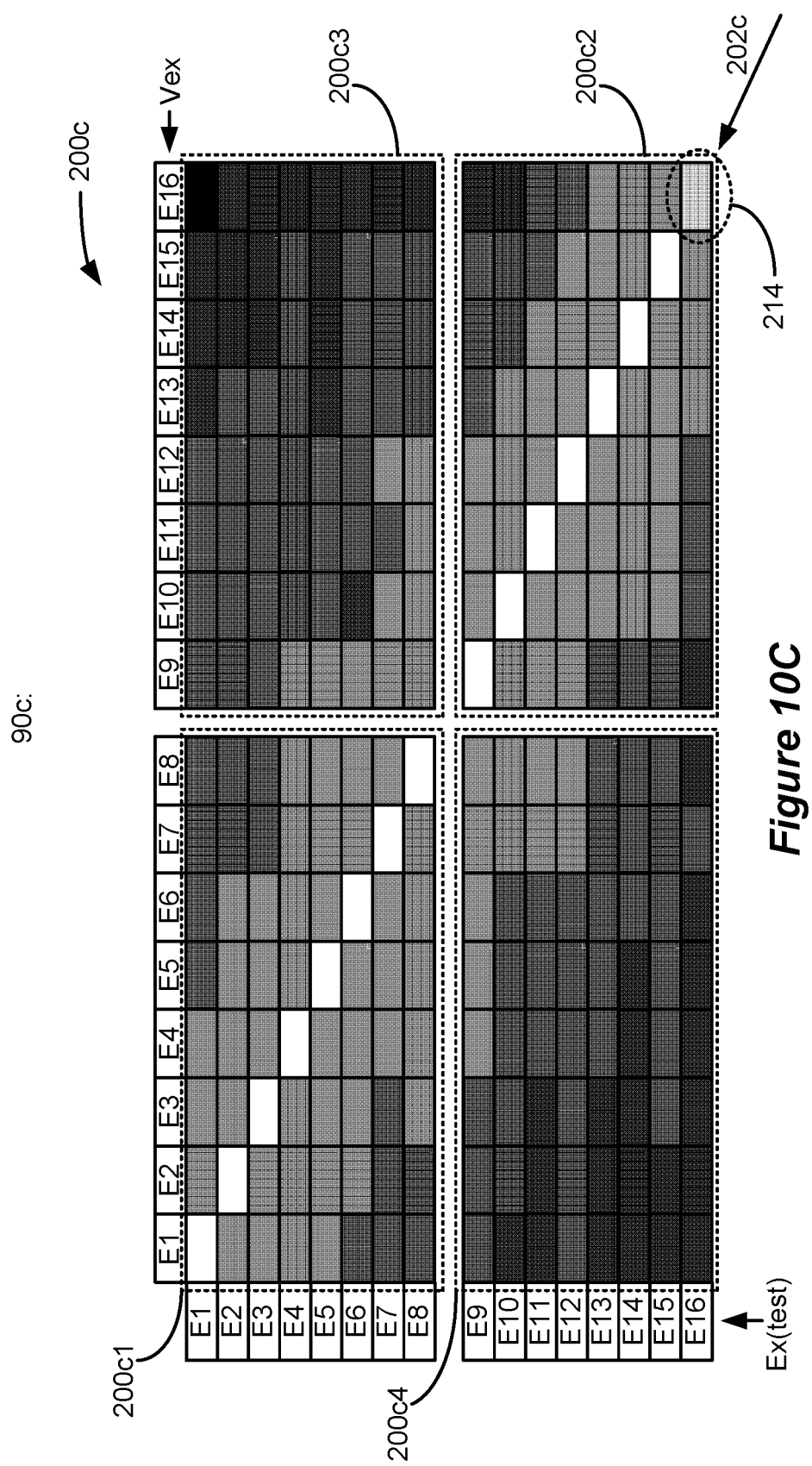
Figure 10D:
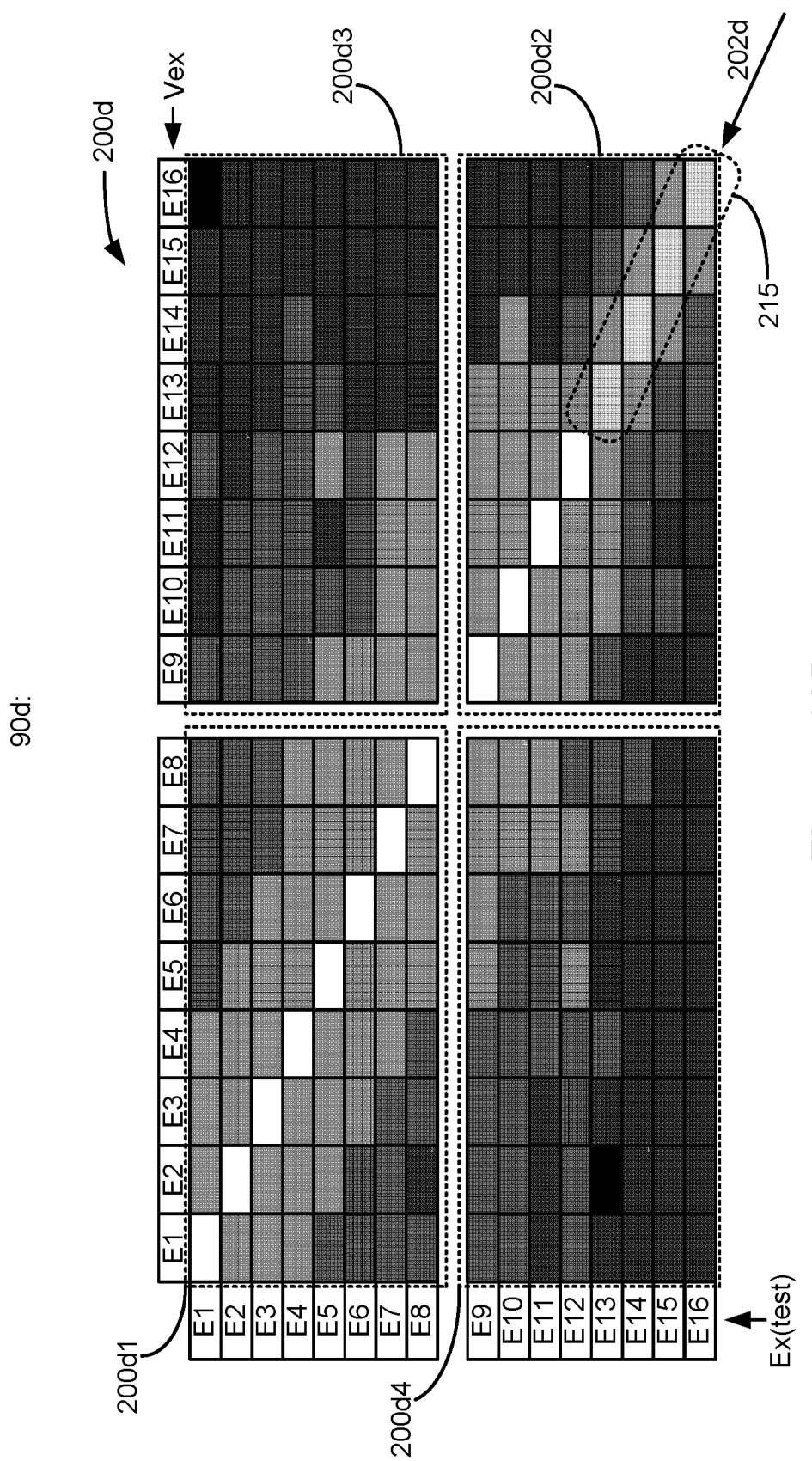

FIGS. 10C and 10D show expected electrodes voltages 200c and 200d for lead types 90c and 90d respectively, both of which have sixteen electrodes, and therefore are represented as a 16×16 matrix of values. For simplicity, voltage magnitudes are not shown, and instead the data is depicted only using grey scale to represent the voltages. It is again interesting to note the expected voltages of the elements at the diagonals 202c and 202d202d. Diagonal 202c for lead type 90c (FIG. 10C) shows that the highest expected voltages occur at electrodes E1-E15 when they receive I(test) and are measured, and that the expected voltage at E16 is lower (but still relatively high) when it receives I(test) and is measured, as seen at element 214. This can result from the different sizes, shapes, and orientations of the particular electrodes E1-E16 on lead 90c. Diagonal 202d for lead type 90d (FIG. 10D), which has different sizes, shapes or orientations of its electrodes, shows that the highest expected voltages occur at electrodes E1-E12 when they receive I(test) and are measured, and that the expected voltages at electrodes E13-E16 are lower (but still relatively high) when they receive I(test) and are measured, as seen at elements 215.

It is useful in understanding the description that follows to break the expected voltages 200c and 200d of lead types 90c and 90d into four 8×8 regions. This is useful, because as described these sixteen-electrode leads terminate at two eight-electrode proximal terminals and thus will connect to two ports of the IPG 110 or ETS 150. Thus, in FIG. 10C, the 16×16 matrix of expected voltages 200c for lead type 90c is broken into on-diagonal regions 200c1 and 200c2, and off-diagonal regions 200c3 and 200c4. Likewise, in FIG. 10D, the 16×16 matrix of expected voltages 200d for lead type 90d is broken into on-diagonal regions 200d1 and 200d2, and off-diagonal regions 200d3 and 200d4.

Note that the expected voltages 200i are largely symmetric relative to the diagonals 202i—i.e., the expected voltages are largely mirrored across the diagonals 202$i$, such that for example testing at electrode E6 and measuring at electrode E4 provides the same expected value as testing at electrode E4 and measuring at electrode E6. In this regard, it may only be necessary in the disclosed technique to consider expected voltages 200$i$ on one side of the diagonals 202$i$.

It should be clear that from FIGS. 10A-10D that the expected voltages 200$i$ are different for each of the lead types chosen, which results from differences in the electrodes along the leads 90$i$. As will be discussed further below, these unique signatures for each of the leads can be used to detect which leads are connected to which ports 22 or 59 of the IPG 110 or ETS 150, and thus whether such leads have been correctly connected.

Figure 11A:
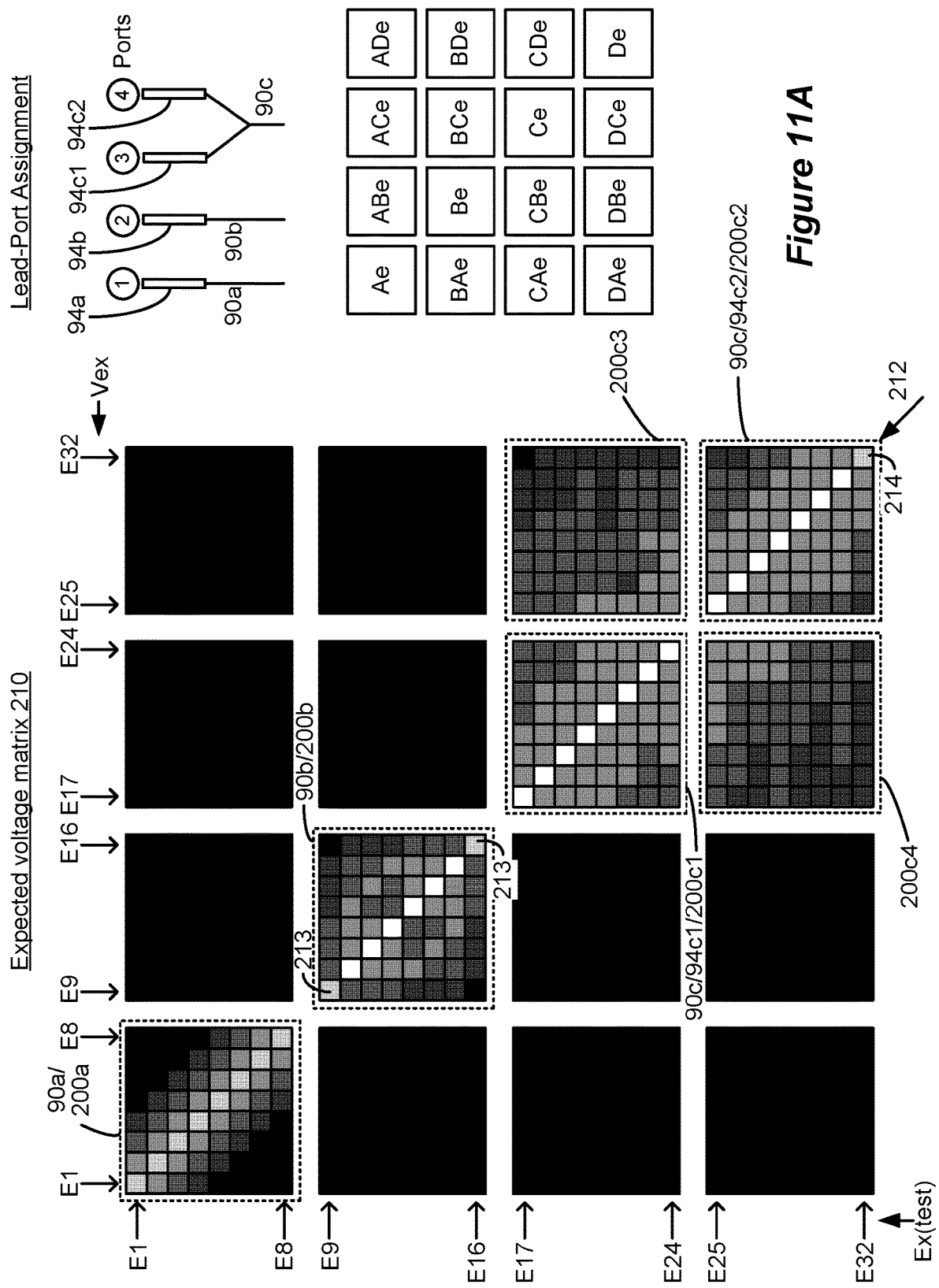
FIGS. 11A-11C show compilation of an expected voltage matrix using assigned lead types and their expected voltages, including division of the expected voltage matrix into on-diagonal and off-diagonal regions.

FIG. 11A shows the expected voltages 210 when the leads 90$a$, 90$b$, and 90$c$ are connected to their appropriate IPG 110 or ETS 150 ports per the configuration specified in the GUI 100 of FIG. 7, and as shown in the diagram to the upper right. The expected voltages 210 result in a 32×32 matrix of values, which results from assigning the expected voltages 200$i$ corresponding to lead types 90$a$-90$c$ into different 8×8 regions of the 32×32 matrix of expected voltages 210. Four of these regions—Ae, Be, Ce, and De—are along a diagonal 212 of the expected voltage matrix 210, and are referred to as "on-diagonal" regions. The electrodes tested (E(test)) and measured (Vex) in on-diagonal regions Ae-De are the same, and comprise electrodes corresponding to a particular port of the IPG or ETS. Specifically, region Ae comprises expected voltages when electrodes E1-E8 are both tested and measured, which electrodes correspond to port 1 of the IPG or ETS. Region Be comprises expected voltages when electrodes E9-E16 are both test and measured, which electrodes correspond to port 2 of the IPG or ETS, and so on for regions Ce (electrodes E17-E24; port 3) and De (E25-E32; port 4).

Twelve of the regions in the expected voltage matrix 210 are not along diagonal 212, and are referred to as "off-diagonal" regions. The electrodes tested (E(test)) and measured (Vex) in the off-diagonal regions do not comprise electrodes corresponding to the same port of the IPG or ETS. Off-diagonal regions are designated in FIG. 11A by two letters, showing their correspondence to the on-diagonal regions Ae-De. For example, region ABe comprises the expected voltages when the electrodes of region Ae are tested (E1-E8; corresponding to port 1), but the electrodes of region Be are measured (E9-E16; corresponding to different port 2), etc.

The expected voltage matrix 210—and more specifically each of its regions—is populated with the expected voltages 200$i$ for each of the lead types connected to the IPG 100 or ETS 150, which requires an understanding of which leads 90$i$—and more particularly which proximal terminals 94$i$ of the leads—are assigned to which ports of the IPG or ETS.

For example, proximal terminal 94$a$ of lead type 90$a$, an 8-electrode lead, is designated for connection to port 1 of the IPG or ETS, which port corresponds to electrodes E1-E8. Therefore, region Ae comprises the expected voltages 200$a$ for this lead type 90$a$ (FIG. 10A).

Proximal terminal 94$b$ of lead type 90$b$, again an 8-electrode lead, is designated for connection to port 2 of the IPG or ETS, which port corresponds to electrodes E9-E16. Therefore, region Be comprises the expected voltages 200$b$ for this lead type 90$b$ (FIG. 10B).

Lead type 90$c$ is a sixteen electrode lead having two proximal terminals 94$c$1 and 94$c$2, which implicates both on-diagonal and off-diagonal regions in the expected voltage matrix 210. Proximal terminal 94$c$1 is designated for connection to port 3 of the IPG or ETS, which port corresponds to electrodes E17-E24. Therefore, region Ce comprises the expected voltages 200$c$1 for this lead type 90$c$ (FIG. 10C). Proximal terminal 94$c$2 is designated for connection to port 4 of the IPG or ETS, which port corresponds to electrodes E25-E32. Therefore, region De comprises the expected voltages 200$c$2 for this lead type 90$c$ (FIG. 10C). This assignment of expected voltages 200$c$1 and 200$c$2 to on-diagonal regions Ce and De also sets the assignment of expected voltages 200$c$3 and 200$c$4 (FIG. 10C) to off-diagonal regions CDe and DCe respectively.

In the expected voltage matrix 210 of FIG. 11A, it is assumed that the leads are sufficiently far away from each other that testing of an electrode on one lead will not couple a significant voltage to an electrode on another lead. For example, in off-diagonal region ABe, in which the electrodes of lead 90$a$ are tested (E1-E8), but the electrodes of lead 90$b$ are measured (E9-E16), near-zero voltage values are expected, hence the reason region ABe is darkly shaded. Regions ACe, ADe, BCe, BDe, BAe, CAe, CBe, DAe, and DBe should also expect near-zero voltage values as well. Off-diagonal regions CDe and DCe by contrast involve testing and measuring on the same 16-electrode lead 90$c$, and thus should register significant voltage values (expected voltages 200$c$3 and 200$c$4), as evidenced by the lighter-shaded elements in those regions. As discussed further below, these off-diagonal regions CDe and DCe can be particularly useful in determining that a sixteen-electrode lead is connected to ports 3 and 4, and more particularly which of its proximal terminals are connected to which port.

Figure 11B:
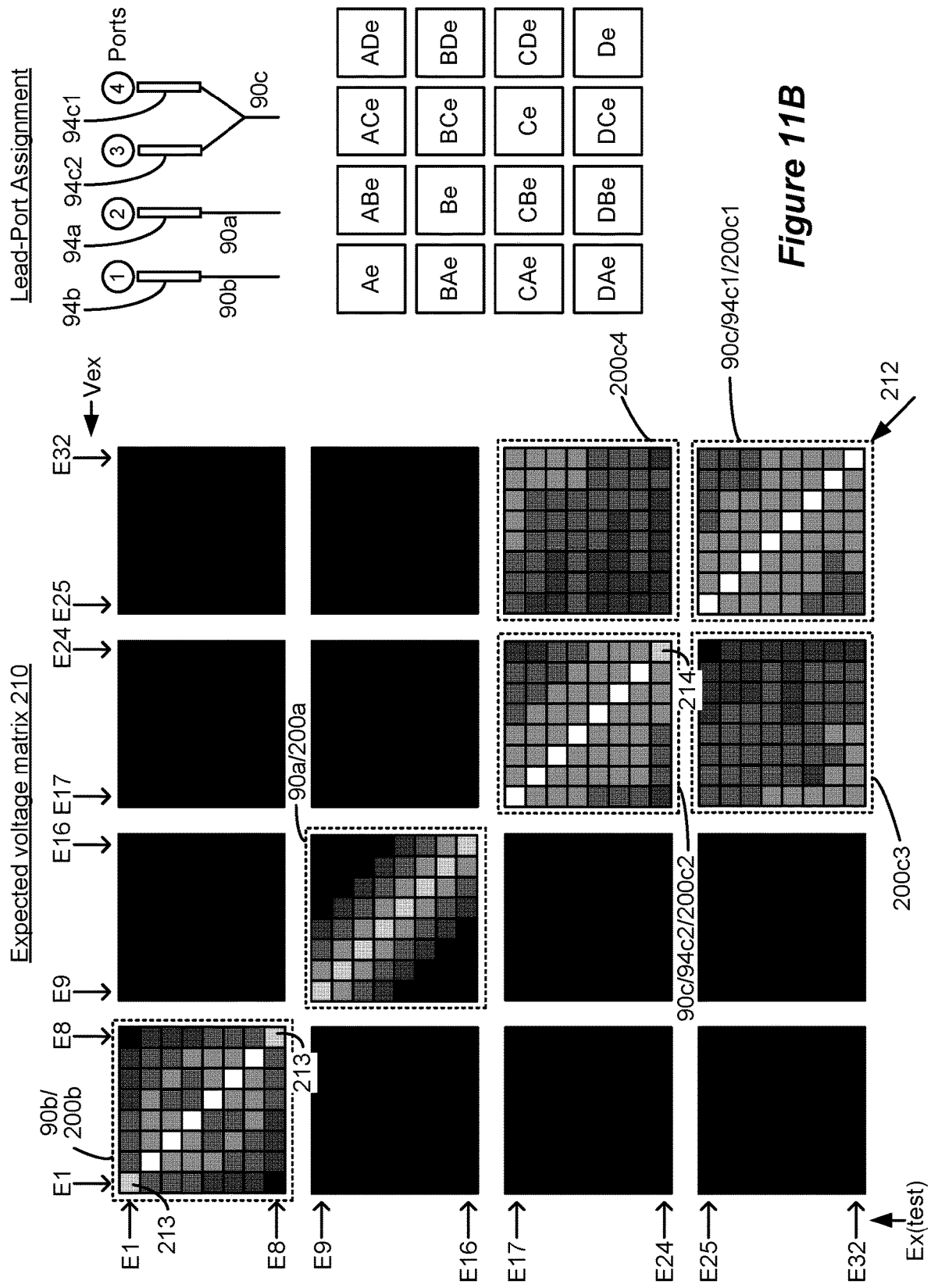

FIG. 11B shows the expected voltage matrix 210 for a different lead-to-port assignment compared to that illustrated in FIG. 11A. In this example, it is assumed in the GUI 100 (FIG. 7), and as shown in the upper right, that lead type 90$b$ (proximal terminal 94$b$) is assigned to port 1 (electrodes E1-E8), and lead type 90$a$ (proximal terminal 94$a$) is assigned to port 2 (electrodes E9-E16). This flips the expected voltages in expected voltage matrix 210, such that expected voltages 200$b$ (FIG. 10B) are now assigned to on-diagonal region Ae, and expected voltages 200$a$ (FIG. 10A) are now assigned to on-diagonal region Be.

In FIG. 11B, it is further assumed that lead type 90$c$ is used again, but that the two proximal terminals 94$c$1 and 94$c$2 of that lead are assigned to different ports. Specifically, the assignment of these proximal terminals are flipped, such that proximal terminal 94$c$2 is assigned to port 3 (electrodes E17-E24), and proximal terminal 94$c$1 is assigned to port 4 (electrodes E25-E32). This again flips the expected voltages in expected voltage matrix 210, such that expected voltages 200$c$2 (FIG. 10C) are now assigned to on-diagonal region Ce, and expected voltages 200$c$1 (FIG. 10C) are now assigned to on-diagonal region De. This assignment also sets the assignment of expected voltages 200$c$3 and 200$c$4 to off-diagonal regions CDe and DCe respectively, which is flipped from the previous example (FIG. 11A).

Figure 11C:
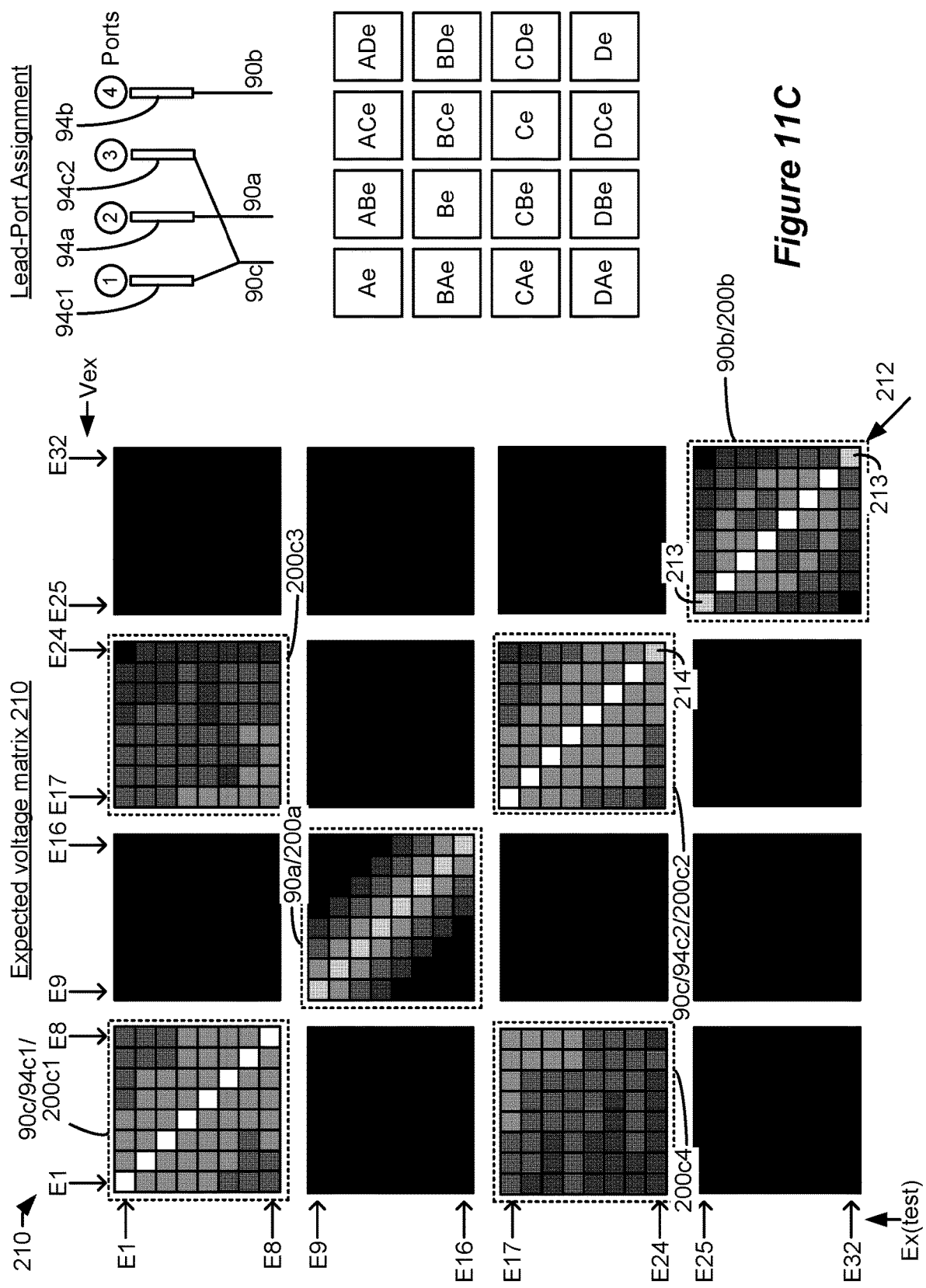

FIG. 11C shows the expected voltage matrix 210 for a yet another different lead-to-port assignment. In this example, it is assumed that proximal terminal 94$c$1 of lead type 90$c$ is assigned to port 1 (electrodes E1-E8), thus assigning expected voltages 200$c$1 to on-diagonal region Ae. Lead type 90$a$ (proximal terminal 94$a$) is assigned to port 2 (electrodes E9-E16), thus assigning expected voltages 200$a$ to on-diagonal region Be. Proximal terminal 94$c$2 of lead type 90$c$ is assigned to port 3 (electrodes E17-E24), thus assigning expected voltages 200$c$2 to on-diagonal region Ce. Lead type 90$b$ (proximal terminal 94$b$) is assigned to port 4 (electrodes E25-E32), thus assigning expected voltages 200$b$ to on-diagonal region De. Notice in this example that assigning the expected voltages 200c1 and 200c2 to on-diagonal regions Ae and Ce also sets expected voltages 200c3 and 200c4 to corresponding off-diagonal regions ACe and CAe respectively.

Figure 12A:
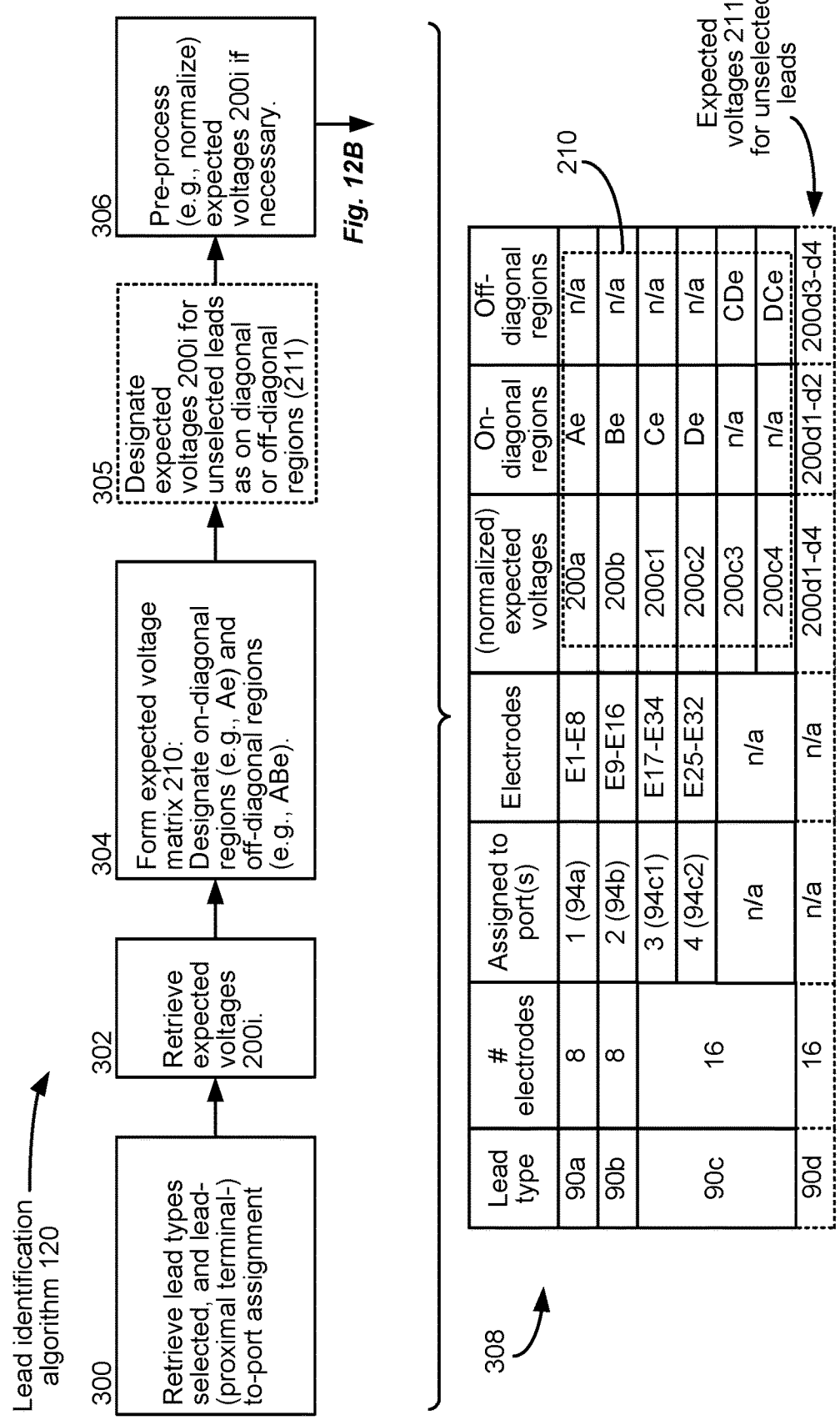

With the foregoing in hand, operation of one example of lead identification algorithm 120 is illustrated starting with FIG. 12A. At a high level, algorithm 120 involves comparison of the measured voltage matrix 190 with the expected voltages 200i, and in this regard it is assumed that operation of the lead measurement algorithm 130 (FIG. 9) has already occurred. It should be noted that not all illustrated steps are necessary to perform, and other steps could be added as necessary. Further, it is not strictly required to perform the steps in the order illustrated.

Starting with FIG. 12A, in step 300, the GUI 100 is consulted to determine which lead types 90i have been selected, and to determine which proximal terminals 94i of those lead types are assigned to which port and hence to which electrodes. In step 302, expected voltages 200i are retrieved. This may comprise retrieving only the expected voltages 200i for the leads 90i selected for use in the GUI 100 (e.g., 90a-c, 200a-c).

Optionally, step 302 may further retrieve the expected voltages 200i for all leads supported by the system, even if such leads have not been selected for use (e.g., 90d, 200d). As will be explained further below, retrieving the expected voltages 200i for all leads 90i supported by the system is useful to identify whether the clinician has possibly implanted an incorrect lead type that was not selected for use using GUI 100, or to identify that the clinician has misassigned a lead type or proximal terminal to a particular port in the GUI 100. Note that the type of IPG or ETS being used is typically known by the system, and the system may further understand which leads in its library can function with the particular IPG or ETS chosen. As such, the algorithm 120 may retrieve only expected voltages 200i for leads 90i that can operate with the IPG or ETS in question.

In step 304, the expected voltage matrix 210 is formed using the expected voltages 200i for the selected leads, and using the lead—(or proximal terminal-) to-port assignments (300). Formation of the expected voltage matrix 210 was explained with reference to FIGS. 11A-11C, and preferably involves designating on-diagonal regions (Ae) and off-diagonal regions (e.g., ABe) within the matrix 210.

In optional step 305, the expected voltages 211 for unselected leads (e.g., 90d, 200d), while not part of the expected voltage matrix 210, are also retrieved and designated as on-diagonal or off-diagonal regions. Whether an unselected lead's expected voltages will implicate off-diagonal regions depend on the number of electrodes it has. If for example eight-electrode lead (90a or 90b) was not selected, its expected voltages (200a or 200b) would only be designated as an on-diagonal region, because such data would fill only one 8×8 region (see FIGS. 10A and 10B). If a sixteen-electrode such as lead 90d was not selected, its expected voltages 200d1 and 200d2 would be assigned as potential on-diagonal voltages regions, and its expected voltages 200d3 and 200d4 would be assigned as potential off-diagonal voltage regions (see FIG. 10D).

In step 306, the expected voltages 200i can optionally be pre-processed in any manner necessary to assist with further processing. In one example, pre-processing may include normalizing the expected voltages 200i, which can be done in different ways. In one example, normalization of the voltages occurs on a per-region basis. For example, the control circuitry 88 can review region Ae (e.g., expected voltages 200a; FIG. 10A) and determine a highest expected voltage in that matrix (e.g., 318 mV). The expected voltages in this region can then be divided by that highest voltage, such that the expected voltages 200a will range from 0 to 1. Alternatively, normalization of the expected voltages 200i can occur not on a per-region basis but taking all expected voltages into account simultaneously. Pre-processing can also include smoothing the expected voltage data in various fashions. The expected voltages for example can be divided into binned voltages ranges, and if necessary outlier data points (voltages that are aberrantly too high or too low) can be removed or adjusted. Note that the expected voltages 200i as stored in the clinician programmer 170 can be pre-processed in these and other fashions prior to operation of the lead identification algorithm 120.

The results of steps 300-306 are summarized in FIG. 12A in the form of a table 308. Table 308 includes data indicative of formation of the expected voltage matrix 210, and specifically in this example the expected voltage matrix 210 shown earlier in FIG. 11A. In addition, per optional step 305, table 308 may include the expected voltages 211 for unselected leads (e.g., 90d), may be used by the algorithm 120 to determine if an unselected lead has been used by the clinician. As mentioned above, expected voltages 211 for unselected leads can be assigned into on—(e.g., 200d1, 200d2) and off—(e.g., 200d3, 200d4) diagonal regions if the number of electrodes of such leads (e.g., 16) is larger than the number of electrodes that each port supports (e.g., 8).

Next, and referring to FIG. 12B, the measured voltage matrix 190 (FIG. 9), is received from the IPG 110 or ETS 150, if this has not occurred already. In step 312, the measured voltage matrix 190—similarly to the expected voltage matrix 210—is divided into sixteen 8×8 regions, which again can comprise on-diagonal regions Am-Dm, and off-diagonal regions ABm, ACm, etc. In step 314, the measured voltage matrix 190 can optionally be pre-processed in various fashions, similar to what was described earlier (306) for the expected voltage matrix 210.

Figure 12C:
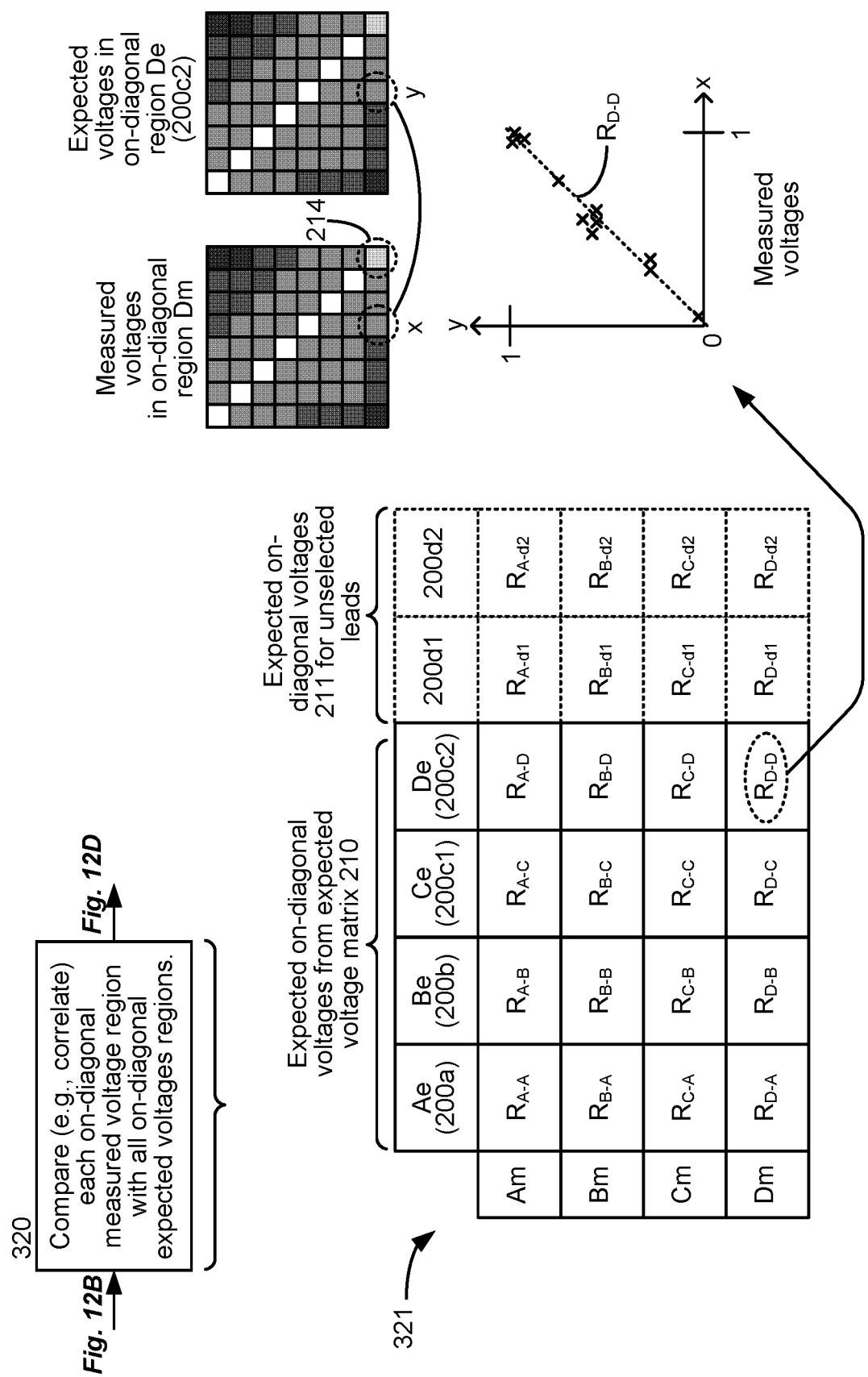
Figure 12D:
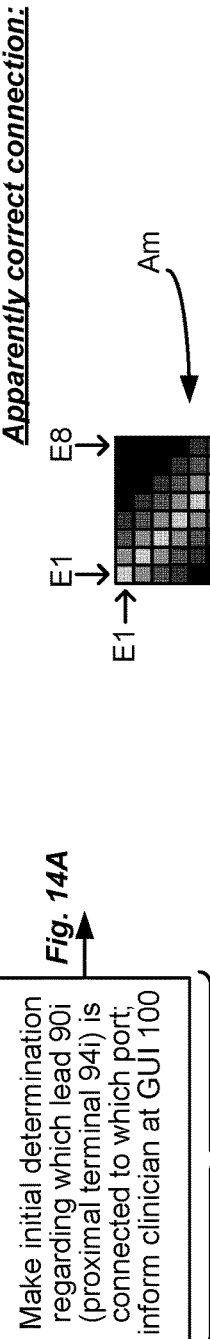
Figure 12D:
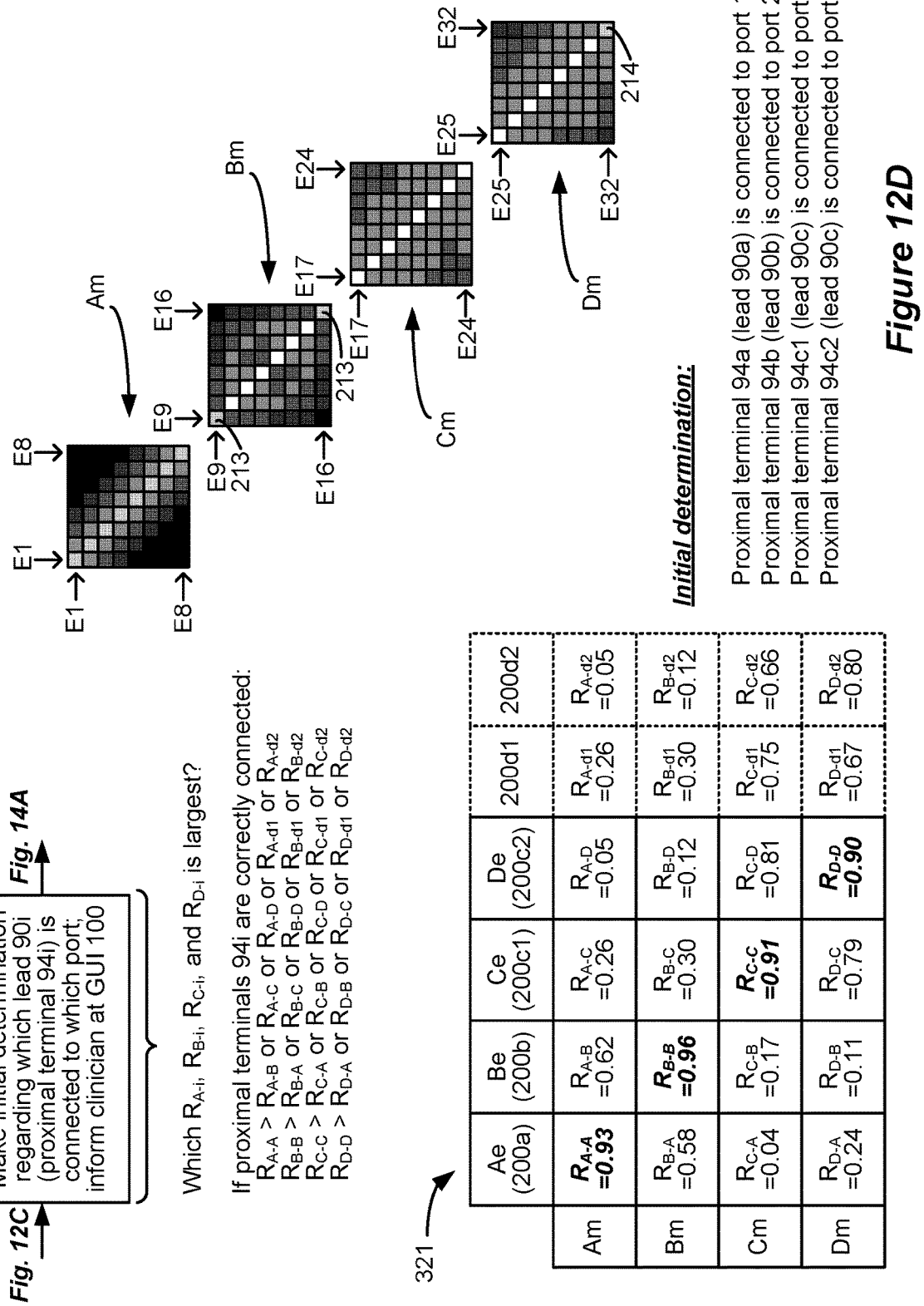

Referring now to FIGS. 12C and 12D, next steps 320 and 322 of the lead identification algorithm 120 assess only the measured on-diagonal regions Am-Dm, and compare them with expected on-diagonal regions to arrive at an initial determination concerning which leads, or which proximal terminals of the leads, are connected to which ports of the IPG 100 or ETS 150. Assessing the measured on-diagonal regions is useful because significant voltages appear within these regions, and therefore assessment of these regions alone can be sufficient to identify the leads or proximal terminals connected to the ports. However, the lead identification algorithm 120 may also consider off-diagonal regions as well, as explained further below.

In step 320, as shown in FIG. 12C, the measured voltages in each on-diagonal region (Am-Dm) are preferably compared to all on-diagonal expected voltages (e.g., for each possible lead type) to see which one they match best. Such comparison can occur in any number of ways, but in a preferred method the elements in the measured Im and expected Ie regions are correlated with each other to determine a correlation coefficient, R. The computation of correlation coefficient $R_{D-D}$, by which the measured voltages in region Dm are compared against the expected voltages (200c2) in region De, is illustrated as one example in FIG. 12C. As shown in the graph, an element x from measured voltage region Dm is plotted against a corresponding element y from the expected voltage region De. In this example, 64 points would be plotted corresponding to the 64 elements in these regions, but not all are shown. It is assumed here that the measured and expected voltages have been normalized to range between 0 and 1 (steps 306 and 314). After the (x,y) values for the corresponding elements are determined, correlation coefficient $R_{D-D}$ can be determined using standard means, such as a linear regression analysis. As one skilled in the art understands, the correlation coefficient $R_{D-D}$ will range from 0 to 1, with 0 indicating a poor match between the measured voltages in region Dm and expected voltages in region De, and with a 1 indicating a perfect match. Of course, the GUI 100 may not actually plot the computation of the correlation coefficients as shown, and instead the lead identification algorithm 120 would determine the (x,y) values and determine the correlation coefficient using the control circuitry 88 in the clinician programmer 170.

The lead identification algorithm 120 can perform the comparison of the measured and expected voltages at step 320 in other ways. For example, the elements in each matrix can be subjected to principle component analysis techniques or use other machine learning algorithms, such as those commonly used in imaging analysis. When using such techniques, the lead identification algorithm 120 will determine the most significant features in the matrices being compared that would tend to maximize their variance. For example, the lead identification algorithm 120 when using principle component analysis can determine a subspace of the m-by-64-dimensional dataset (where m represents the number of possible lead types) which maximizes the variance across different lead types. This subspace could be calculated previously, and simply stored in the clinician programmer 170. Expected and measured voltages would then be projected onto this subspace. Any cost function could be used to calculate the closeness of the fit between measured and expected voltages (projected onto this subspace), such as the l1-norm. Unlike a correlation coefficient, in which a high value suggests a good fit, the l1-norm (and other similar cost functions) will instead have a low value when there is a good fit between measured and expected voltages. Again, other comparative techniques could be used as well that output other measures of confidence regarding the comparison of the expected and measured voltages. Information about confidence can be created and/or output other points during the algorithm 120. Holistic sanity checks may also be performed on resulting predictions, etc.

It should be recognized that it is not necessary in step 320 that all elements in the on-diagonal regions be compared or correlated. For example, and as explained earlier (FIGS. 10A-10D), the most significant (highest) voltage elements appear along a diagonal in each region, and certain of these elements (e.g., 214 for lead type 90c) are unique to each lead type. Extra weight or significance may therefore be placed on these more significant elements during comparison step 320, so much so that other elements in the regions being compared may be omitted for consideration during the comparison. Further, correlation may be limited to elements appearing on only one side of the diagonals in each on-diagonal region, because as previously noted it would be expected that similar results would be mirrored across such diagonals.

Once the measured voltages of each on-diagonal region have been compared to all other expected voltage on-diagonal regions, a comparison matrix 321 is determined, which in this examples comprises the various correlation coefficients R described earlier. In this example, the comparison matrix 321 is a 4x6 matrix, because each measured on-diagonal voltage region (e.g., Am) is compared against all expected on-diagonal voltage regions from the expected voltage matrix 210 (e.g., Ae, Be, Ce, De) as well as the expected on-diagonal voltages 211 (200d1 and 200d2) from unselected leads (90d). The size of comparison matrix 321 can be different, and will depend on the number of type of unselected leads supported by the system if such lead types are optionally considered by the lead identification algorithm 120.

The comparison matrix 321 can then be used to make an initial determination as to which lead type (or which proximal terminal) appears to be connected to each port of the IPG 110 or ETS 150, as shown in step 322 of FIG. 12D. This can occur by identifying the highest correlation coefficient for each measured on-diagonal region Am-Dm. In FIG. 12D, it is assumed that the leads 90a, 90b, and 90c and their terminal (notably proximal terminals 94c1 and 94c2 of lead 90c) are properly connected as specified in the GUI 100 of FIG. 7. In this instance, it would be expected that the measured voltages in region Am would best correlate to the expected voltages (200a) in region Ae, and would more poorly correlate to the expected voltages (200b, 200c1 and 200c2) in regions Be, Ce, and De and to other on-diagonal expected voltages (e.g., 200d1 and 200d2) for unselected leads. In other words, $R_{A-A}$ should be greater than $R_{A-B}$, $R_{A-C}$, $R_{A-D}$, $R_{A-d1}$, and $R_{A-d2}$ as shown in correlation coefficient matrix 321. Likewise, it would be expected that the measured voltages in region Bm would best correlate to the expected voltage (200b) in region Be, and would more poorly correlate to the expected voltages in regions Ae, Ce, and De, and to 200d1 and 200d2. In other words, $R_{BB}$ should be greater than $R_{B-A}$, $R_{B-C}$, $R_{B-D}$, $R_{B-d1}$, and $R_{B-d2}$, etc. If this is observed, then the lead identification algorithm 120 would at least initially determine that the leads/proximal terminals appear to be correctly connected to their assigned ports as defined in the GUI 100 (FIG. 7).

Figure 12E:
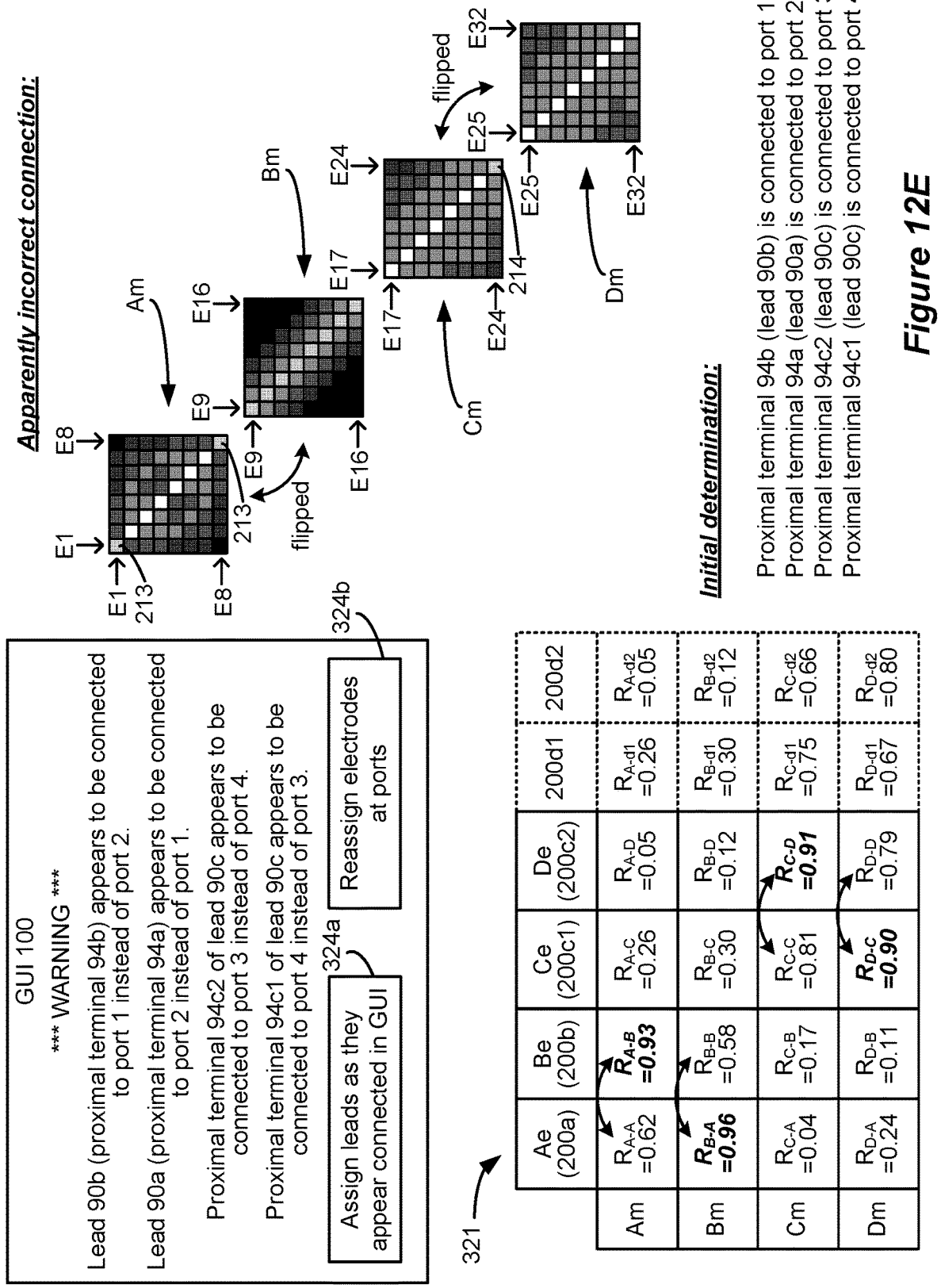

FIG. 12E shows the initial determination made in step 322 if the leads/proximal terminals do not appear to be correctly connected. In this example, it assumed that the leads/proximal terminals have been connected (in contravention of the assignments entered into the GUI 100 of FIG. 7) as described in FIG. 11B: with lead type 90b (proximal terminal 94b) connected to port 1 (electrodes E1-E8); lead type 90a (proximal terminal 94a) connected to port 2 (electrodes E9-E16); proximal terminal 94c2 of lead type 90c connected to port 3 (electrodes E17-E24); and proximal terminal 94c1 of lead type 90c connected to port 4 (electrodes E25-E32). In other words, leads 90a and 90b (proximal terminals 94a and 94b) are switched at ports 1 and 2, and the proximal terminals 94c1 and 94c2 of lead 90c are switched at ports 3 and 4.

In this case, the measured voltages in region Am would best correlate to the expected voltages in region Be ($R_{A-B}$>$R_{A-A}$, $R_{A-C}$, $R_{A-D}$, $R_{A-d1}$, and $R_{A-d2}$), and the measured voltages in region Bm would best correlate to the expect voltages in region Ae ($R_{B-A}$>$R_{B-B}$, $R_{B-C}$, $R_{B-D}$, $R_{B-d1}$, and $R_{B-d2}$). Similarly, the measured voltages in region Cm would best correlate to the expected voltages in region De ($R_{C-D}$>$R_{C-A}$, $R_{C-B}$, $R_{C-C}$, $R_{C-d1}$, and $R_{C-d2}$), and the measured voltages in region Dm would best correlate to the expect voltages in region Ce ($R_{D-C}$>$R_{D-A}$, $R_{D-B}$, $R_{D-D}$, $R_{D-d1}$, and $R_{D-d2}$).

At this point, the lead identification algorithm 120 can inform the clinician about the initial determination and in particular can inform whether the leads/proximal terminals appear to have been connected to the ports to which they were assigned, although this can also occur later, as subsequently explained. If the leads/proximal terminals appear to be connected to the correct IPG or ETS ports (FIG. 12D), the lead identification algorithm 120 may cause the GUI 100 to indicate this fact to the clinician. For example, and although not shown, the GUI 100 may indicate in text that the leads/proximal terminals are correctly connected, or use other types of positive indicators (green indicators, icons, pictures, etc.). The clinician programmer 170 may also make an assessment or calculate a measure of confidence concerning the initial determination, and may display this to the user at the GUI 100. The GUI 100 may also display data underlying the confidence assessment, such as the correlation coefficients shown in table 321.

Likewise, as shown in FIG. 12E, the GUI 100 may indicate an apparent incorrect connection to the clinician, and may further indicate how the lead/proximal terminal connections can be fixed. For example, the GUI 100 may indicate in text "to switch the proximal terminals at ports 1 and 2, and at ports 3 and 4," or use other types of negative indicators (red indicators, icons, pictures, arrows, etc.) to show what the correct connection should be.

It may be the case that the leads/proximal terminals are in fact correctly connected to the ports of the IPG 110 or ETS 150, but that the GUI 100 is incorrect in its assignment. In this case, the GUI 100 may also include an option 324*a* to allow the clinician to alter the assignment of the leads/proximal terminals to match the ports to which they are (correctly) connected. That is, option 324*a* may update the leads interface 106 and the leads assignment interface 112 (FIG. 7) to match the manner in which the leads are actually connected to the ports.

Alternatively, the lead identification algorithm 120 can enable other actions to correct an apparently incorrect connection if possible. For example, upon determining an incorrect connection, and as shown in option 324*b*, the clinician can cause the therapy at the ports to match the incorrect connection by reassigning the electrodes associated with each port. Take the incorrect connection of FIG. 12E as an example. Option 324*b* may remedy the incorrect connection by (re)assigning electrodes E1-E8 to port 2, E9-E16 to port 1, E17-E24 to port 4, and E25-E32 to port 3, to remedy the fact that the leads 90*a* and 90*b* have been switched at ports 1 and 2, and that proximal terminals 94*c*1 and 94*c*2 of lead 90*c* have been switched at ports 3 and 4. Such reassignment of the electrodes to the ports can occur in software. For example, if the clinician enters stimulation parameters relevant to electrodes E1-E8, which in reality correspond in the patient to the location of electrodes E9-E16, the lead identification algorithm 120 can convert such stimulation parameters to affect electrodes E9-E16 before transmitting them to the IPG 100 or ETS 150, etc. The lead identification algorithm 120 may also update the electrode assignment in the leads assignment interface 106 of the GUI 100 (FIG. 7) as well.

Figure 12F:
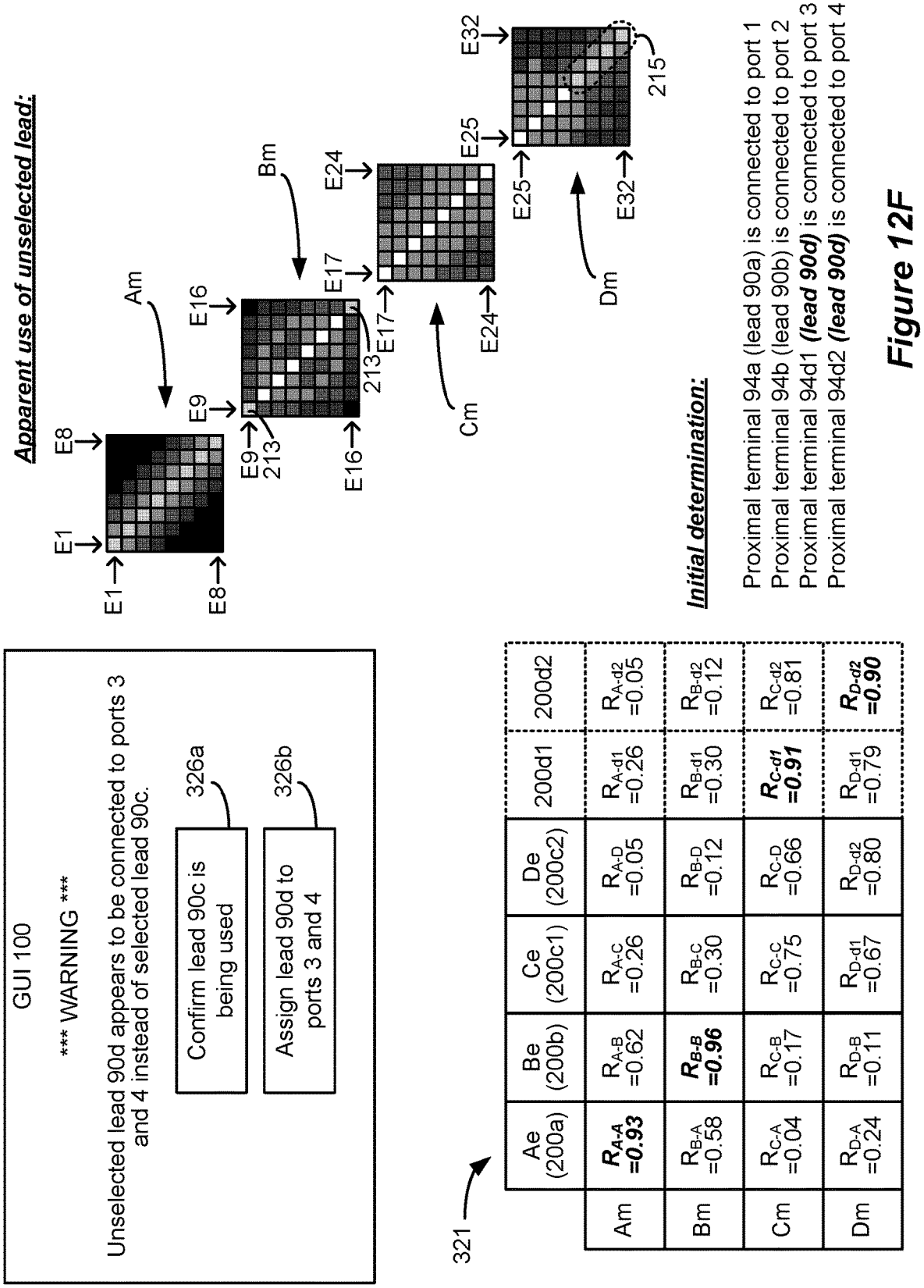

The lead identification algorithm 120 can also at this point inform the clinician whether it appears that a lead supported by the system but not selected in the GUI 100 has been used. In this case, at least one measured voltage region would best correlate with an expected on-diagonal voltage region for an unselected lead. For example, as shown in FIG. 12F, the measured voltages in on-diagonal regions Cm and Dm correlate best with the on-diagonal expected voltages 200*d*1 and 200*d*2 for unselected lead type 90*d*. That is, $R_{C-d1}$ is the highest of the $R_{C-i}$ coefficients and $R_{D-d2}$ is the highest of the $R_{D-i}$ coefficients, suggesting that proximal terminals 94*d*1 and 94*d*2 of lead type 90*d* are connected to ports 3 and 4 of the IPG 110 or ETS 150. In other words, lead 90*d* appears to have been used in the patient instead of lead 90*c*.

If this occurs, the GUI 100 can notify the clinician that incorrect lead type 90*d* appears to be used, as shown in FIG. 12F. The GUI 100 may also present other options in this situation. For example, if the clinician can verify that lead 90*c* is in fact being used in the patient (and therefore that the lead identification algorithm 120 has at least to this point reached a wrong conclusion), the clinician can select an option 326*a* confirming that lead 90*c* is actually being used, effectively overriding the algorithm 120. Alternatively, the selection of the leads in the GUI 100 may be incorrect—i.e., lead 90*d* was meant to be selected in the GUI 100, but lead 90*c* was inadvertently selected instead. The clinician can thus also selection an option 326*b* which will assign the detected lead 90*d* to ports 3 and 4 in the GUI 100.

Although not shown, the GUI 100 may also indicate whether it appears that a particular port of the IPG or ETS seems to lack connection to any lead or proximal terminal. In this regard, if a particular measured on-diagonal region (e.g., Bm, corresponding to electrodes E9-E16) reports only values (Vex) that are zero or near-zero (e.g., below a minimal threshold), the algorithm 120 may conclude that there is no lead/proximal terminal connected to that port (e.g., port 2). Again, the absence of a lead or proximal terminal at a particular port can also be identified to the user via the GUI 100. This can also be useful to the clinician. For example, the clinician may have assigned lead 90*a* to port 1, and has assigned port 2 as unconnected. If the algorithm determines that port 1 appears unconnected, and lead 90*a* appears connected to port 2, the algorithm can notify the clinician of this fact so that lead 90*a* (its proximal terminal 94*a*) can be switched from port 2 to port 1.

In one example, the lead identification algorithm 120—which to this point has only assessed on-diagonal regions—can be complete. This can be sufficient because the on-diagonal expected voltages (200*a*, 200*b*, 200*c*1, 200*c*2, 200*d*1, 200*d*2; see FIG. 10A-10D) can be different enough to differentiate between the various leads and proximal terminals.

However, in a preferred embodiment, off-diagonal regions are also considered. This is especially useful when leads such as 90*c* and 90*d* are used having larger numbers of electrodes (sixteen) than each IPG 100 or ETS 150 port (eight) supports, and therefore when such leads have more than one proximal terminal. Consideration in the lead identification algorithm 120 of off-diagonal regions can help resolve ambiguities that might arise when only on-diagonal regions are assessed, because expected voltages in off-diagonal regions (e.g., 200*c*3, 200*c*4, 200*d*3, 200*d*4) provide additional information to make the lead—(or proximal terminal-) to-port determination more precise. Further, consideration of off-diagonal regions is useful to identify which ports the two eight-electrode proximal terminals of a sixteen-electrode lead are connected to, which might otherwise be confusing, as explained further below.

Figure 13A:
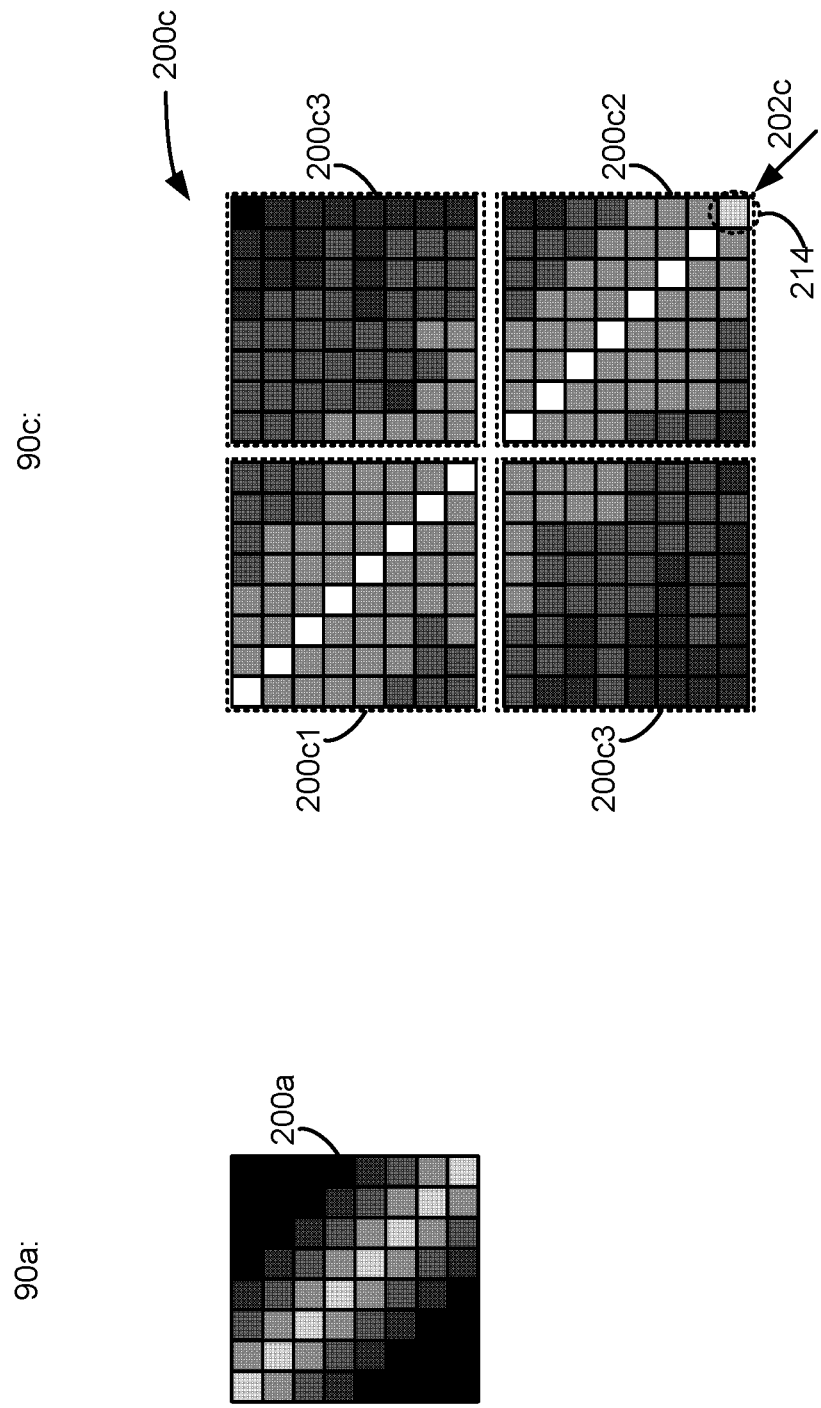
FIGS. 13A-13C show various ambiguities that can result if the lead identification algorithm operates using analysis of only on-diagonal regions.
Figure 13B:
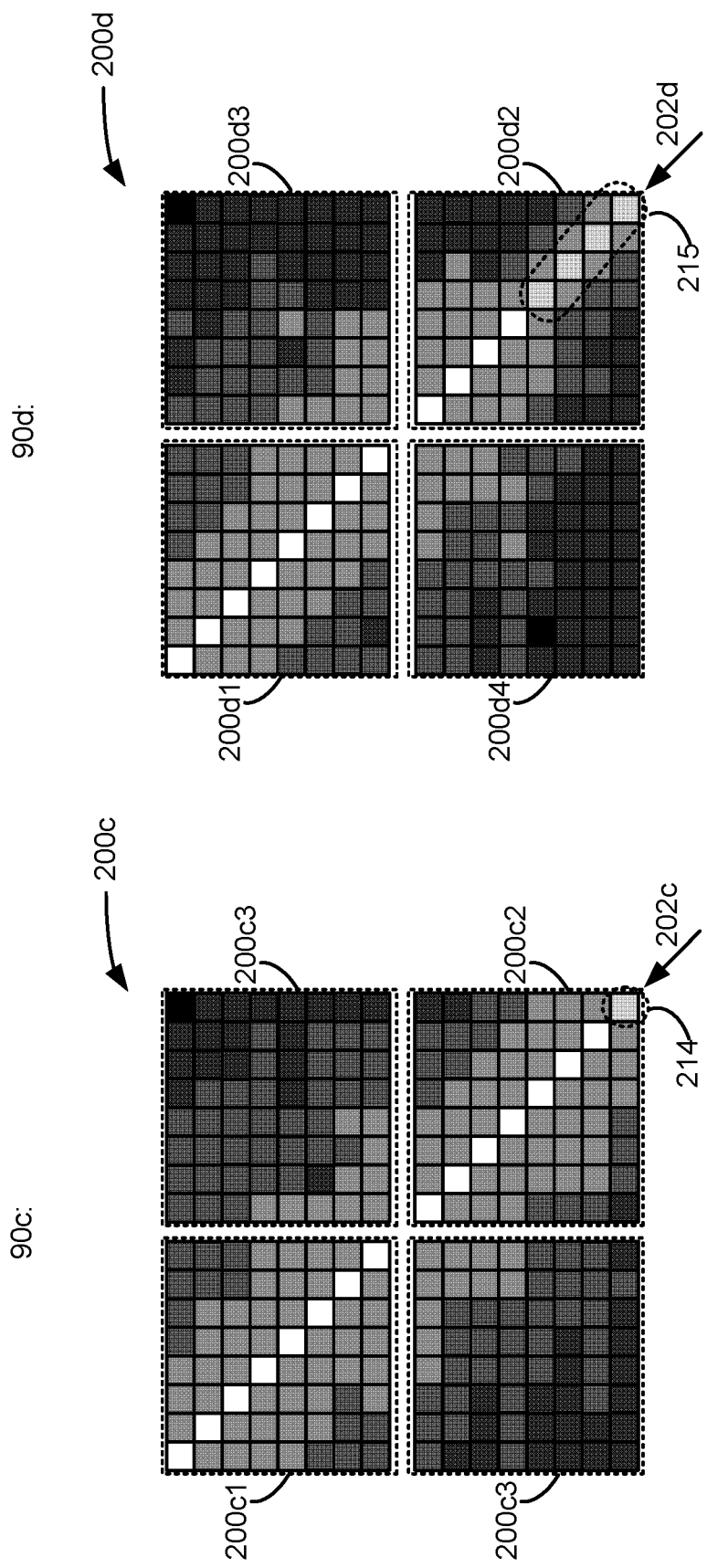
Figure 13C:
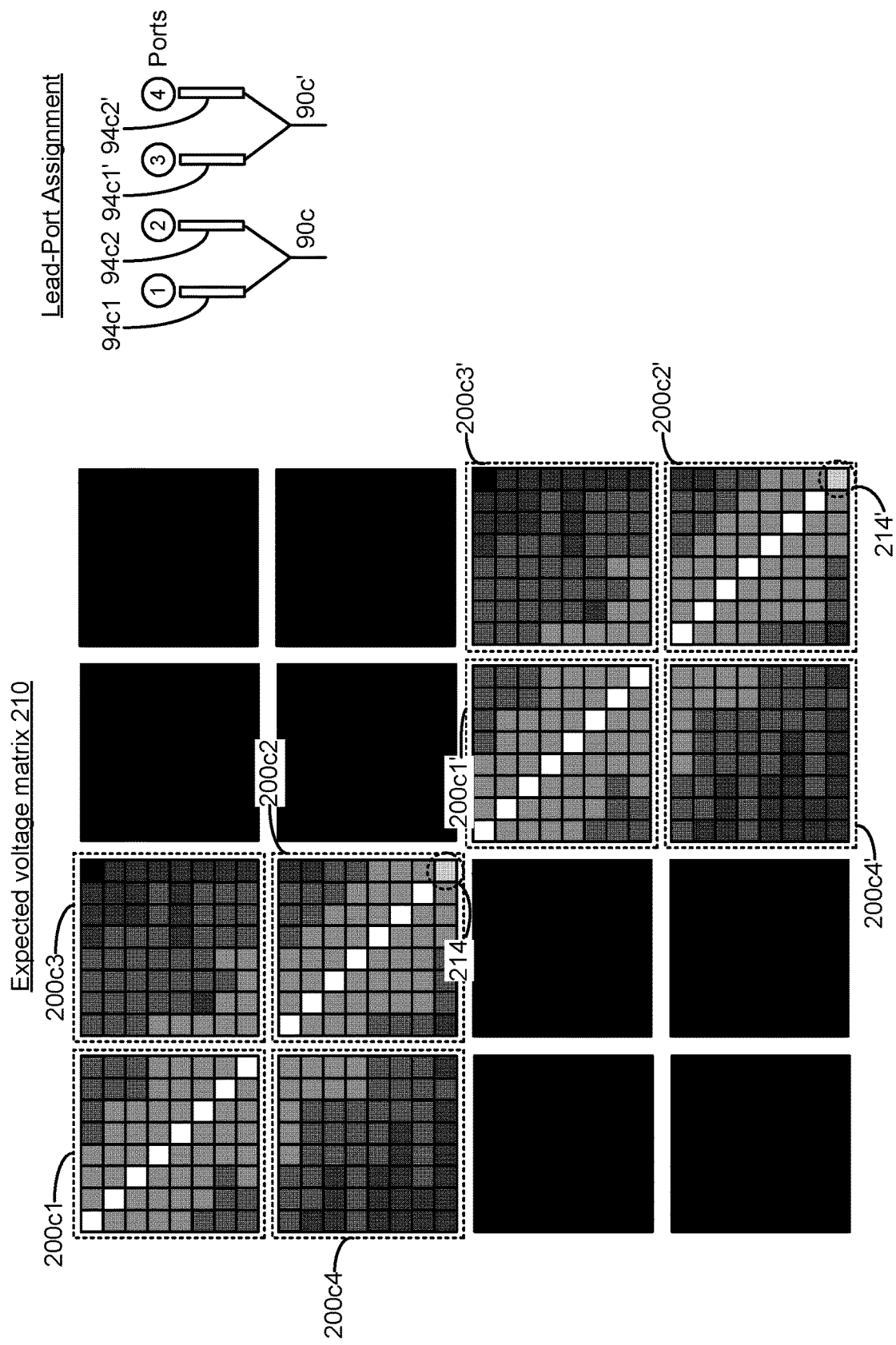

FIGS. 13A-13C show ambiguities that can result if lead identification algorithm 120 is limited to consideration of on-diagonal regions alone. Consider FIG. 13A, which shows the expected voltages 200*a* for eight-electrode lead type 90*a* (FIG. 10A), and expected voltages 200*c* for sixteen-electrode lead type 90*c* (FIG. 10C). Particularly if the voltage magnitudes are normalized, expected voltages 200*a* may not appear substantially different from on-diagonal expected voltages 200*c*1, corresponding to proximal terminal 94*c*1 of lead 90*c*. This creates potential ambiguity (see step 320, FIG. 12C) regarding whether measured on-diagonal voltages would best correlate to lead 90*a*, or to proximal terminal 94*c*1 of lead 90*c*. This may cause an on-diagonal analysis to conclude that lead type 90*a* is connected to a particular port when in reality proximal terminal 94c1 of lead type 90c is connected to the port, or vice versa.

FIG. 13A illustrates yet another potential ambiguity. For lead type 90c, the expected voltages from on-diagonal regions 200c1 and 200c2 may be hard to resolve. These regions may vary most significantly with respect to a single element 214. This creates potential ambiguity regarding whether measured on-diagonal voltages would best correlate to proximal terminal 94c1 of lead 90c (200c1) or proximal terminal 94c2 of lead 90c (200c2). This may cause an on-diagonal analysis to conclude that proximal terminal 94c1 is connected to a particular port and that proximal terminal 94c2 is connected to a different port, when in reality these proximal terminals 94c1 and 94c2 are flipped at these ports. This is also true for lead type 90d, whose on-diagonal regions 200d1 and 200d2 most significantly vary with respect to elements 215 (FIG. 10D). This again makes it possible for an on-diagonal analysis to confuse which of proximal terminals 94d1 and 94d2 might be connected to which ports.

FIG. 13B illustrates yet another potential ambiguity, and shows the expected voltages for sixteen-electrode lead types 90c (200c) and 90d (200d). Generally speaking, the expected voltages from on-diagonal regions 200c1 and 200c2, and 200d1 and 200d2, may be hard to resolve. Expected voltages 200c1 and 200d1 are largely similar, which could occur if electrodes E1-E8 of lead 90c and 90d are identical in the shape, size, and orientation at the distal ends of the leads (although electrodes E9-E16 may differ). As for on-diagonal regions 200c2 and 200d2, these regions may vary most significantly with respect to elements 214 and 215. This creates potential ambiguity regarding whether measured on-diagonal voltages would best correlate to proximal terminals 94c1 and 94c2 of lead 90c or to proximal terminals 94d1 and 94d2 of lead 90d, which again raises the potential of an improper initial determination of lead-to-port connection if on-diagonal analysis alone is used.

FIG. 13C illustrates yet another potential ambiguity related to the use of sixteen-electrode leads. In this example, two of the same sixteen-electrode leads 90c (90c and 90c') are to be used, and the expected voltage matrix 210 for this assignment is shown. In this example, proximal terminal 94c1 of lead 90c is assigned to port 1, and proximal terminal 94c2 of lead 90c is assigned to port 2. Further, proximal terminal 94c1' of lead 90c' is assigned to port 3, and proximal terminal 94c2' of lead 90c' is assigned to port 4. Especially given the use of the same lead, it may be difficult to tell using measured on-diagonal regions which proximal terminal of which lead is connected to which port. For example, on-diagonal expected voltages 200c1 and 200c1' of leads 90c and 90c' are identical. This makes is difficult to tell whether proximal terminal 94c1 of lead 90c or proximal terminal 94c1' of lead 90c' is connected to ports 1 or 3. Likewise, on-diagonal expected voltages 200c2 and 200c2' of leads 90c and 90c' are identical, making it difficult to tell whether proximal terminal 94c2 of lead 90c or proximal terminal 94c2' of lead 90c' is connected to ports 2 or 4. This same ambiguity is also present if lead types 90c and 90d are used, which are similar as noted earlier (FIG. 13B).

These potential ambiguities of FIGS. 13A-13C are further exacerbated if the measurements are noisy. Given these potential ambiguities, it is preferred that lead identification algorithm 120 also consider measured off-diagonal regions. Continuation of the lead identification algorithm 120 to consider such off-diagonal regions starts with FIG. 14A. Step 340 starts with identifying measured off-diagonal regions that have significant voltage data. This can occur in several different manners. In one example not shown, each of the measured off-diagonal regions (ABm, ACm, etc.) can be determined as having significant voltage data if any of (or some significant amount of) their elements comprises a significantly high voltage.

In the example shown, and preferably, determining whether each off-diagonal region comprises significant voltage data occurs by averaging the voltage elements in each 8×8 off-diagonal region, and comparing them to a threshold. If the average for a given measured off-diagonal region is above the threshold, then that off-diagonal region is determined to have significant voltage data, and is considered further in the analysis.

In a preferred example, the threshold used to gauge the significance of each measured off-diagonal region may be different, and may be determined in accordance with the measured on-diagonal regions to which they correspond. Take for example an analysis of measured off-diagonal region ACm. The magnitude of any voltages in this off-diagonal region would be expected to vary in accordance with the magnitude of the voltage values in corresponding on-diagonal regions Am and Cm. According, the threshold by which off-diagonal region ACm is measured can be determined using an average of the magnitude of the voltages values in regions Am and Cm, i.e., AVG(Am+Cm). Further, because the voltage values in these on-diagonal regions Am and Cm would generally be higher than the voltage values in the off-diagonal regions, the threshold used to determine the significance of off-diagonal region ACm could be compared to a scalar of AVG(Am+Cm), i.e., x*AVG(Am+Cm), where x is a scalar of less than one. In short, off-diagonal measured region ACm will be deemed significant and will be consider further in the lead identification algorithm 120 if AVG(ACm)>x*AVG(Am+Cm).

This same significance analysis can proceed for all of measured off-diagonal regions, as shown in table 342. Note that due to symmetry inherent in the system, the average measured voltage values in a given off-diagonal region (e.g., ACm) should generally be the same as the average in the corresponding off-diagonal region (e.g., CAm). Accordingly, step 340 may assess significance of only the measured off-diagonal regions on one side of the diagonal of the measured voltage matrix 190, for example those on the top right of the diagonal (i.e., ABm, ACm, ADm, BCm, BDm, and CDm). If a particular assessed region is deemed significant (e.g., ACm), then so is its corresponding region (e.g., CAm). Having said this, step 340 may also independently assess all off-diagonal regions for significance. In still a further alternative not shown, the average of the voltage magnitudes in both corresponding measured off-diagonal regions can be compared to the relevant threshold, e.g., AVG(ACm+CAm)>x*AVG(Am+Cm).

Figure 14A:
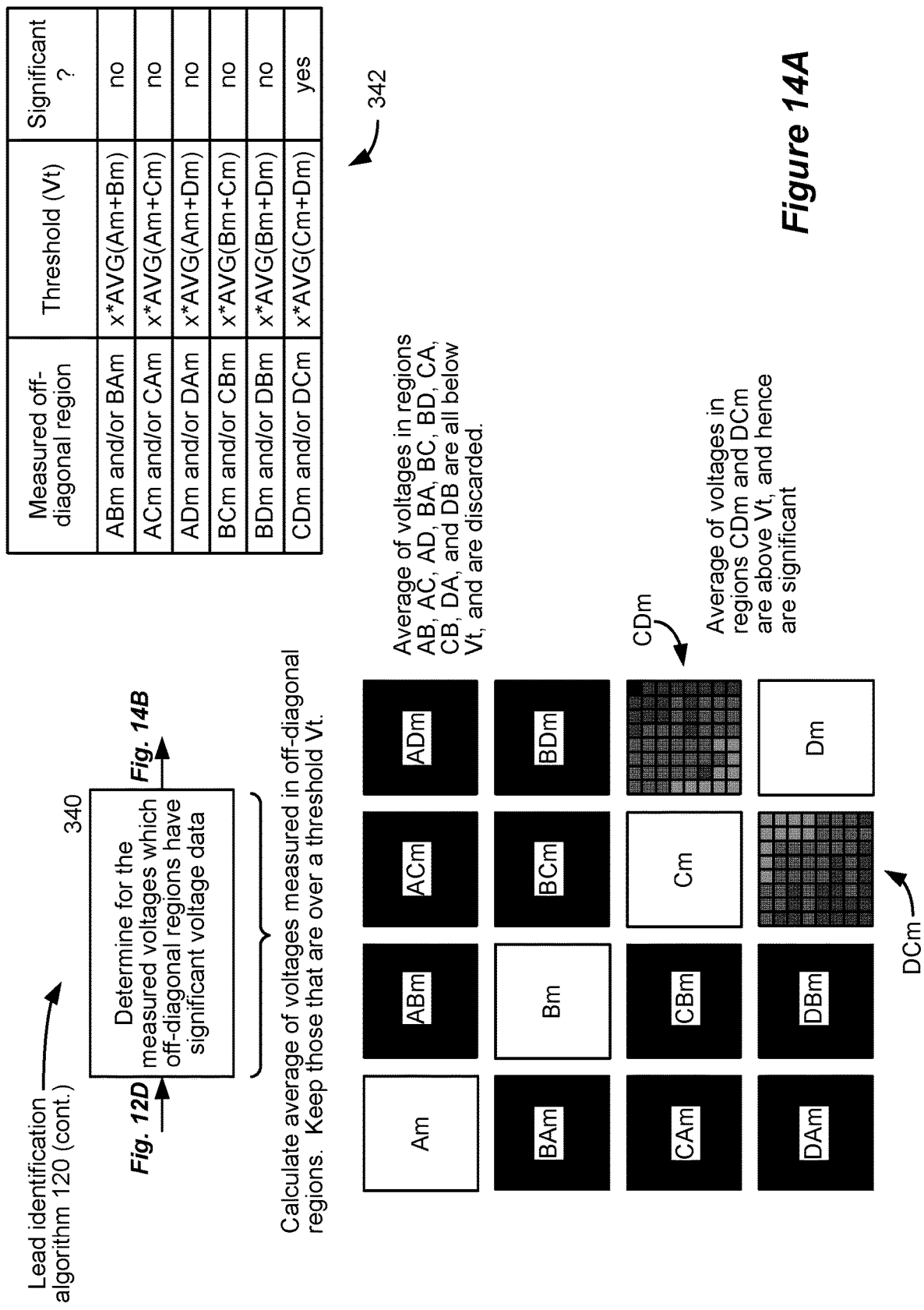

In FIG. 14A, the measured off-diagonal regions are assessed assuming the leads are connected as prescribed earlier (FIG. 7), with lead 90a connected to port 1, lead 90b connected to port 2, and proximal terminals 94c1 and 94c2 of lead 90c connected to ports 3 and 4 respectively. In this situation, it is seen that only measured off-diagonal regions CDm and DCm have significant voltage values, and therefore, only these off-diagonal regions will be consulted further.

Figure 14B:
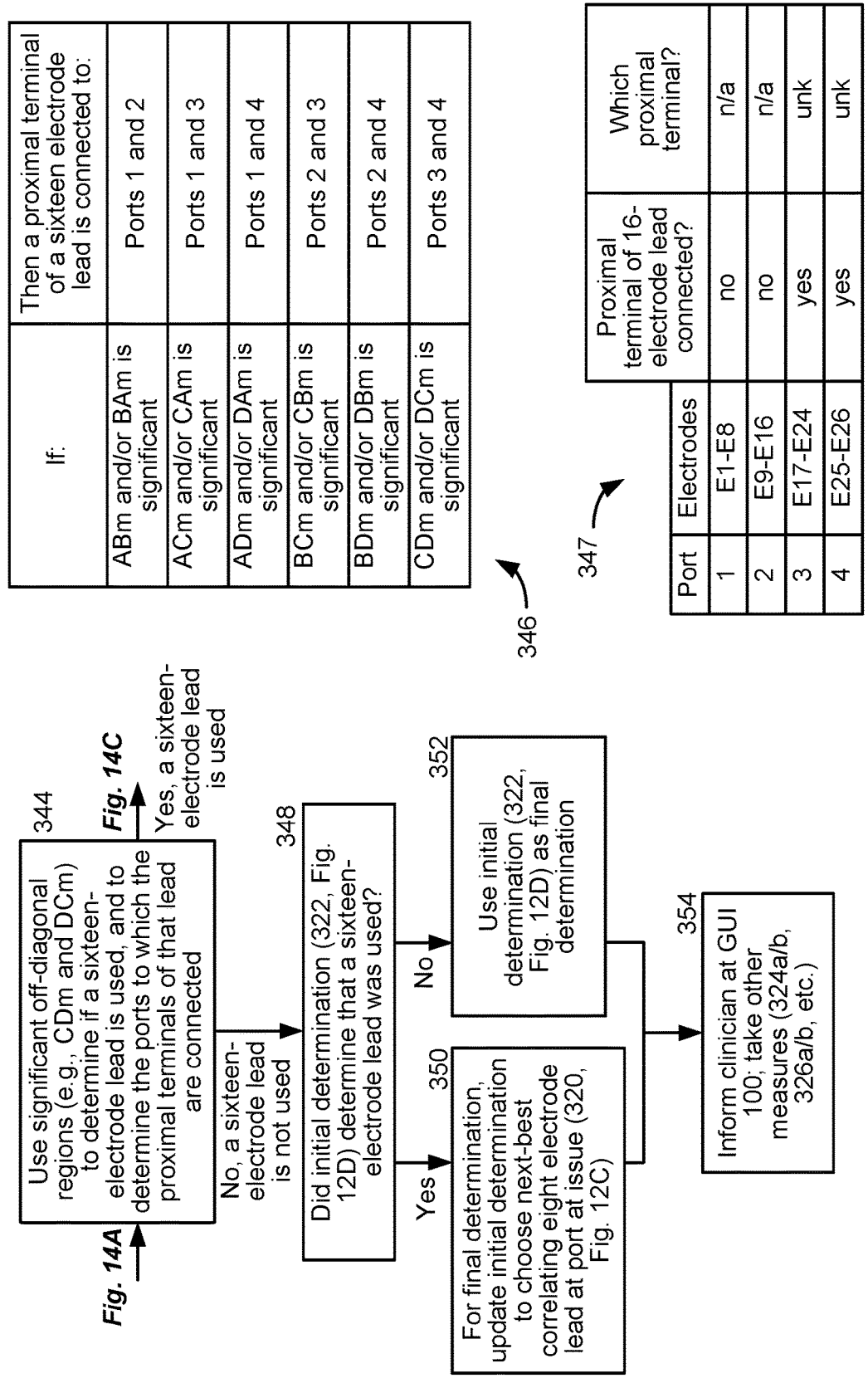

In a next step 344 shown in FIG. 14B, the identified significant measured off-diagonal regions are used to determine whether a sixteen-electrode lead (such as 90c or 90d) is used, and to determine to which ports that lead's two proximal terminals are connected. Logic used in this determination is summarized in table 346. Because regions A correspond to electrodes E1-E8, significance of regions AXm or XAm will mean that a sixteen-electrode lead is being used, and that one of its two proximal terminals is connected to port 1. Likewise, because regions B correspond to electrodes E9-E16, significance of regions BXm or BAm will mean that a sixteen-electrode leads is being used, and that one of its two proximal terminals is connected to port 2, etc. From this, it can be determined as per table 346—where CDm and DCm are significant—that proximal terminals (e.g., 94c1 and 94c2) of a sixteen-electrode lead (e.g., 90c) are coupled to ports 3 and 4.

Table 347 shows the results of step 344. It shows that a sixteen-electrode lead does not appear to be connected to ports 1 or 2, but that a sixteen-electrode lead is connected to ports 3 and 4. However, at this point it may be unclear which sixteen-electrode lead is connected (e.g., 90c or 90d) or which proximal terminal (e.g., 94c1 or 94c2) is connected to which of ports 3 or 4, even though an initial determination was made based on on-diagonal analysis alone (322, FIG. 12D). Subsequent steps of the lead identification algorithm 120 help to resolve this ambiguity.

If a sixteen-electrode lead is not identified at step 344, then algorithm 120 inquires at step 348 whether a sixteen-electrode lead was identified as used during the initial determination when only on-diagonal regions were considered. Note that this is possible, because as noted earlier (FIG. 13A), it can be difficult to distinguish between the proximal terminals of eight- and sixteen-electrode leads when considering on-diagonal regions alone. Consider FIG. 12D again. It may have been the case that the initial determination determined that measured voltages Bm at port 2 best correlated to proximal terminal 94d1 (200d1) of lead 90d, because a highest correlation coefficient ($R_{B\text{-}d1}$) was observed as corresponding to Bm, when in reality lead type 90b is connected to port 2. If however step 344 determines that no sixteen-electrode lead is used, then in step 350 the initial determination can be updated as the final determination with a next-best correlating eight-electrode lead type. For example, the comparison matrix 321 (FIG. 12C) can be consulted again to determine whether $R_{A\text{-}A}$ or $R_{A\text{-}B}$—correlation coefficients for eight-electrode lead types 90a and 90b—is highest for region Bm, and the final determination will reflect that. If $R_{B\text{-}B}$ is highest (as would be expected if lead type 90b is connected to port 2), then the final determination at step 350 will reflect use of this lead at this port.

If the initial determination did not determine that a sixteen-electrode was used (348), then the initial lead-to-port determination arrived at earlier using only on-diagonal regions (step 322, FIG. 12D) can be used as a final lead-to-port determination (step 352). At this point (and if this has not occurred already), the lead identification algorithm 120 can inform the clinician of the final determination as described earlier with respect to FIGS. 12D-12F (step 354). Further, if the lead-to-port determination does not match expected results as assigned in the GUI 100 (FIG. 7), the GUI can allow the clinician to take corrective measures, such as those described earlier (see options 324a, 324b, 326a, 326b in FIGS. 12E and 12F).

Figure 14C:
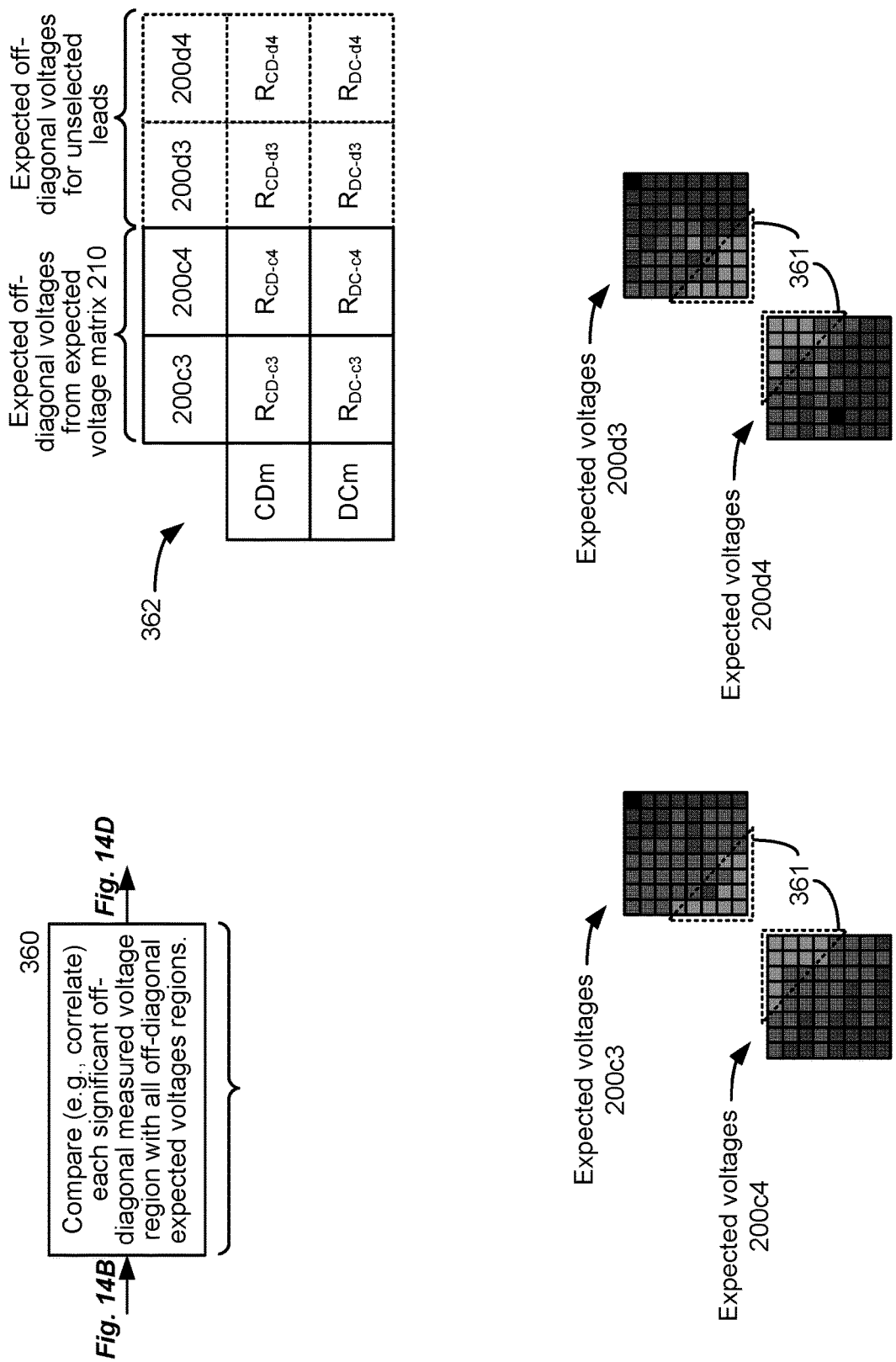

If a sixteen-electrode lead is identified at step 344, it may be unclear which lead (90c or 90d) or which of its proximal terminals (e.g., 94c1 and 94c2) are connected to ports 3 and 4. Again, an initial determination of the proximal terminals connected to ports 3 and 4 was made earlier during the lead identification algorithm 120 (e.g., 322 FIG. 12D), but as pointed out earlier with respect to FIGS. 13B-13C, it may be difficult to differentiate between sixteen-electrode leads or their two sets of proximal terminals using an analysis of on-diagonal regions alone. FIG. 14C attempts to resolve this potential ambiguity by analysis of the significant off-diagonal regions. As shown in step 360, the significant measured off-diagonal regions are compared to off-diagonal expected voltages. Relevant off-diagonal expected voltages were identified earlier in FIG. 12A, and comprise expected voltages 200c3 and 200c4 forming part of the expected voltage matrix 210, and may additionally comprise off-diagonal expected voltages 200d3 and d4 from unselected lead type 90d. Again, consideration of expected voltages such as 200d3 and 200d for unselected leads may not be necessary, but is useful to potentially determine whether the clinician has used an incorrect lead type with the patient.

In FIG. 14C, each of the significant off-diagonal measured regions (e.g., CDm and DCm) are compared against the off-diagonal expected voltages 200c3, 200c4, and optionally 200d3 and 200d4. Again, this comparison may comprise the computation of correlation coefficients R, as shown in table 362, and as before such comparison can occur in many different ways.

Figure 14D:
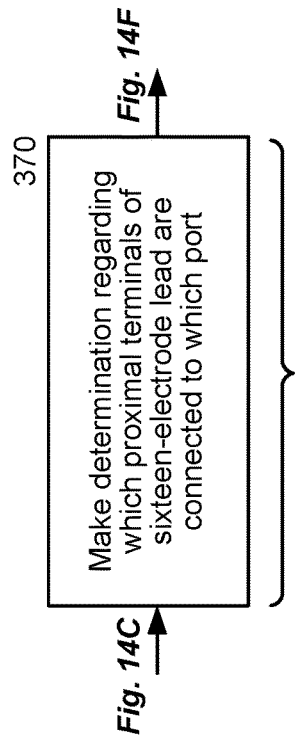
Figure 14D:
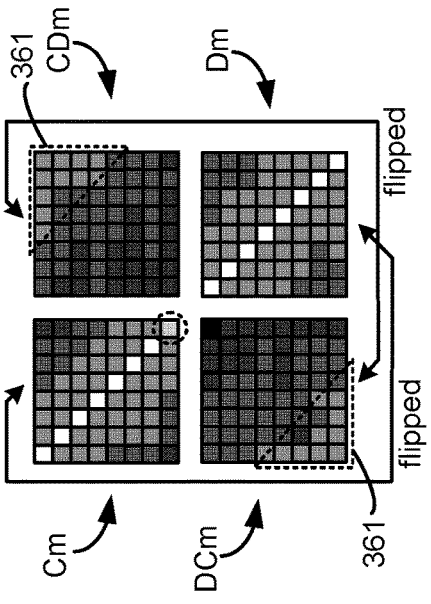
Figure 14D:
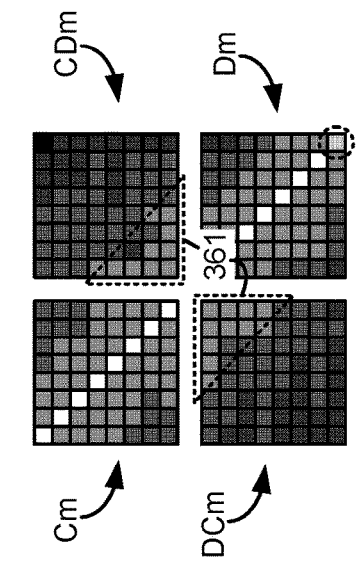

As will be seen in FIG. 14D, the comparison of measured and expected off-diagonal voltages is particularly useful to determine if the proximal terminals of the sixteen-electrode lead have inadvertently been switched at the ports. This situation is readily detectable because higher voltage elements 361 in the off-diagonal expected voltage matrices 200c3, 200c4, 200d3, and 200d4 occur in different positions. For example, in expected voltage matrices 200c3 and 200d3, high voltage elements 361 occur at the bottom left of the matrices; in expected voltage matrices 200c4 and 200d4, high voltage elements 361 occur at the top right of the matrices.

FIG. 14D shows in step 370 how the lead identification algorithm 120 determines which proximal terminals of which sixteen-electrodes lead are connected to the identified ports. Such determination reviews the various correlation coefficients in table 362 to find the highest correlation coefficient (best match) for each significant measured off-diagonal region (e.g., CDm and DCm). FIG. 14D shows resulting correlation coefficients for an apparently correct connection (left) and an apparently incorrect connection (right). Starting with the apparently correct connection, significant measured off-diagonal region CDm best correlates with expected voltages 200c3 (0.92) and DCm best correlates with expected voltages 200c4 (0.89), suggesting that the sixteen-electrode lead connected to ports 3 and 4 is lead type 90c rather than lead type 90d. In short, the additional expected voltage information provided by the off-diagonal regions can ease determination as to the correct sixteen-electrode lead type. As discussed earlier (see FIG. 13B), this can be difficult to determine when using on-diagonal analysis alone.

Notice also that CDm correlates well with expected voltages 200c3 (0.92) and poorly with expected voltages 200c4 (0.13) of lead type 90c. Similarly, DCm correlates poorly with expected voltages 200c3 (0.25) and well with expected voltages 200c4 (0.89) of lead type 90c. This is expected due to the different positions of the high voltage elements 361 in 200c3 and 200c4, and helps to resolve the potential ambiguity as to which port each set of proximal terminals 94c1 (port 3) and 94c2 (port 4) is connected. As discussed earlier (see FIG. 13A), differentiating between the proximal terminals of a sixteen-electrode lead can also be difficult to determine when using on-diagonal analysis alone.

The right of FIG. 14D shows an apparent incorrect connection. Here, CDm correlates well with expected voltages 200c4 and poorly with expected voltages 200c3, and DCm correlates poorly with expected voltages 200c3 and well with expected voltages 200c4. This informs that the proximal terminals are switched: proximal terminal 94c2 is connected to port 3, and proximal terminal 94c1 is connected to port 4.

In short, via step 370, it is now clear which sixteen-electrode lead (e.g. 90c) is connected to the identified ports 3 and 4, and more particularly which of that lead's proximal terminals is connected to those ports (94c1 and 94c2 respectively, assuming a correct connection). FIG. 14E shows table 347 as updated with this information.

At this point, the lead identification algorithm 120 can at step 380 revise the initial determinations concerning lead-to-port connections made earlier on the basis of on-diagonal region analysis alone (322, FIG. 12D). Two different revisions of the initial determinations are illustrated. In revision 380a, the initial determination using on-diagonal analysis was that proximal terminals 94c2 and 94c1 of lead type 90c are respectively connected to ports 3 and 4. However, after comparison of off-diagonal regions CDm and DCm (FIG. 14D) to other off-diagonal expected voltage regions, it is clear that proximal terminals 94c1 and 94c2 are respectively connected to ports 3 and 4, i.e., that the initial determination should be revised at ports 3 and 4.

In revision 380b, it is assumed in the initial determination using on-diagonal analysis that proximal terminals 94a of eight-electrode leads 90a are connected to ports 1 and 3, that proximal terminal 94b of eight-electrode lead 90b is connected to port 2, and that a proximal terminal 94d2 of lead 90d is connected to port 4. Note that this initial determination should be clearly incorrect, as it does not account for the other proximal terminal 94d1 of lead 90d, which should be connected. After review of the off-diagonal regions, it will become clear that a sixteen-electrode lead is connected to ports 3 and 4 (i.e., not eight-electrode lead 90a), and the further information provided by the off-diagonal regions (as compared at step 370) may make it clear that the lead type used is lead 90c, not 90d. Further, due to the location of high voltage elements 361 in 200c3 and 200c4, it is further clear which of lead 90c's proximal terminals 94c1 and 94c2 are connected to port 3 and 4.

At this point, the lead identification algorithm 120 can inform the clinician of the results as described earlier (step 382), and if the lead—(or proximal terminal-) to-port determination does not match expected results as assigned in the GUI 100 (FIG. 7), the GUI can allow the clinician to take corrective measures, such as those described earlier (see options 324a, 324b, 326a, 326b in FIGS. 12E and 12F). As with the initial determination, the clinician programmer 170 may also make an assessment or calculate a measure of confidence concerning the final determination, and may display this to the user at the GUI 100, and may also display data underlying the confidence assessment, such as the various correlation coefficients. As before, the GUI 100 can also indicate the absence of a lead or proximal terminal at a particular port.

Consideration of off-diagonal regions is also useful to help resolve the ambiguity when two of the same sixteen-electrode lead type are used, as discussed earlier with respect to FIG. 13C. In that example, two of the same sixteen-electrode leads 90c (90c and 90c') are used, with proximal terminal 94c1 of lead 90c assigned to port 1, proximal terminal 94c2 of lead 90c assigned to port 2, proximal terminal 94c1' of lead 90c' assigned to port 3, and proximal terminal 94c2' of lead 90c' assigned to port 4. The algorithm 120 would not be able to readily differentiate between these leads using only the on-diagonal analysis, because the expected voltages for each would look the same, as shown in FIG. 13C.

Figure 15:
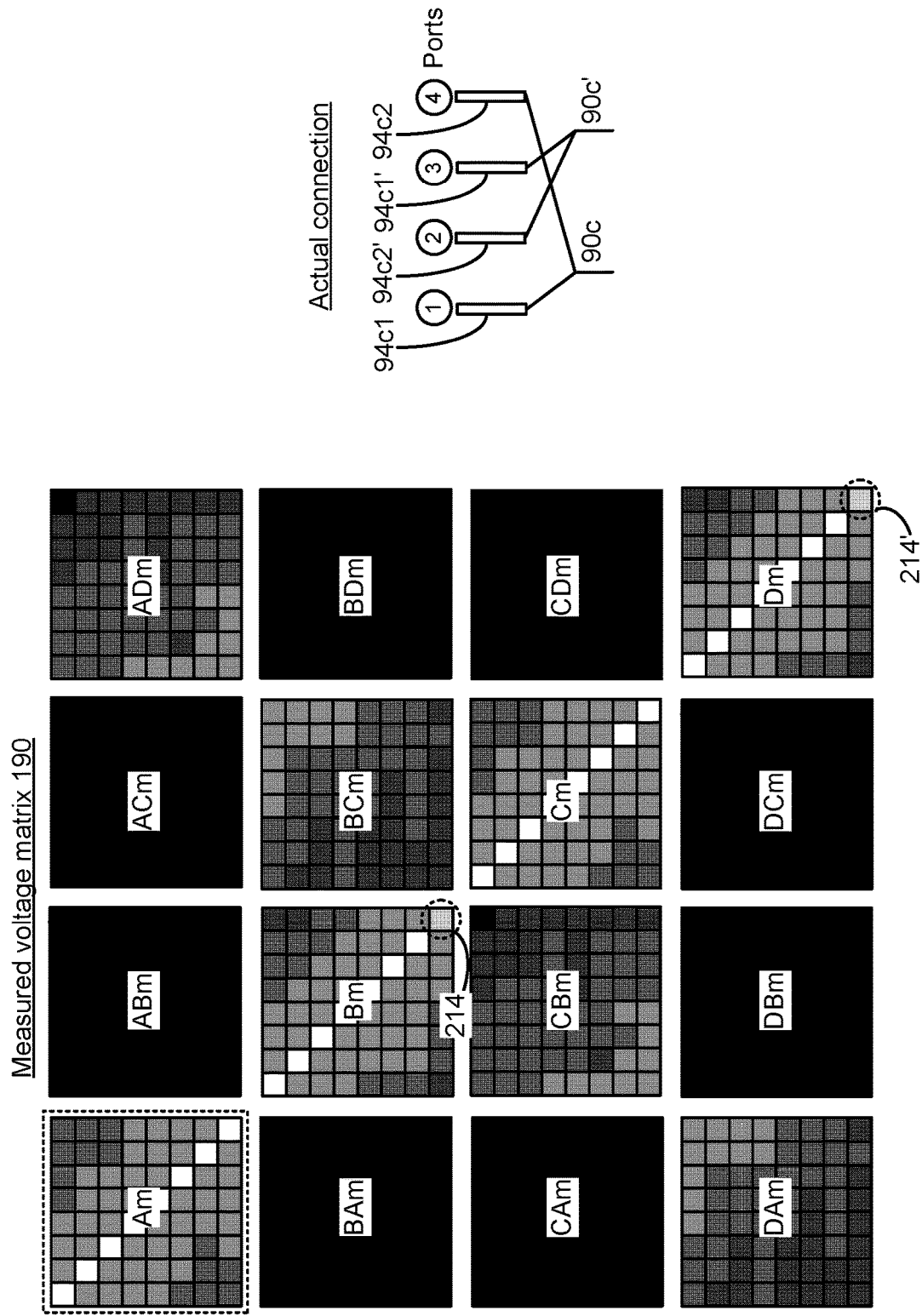
FIG. 15 shows a measured voltage matrix for two sixteen-electrode leads having two of their proximal terminals flipped at ports of an IPG or ETS.

However, the algorithm 120 would be able to determine if the proximal terminals of these leads 90c and 90c' have been swapped at the ports, as shown in FIG. 15. FIG. 15 shows the measured voltage matrix 190 for the two leads 90c and 90c' if proximal terminals 94c1 and 94c1' are swapped at ports 2 and 4. In this circumstance, the algorithm would identify off-diagonal regions DAm, CBm, BCm, and ADm as significant, and thus determine that two sixteen-electrode leads are being used (step 344). Further, the algorithm would determine using corresponding off-diagonal regions ADm and DAm that one sixteen-electrode lead is connected to ports 1 and 4, and likewise determine using corresponding off-diagonal regions CBm and BCm that the other sixteen-electrode lead is connected to ports 2 and 3. Further, the comparison of these off-diagonal regions (step 360) would make it clear that proximal terminal 94c1 of one lead is connected to port 1 while its other proximal terminal 94c2 is connected to port 4. Still further, the comparison of these off-diagonal regions would make it clear that proximal terminal 94c1' of the other lead 90c' is connected to port 3 while its other proximal terminal 94c2' is connected to port 2.

To this point in the disclosure, it has been assumed that the lead identification algorithm 120 operates to determine whether the leads (proximal terminals) are properly connected to IPG or ETS ports as assigned in the GUI 100 (FIG. 7). However, in an alternative example, the algorithm can operate to simply detect the leads (proximal terminals) that have been connected to the IPG or ETS even if such leads (proximal terminals) have not been preassigned to particular ports in the GUI.

Figure 16B:
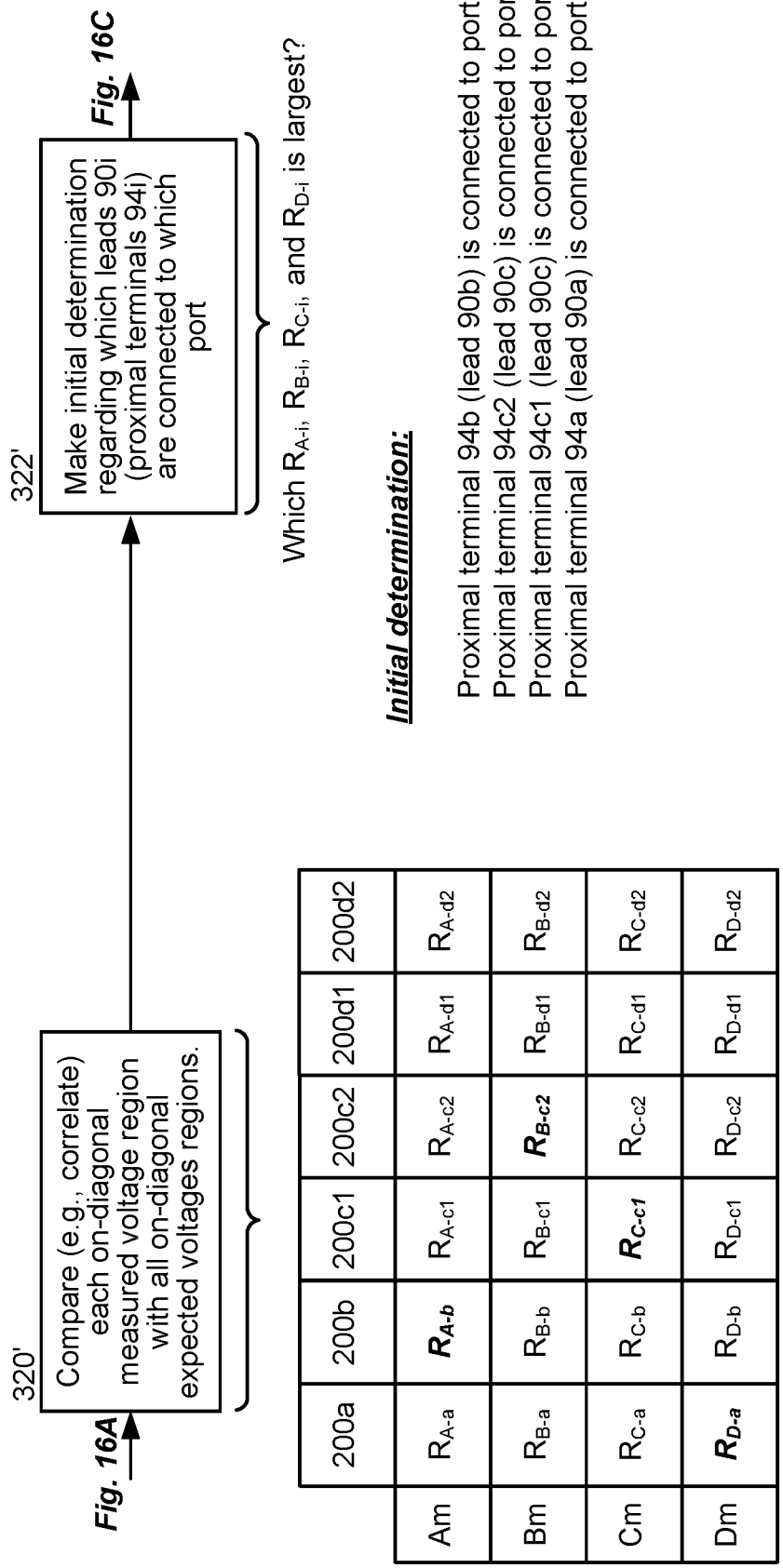

The alternative example of lead identification algorithm 120' is shown in FIGS. 16A-16E, and for purpose of illustration assumes as shown in the upper right of FIG. 16A that the following leads (proximal terminals) have been connected to the IPG or ETS ports: lead 90b (proximal terminal 94b) is connected to port 1 (electrodes E1-E8); proximal terminal 94c2 of lead 90c is connected to port 2 (electrodes E9-E16); proximal terminal 94c1 of lead 90c is connected to port 3 (electrodes E17-E24); and lead 90a (proximal terminal 94a) is connected to port 4 (electrodes E25-E32). Although not shown, it should be understood that algorithm 120' can be enabled by providing an "Identify Lead Connection" option 122' (as opposed to a "Verify Lead Connection" option 122; FIG. 7) in the GUI 100. As with algorithm 120', it is not strictly required to perform the steps of algorithm 120' in the order illustrated Steps similar to those described earlier are denoted with the same element numerals, although designated with a prime symbol ('). Starting with step 302', the algorithm 120' retrieves from memory in the clinician programmer 170 expected voltages 200i for the various lead types 90i supported by the system. As before, the retrieved expected voltages 200i may comprise only those for leads 90i that can operate with the IPG or ETS in question. In step 305', the expected voltages are designated as on-diagonal or off-diagonal regions (211). The expected voltages 200a and 200b of leads such as 90a and 90b having only eight electrodes will be designated as on-diagonal regions. Leads such as 90c and 90d having sixteen electrodes and two proximal terminals will have two on-diagonal regions (200c1/200c2 and 200d1/200d2) and two off-diagonal regions (200c3/200c4 and 200d3/200d4). The expected voltages 200i can be preprocessed at step 306' as described earlier.

In step 310', the measured voltage matrix 190 is received, and in step 312' is divided into on- and off-diagonal regions. These measured voltages can be preprocessed at step 314', again as explained earlier.

FIG. 16B begins steps relevant to the analysis of the on-diagonal regions. In step 320', each on-diagonal voltage region (Am-Dm) is compared with all on-diagonal expected voltages regions (200a, 200b, 200c1, 200c2, 200d1, and 200d2), which again can comprise determination of a correlation coefficient R for each comparison, as reflected in table 321'. From this, an initial determination can be made (step 322') as to which lead or proximal terminal appears to be connected to each of the ports. By way of review, this is determined by identifying a largest correlation coefficient for each of the measure regions. In FIG. 16B, it is assumed via the bolded correlation coefficients that the algorithm 120' has correctly identified the leads/proximal terminals as specified by the connections of FIG. 16A. However, as noted earlier, such an initial determination can be incorrect, and analysis of measured off-diagonal regions can be warranted.

Figure 16C:
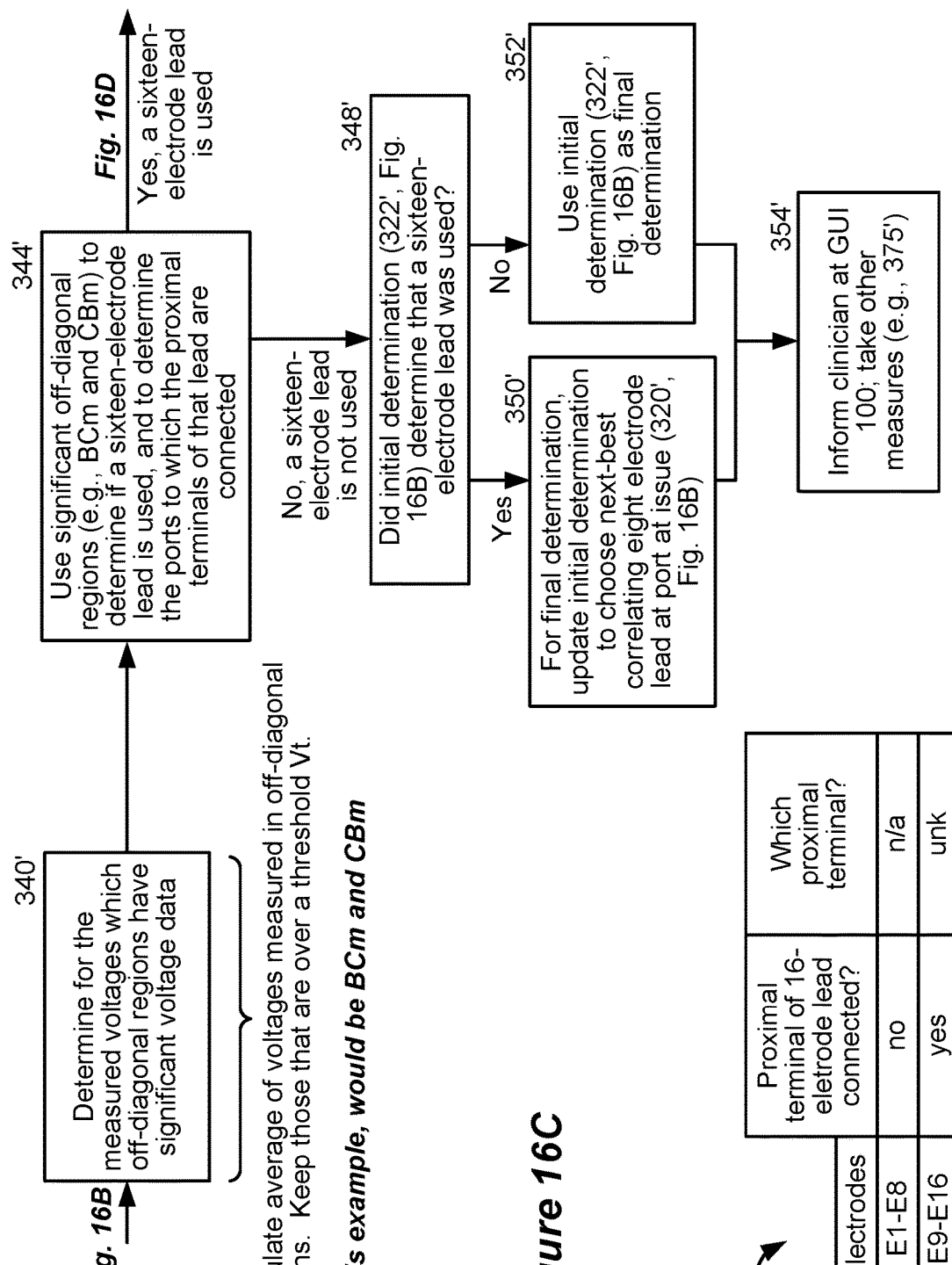

FIG. 16C begins steps relevant to the analysis of the off-diagonal regions. In step 340', significant measured off-diagonal regions are determined, such as by comparing the average of the voltage elements in each region to a threshold as described earlier. In the illustrated example, only measured off-diagonal regions BCm and CBm would have significant voltages, because only one sixteen-electrode lead 90c is used, and is connected to ports 2 and 3. In step 344', the significance of regions BCm and CBm would make clear that a sixteen-electrode leads is being used, and that its proximal terminals are connected to ports 2 and 3, as shown in the table 347'. As before, if no off-diagonal measured regions are significant, the algorithm 120' reaches the conclusion that no sixteen-electrode leads are used. At this point, the algorithm 120' can double check whether the initial determination (322', FIG. 16B) identified a sixteen-electrode lead type at a particular port (348'). If so, the final determination updates the initial determination at that port with the next-best-correlating eight-electrode lead (step 350'). If not, the initial determination is used as the final determination (352'). At this point, the GUI 100 could inform the clinician concerning which leads or proximal terminals appear to be connected to which ports (354'). The GUI 100 may also allow the clinician to take other actions, such as 375', explained subsequently.

Figure 16D:
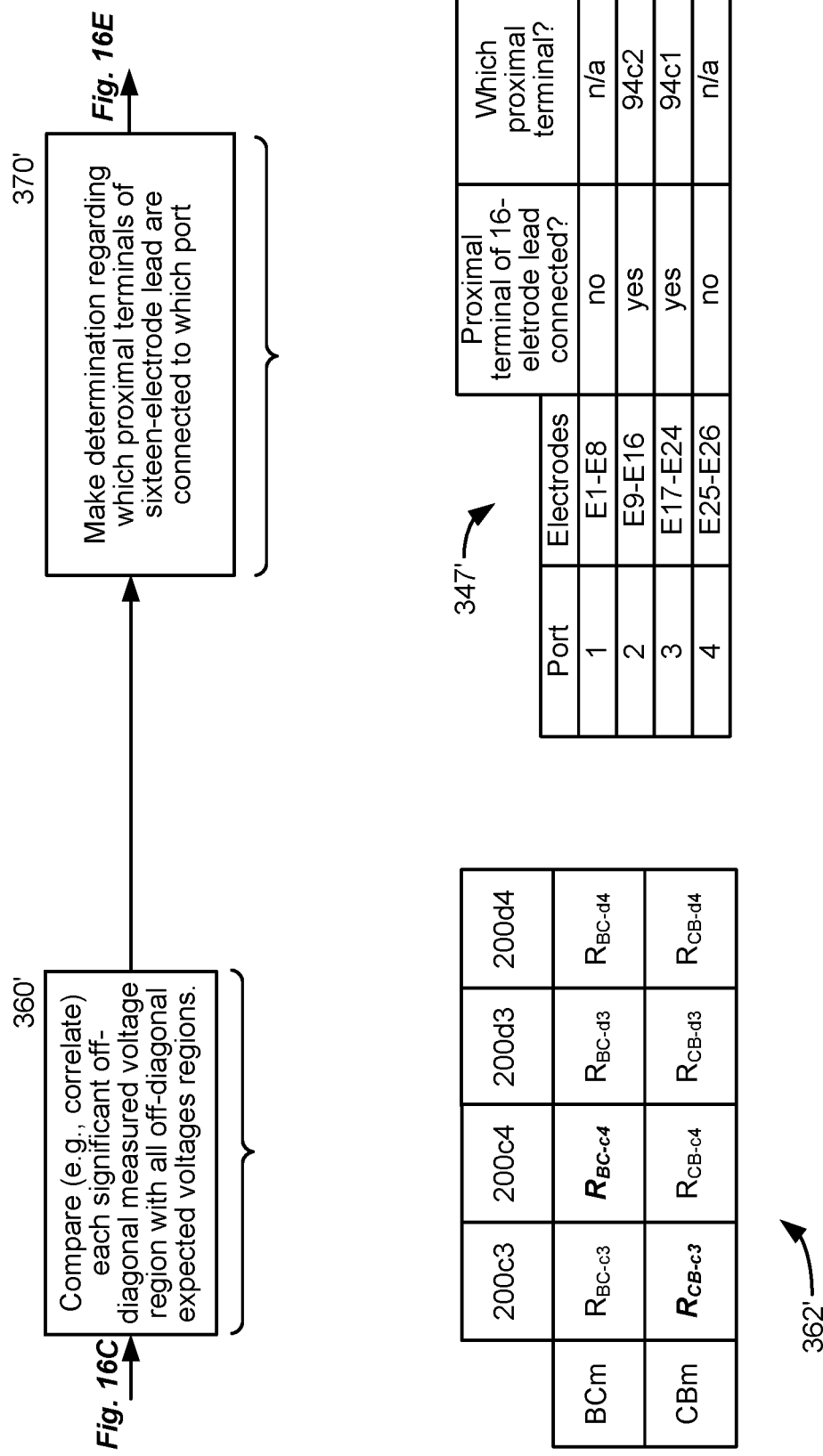

If significant off-diagonal measured regions are present, the algorithm 120' proceeds to FIG. 16D, where in step 360' each significant region is compared (e.g., correlated) against the off-diagonal expected voltages (200c3, 200c4, 200d3, and 200d4) identified earlier, as shown in table 362'. Because significant off-diagonal measured regions BCm and CBm best correlate with off-diagonal expected voltages 200c4 and 200c3 respectively, this informs that the sixteen-electrode lead is type 90c, and that its proximal terminals 94c2 and 94c1 are connected to ports 2 and 3 respectively, as shown in updated table 347'.

At this point, and proceeding to FIG. 16E, the initial port connection determination can be updated if necessary with the additional precision provided by the off-diagonal analysis. At this point, the algorithm 120' has finished identifying which leads and which proximal terminals appear to be connected to which ports of the IPG or ETS, and can inform the clinician of these connections. The GUI 100 may then present other options to the clinician. For example, and as shown in FIG. 16E, the GUI 100 can provide an option 375' to allow the clinician to assign the leads as they appear connected to the port in the GUI 100. Said another way, option 375' allows the clinician to populate the leads interface 106 and the leads assignment interface 112 of the GUI 100 with the connections determined. As before, a measure of confidence or its underlying data may be displayed to the user at the GUI 100, and can the absence of a lead or proximal terminal at a particular port.

To this point in the disclosure, it has been assumed that the values measured by the lead measurement algorithm 130 (FIG. 9) and the expected voltages 200i comprise voltages. This is sensible if a known current is used to provide test current I(test). However, a known voltage V(test) can also be used, resulting in measured currents. Therefore, the expected voltages 200i and the measured voltage matrix 190 could in other embodiments comprise expected currents and a measured current matrix. Furthermore, whether a known current (I(test)) is used and voltages measured, or whether a known voltage (V(test)) is used and current measured, the measurements may be expressed as resistances (or as inverted, conductances). Thus, in the disclosed technique, and using Ohm's law, the measured and/or expected values can comprise resistances or conductances as well as voltages or currents.

Further, it is not necessary to consider only the real part of voltage, current, resistance or conductance, or that measurements be taken at DC levels (e.g., via a square wave as illustrated earlier). The imaginary component of such parameters could also be used to augment the information. Determining both the real and imaginary components of these parameters may require making AC measurements. Measurements can be taken at different frequencies and averaged or a best frequency can be chosen. Further, measurements could be made using therapeutic pulses and not separate test pulse as described earlier. In short, the manners in which the measurements are made are not limited to the examples disclosed earlier.

Various aspects of the disclosed technique, including the lead measurement algorithm 130 and lead identification algorithm 120/120', and aspects used in the external devices to render and operate the GUI 100, can be formulated and stored as instructions in a non-transitory computer-readable media associated with the clinician programmer system 170, the external controller 160, the IPG 110, or the ETS 150, such as in a magnetic, optical, or solid state memory. The computer-readable media with such stored instructions may also comprise a device readable by the clinician programmer system 170 or external controller 160, such as in a memory stick or a removable disk, and may reside elsewhere. For example, the computer-readable media may be associated with a server or any other computer device, thus allowing instructions to be downloaded to the clinician programmer system 170 or external controller 160 or to the IPG 110 or ETS 150 via the Internet for example.

While the foregoing has illustrated application of the technique with respect to leads having distal ends 92i having ring and split-ring electrodes, it should be understood that the technique is not so limited. The technique can be applied to any arbitrary electrode array implantable in a patient, including arrays having tip electrodes, circular electrodes, arrays that aren't readily dividable into "rows", etc. The steps in algorithms 120 and 120' need not occur in the exact order illustrated, and instead the order of the steps can be changed, Further, not all steps are required, and other steps can be added.

In particular, it may be useful to consider the off-diagonal regions first in the algorithms 120 and 120'. As discussed earlier, this can inform early in the algorithm 120 or 120' that a sixteen electrode lead with two proximal terminals is used, and to what ports those proximal terminal are connected (e.g., steps 344, 344'). Correlation analysis to expected off-diagonal regions may then be used to determine which proximal contact of such sixteen-electrode leads is connected to which port (e.g., steps 360, 360'), which as noted earlier can be determined in particular by assessing the higher voltage elements 361 in the compared off-diagonal matrices. Knowing this information, on-diagonal analysis can then be used to determine (steps 320, 320') which single-proximal terminal leads are connected to which ports, and to determine which multiple-proximal terminal leads are connected to the already determined ports. Knowing that a sixteen-electrode lead is used at particular ports can simplify the on-diagonal analysis, because expected voltages for eight-electrode leads (e.g., 200a and 200b) can be ignored when assessing measured voltages from ports connected to sixteen electrode leads, and because expected voltages for sixteen-electrode leads (e.g., 200c1, 200c2, 200d1, 200d2) can be ignored when assessing measured voltages from other ports which are presumably connected to eight-electrode leads.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system for identifying one or more leads connected to one or more ports of an implantable stimulator device (ISD), wherein the ISD comprises a plurality I of ports, each port comprising a plurality of J device contacts coupleable to electrodes corresponding to that port, wherein the ISD supports N=J*I electrodes, the system comprising:
    an ISD to which one or more leads are connected, wherein each lead has a distal end comprising at least J electrodes and one or more proximal terminals, wherein the one or more proximal terminals for each lead comprises proximal contacts with each proximal contact connected to one of the at least J electrodes, wherein each of the one or more proximal terminals for each lead is connected to one of the ports of the ISD, wherein the ISD is configured to
    provide stimulation at each of the N electrodes, and
    measure a parameter at each of the N electrodes in response to the stimulation of each of the N electrodes, thus yielding N*N measured parameters; and
    an external device in communication with the ISD, wherein the external device comprises control circuitry configured to
    receive the measured parameters,
    retrieve expected parameters for a plurality of leads types useable by the ISD, and
    determine whether each of the one or more connected leads comprises a lead with one proximal terminal or a lead with a plurality of proximal terminals by comparing at least some of the measured parameters to the expected parameters.

2. The system of claim 1, wherein the ISD is configured to stimulate each of the N electrodes using a constant current, and wherein the parameter measured at each of the N electrodes comprises a voltage.

3. The system of claim 2, wherein the IPG comprises a case electrode, and wherein the ISD is configured to provide the constant current between each of the N electrodes and the case electrode.

4. The system of claim 1, wherein the control circuitry is further configured to:
    for each connected lead determined to have only one proximal terminal, determine that lead's type and the port of the ISD to which its proximal terminal is connected, and
    for each connected lead determined to have a plurality of proximal terminals, determine that lead's type and the ports of the ISD to which their plurality of proximal terminals are connected.

5. The system of claim 4, wherein the external device is further configured to
    indicate each determined connected lead type and the port to which each proximal terminal of each connected lead type is connected.

6. The system of claim 4, wherein the external device is further configured to
    allow a user to assign the connection of proximal terminals of one or more of the plurality of lead types to one or more of the plurality of ports of the ISD, and
    determine whether the determined lead types and the determined connection of those lead types' proximal terminals to particular ports of the ISD matches the assigned connections.

7. The system of claim 6, wherein the external device is further configured to
    if the determined lead types and the determined connection of those lead types' proximal terminals to particular ports don't match the assigned connections, notify the user of the mismatch.

8. The system of claim 6, wherein the external device is further configured to
    if the determined lead types and the determined connection of those lead types' proximal terminals to particular ports don't match the assigned connections, provide an option to reassign the connections to match the determined lead types and determined connection of those lead types' proximal terminals to particular ports of the ISD.

9. The system of claim 4, wherein the control circuitry is further configured to divide the measured parameters into first regions and second regions.

10. The system of claim 9, wherein each first region corresponds to one of the ports and comprises measured parameters when the J electrodes corresponding to that port are stimulated and measured.

11. The system of claim 10, wherein each second region comprises measured parameters when the J electrodes corresponding to a given port are stimulated and when the J electrodes corresponding to a different port are measured.

12. The system of claim 11, wherein if one of the plurality of lead types useable by the ISD comprises a lead having J electrodes and one proximal terminal, the retrieved expected parameters for that lead type comprises a third region of expected parameters.

13. The system of claim 12, wherein if one of the plurality of lead types useable by the ISD comprises a lead having at least J electrodes and more than one proximal terminal, the retrieved expected parameters for that lead type comprise fourth regions of expected parameters and fifth regions of expected parameters.

14. The system of claim 12, wherein the control circuitry is configured to compare the first regions to the third regions to determine, for each lead determined to have only one proximal terminal, that lead's type and the port of the ISD to which its proximal terminal is connected.

15. The system of claim 13, wherein each fourth region comprises expected parameters when J electrodes corresponding to one of the proximal terminals are stimulated and measured.

16. The system of claim 15, wherein each fifth region comprises expected parameters when J electrodes corresponding to one of the proximal terminals are stimulated and when J electrodes corresponding to a different one of the proximal terminals are measured.

17. The system of claim 16, wherein the control circuitry is configured to determine which of the second regions are significant second regions having significant values for its measured parameters, wherein the control circuitry is configured to compare the significant second regions to the fifth regions to determine if a connected lead comprises a plurality of proximal terminals, and which ports of the ISD its plurality of proximal terminals are connected.

18. The system of claim 17, wherein the control circuitry is configured to compare at least some of the first regions and significant second regions to the fourth regions and the fifth regions to determine, for each lead determined to have a plurality of proximal terminals, that lead's type and the ports of the ISD to which its proximal terminals are connected.

19. A method for identifying one or more leads connected to one or more ports of an implantable stimulator device (ISD), wherein the ISD comprises a plurality I of ports, each port comprising a plurality of J device contacts coupleable to electrodes corresponding to that port, wherein the ISD supports N=J*I electrodes, the method comprising:

(a) connecting one or more leads to the ISD, wherein each lead has a distal end comprising at least J electrodes and one or more proximal terminals, wherein the one or more proximal terminals for each lead comprises proximal contacts with each proximal contact connected to one of the at least J electrodes, wherein each of the one or more proximal terminals for each lead is connected to one of the ports of the ISD;

(b) providing stimulation at each of the N electrodes;

(c) measuring a parameter at each of the N electrodes in response to the stimulation of each of the N electrodes thus yielding N*N measured parameters, and receiving the measured parameters at an external device in communication with the ISD;

(d) retrieving at the external device expected parameters for a plurality of leads types useable by the ISD; and (e) determining in the external device whether each of the one or more connected leads comprises a lead with one proximal terminal or a lead with a plurality of proximal terminals by comparing at least some of the measured parameters to the expected parameters.

20. A non-transitory computer readable medium executable on an external device configured to communicate with an implantable stimulator device (ISD), wherein the ISD comprises a plurality I of ports, each port comprising a plurality of J device contacts coupleable to electrodes corresponding to that port, wherein the ISD supports N=J*I electrodes, wherein the medium includes instructions that when executed on the external device cause the external device to:

(a) instruct the ISD to provide stimulation at each of the N electrodes, wherein there are one or more leads connected to the ISD, wherein each lead has a distal end comprising at least J electrodes and one or more proximal terminals, wherein the one or more proximal terminals for each lead comprises proximal contacts with each proximal contact connected to one of the at least J electrodes, wherein each of the one or more proximal terminals for each lead is connected to one of the ports of the ISD;

(b) receive measured parameters from the ISD, wherein the measured parameters comprise a parameter measured at each of the N electrodes in response to the stimulation of each of the N electrodes, thus yielding N*N measured parameters;

(c) retrieve from the external device expected parameters for a plurality of leads types useable by the ISD; and (d) determine whether each of the one or more connected leads comprises a lead with one proximal terminal or a lead with a plurality of proximal terminals by comparing at least some of the measured parameters to the expected parameters.

* * * * *